US009867792B2

(12) United States Patent
Went et al.

(10) Patent No.: US 9,867,792 B2
(45) Date of Patent: *Jan. 16, 2018

(54) METHOD OF ADMINISTERING AMANTADINE PRIOR TO A SLEEP PERIOD

(71) Applicant: Adamas Pharma, LLC, Emeryville, CA (US)

(72) Inventors: Gregory T. Went, Mill Valley, CA (US); Gayatri Sathyan, Bangalore (IN); Kavita Vermani, Fremont, CA (US); Gangadhara Ganapati, Palo Alto, CA (US); Michael Coffee, Tiburon, CA (US); Efraim Shek, Pleasanton, CA (US); Ashok Katdare, Berkeley, CA (US)

(73) Assignee: Adamas Pharma, LLC, Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/428,980

(22) Filed: Feb. 9, 2017

(65) Prior Publication Data

US 2017/0151187 A1      Jun. 1, 2017

Related U.S. Application Data

(63) Continuation of application No. 14/863,035, filed on Sep. 23, 2015, now abandoned, which is a continuation of application No. 14/523,535, filed on Oct. 24, 2014, now abandoned, which is a continuation of application No. 14/267,597, filed on May 1, 2014, now abandoned, which is a continuation of application No. 12/959,321, filed on Dec. 2, 2010, now Pat. No. 8,741,343.

(60) Provisional application No. 61/266,053, filed on Dec. 2, 2009.

(51) Int. Cl.
| *A61K 9/22* | (2006.01) |
| *A61K 9/48* | (2006.01) |
| *A61K 31/13* | (2006.01) |
| *A61K 9/50* | (2006.01) |
| *A61K 9/00* | (2006.01) |

(52) U.S. Cl.
CPC ............ *A61K 31/13* (2013.01); *A61K 9/0002* (2013.01); *A61K 9/48* (2013.01); *A61K 9/4808* (2013.01); *A61K 9/50* (2013.01); *A61K 9/5015* (2013.01); *A61K 9/5026* (2013.01); *A61K 9/5047* (2013.01)

(58) Field of Classification Search
None
See application file for complete search history.

(56) References Cited

U.S. PATENT DOCUMENTS

| 3,152,180 A | 10/1964 | Haaf |
| 3,391,142 A | 7/1968 | Mills et al. |
| 3,992,518 A | 11/1976 | Chien et al. |
| 4,122,193 A | 10/1978 | Scherm et al. |
| 4,148,896 A | 4/1979 | Smith, Jr. et al. |
| 4,273,774 A | 6/1981 | Scherm |
| 4,284,444 A | 8/1981 | Bernstein et al. |
| 4,346,112 A | 8/1982 | Henkel et al. |
| 4,606,909 A | 8/1986 | Bechgaard et al. |
| 4,767,628 A | 8/1988 | Hutchinson |
| 4,769,027 A | 9/1988 | Baker et al. |
| 4,812,481 A | 3/1989 | Reischig et al. |
| 4,828,836 A | 5/1989 | Elger et al. |
| 4,839,177 A | 6/1989 | Colombo et al. |
| 4,897,268 A | 1/1990 | Tice et al. |
| 5,057,321 A | 10/1991 | Edgren et al. |
| 5,061,703 A | 10/1991 | Bormann et al. |
| 5,086,072 A | 2/1992 | Trullas et al. |
| 5,186,938 A | 2/1993 | Sablotsky et al. |
| 5,190,763 A | 3/1993 | Edgren et al. |
| 5,192,550 A | 3/1993 | Edgren et al. |
| 5,213,808 A | 5/1993 | Bar-Shalom et al. |
| 5,221,536 A | 6/1993 | Edgren et al. |
| 5,330,766 A | 7/1994 | Morella et al. |
| 5,334,618 A | 8/1994 | Lipton |
| 5,358,721 A | 10/1994 | Guittard et al. |
| 5,366,738 A | 11/1994 | Rork et al. |
| 5,378,474 A | 1/1995 | Morella et al. |
| 5,382,601 A | 1/1995 | Nuernberg et al. |
| 5,395,626 A | 3/1995 | Kotwal et al. |
| 5,422,120 A | 6/1995 | Kim |
| 5,422,123 A | 6/1995 | Conte et al. |
| 5,576,022 A | 11/1996 | Yang et al. |
| 5,601,845 A | 2/1997 | Buxton et al. |
| 5,614,560 A | 3/1997 | Lipton |
| 5,660,848 A | 8/1997 | Moo-Young |

(Continued)

FOREIGN PATENT DOCUMENTS

| AU | 2002323873 B2 | 11/2006 |
| CA | 2323805 A1 | 9/1999 |

(Continued)

OTHER PUBLICATIONS

Benson, et al. Optimisation of Drug Delivery 3. Sustained/Controlled-Release Oral Drug Delivery. The Australian Journal of Hospital Pharmacy 27.5 (1997): 381-389.
Dr. Gabriele Ahrens. Opposition against EP2506709B1 of Adams Pharmaceuticals, Inc. US dated Apr. 20, 2017 filed in European Patent Office.
Guidance for Industry—Bioavailability and Bioequivalence Studies Submitted in NDAs or INDs—General Considerations. U.S. Department of Health and Human Services Food and Drug Administration Center for Drug Evaluation and Research (CDER). Mar. 2014. Biopharmaceutics.

(Continued)

*Primary Examiner* — Kevin S Orwig
(74) *Attorney, Agent, or Firm* — Cooley LLP

(57) ABSTRACT

Methods of nighttime administration of amantadine to reduce sleep disturbances in patient undergoing treatment with amantadine are described, as well as compositions of extended release amantadine that are suitable for nighttime administration.

19 Claims, 7 Drawing Sheets

(56) References Cited

U.S. PATENT DOCUMENTS

| | | |
|---|---|---|
| 5,756,115 A | 5/1998 | Moo-Young et al. |
| 5,849,800 A | 12/1998 | Smith |
| 5,891,885 A | 4/1999 | Caruso |
| 5,912,013 A | 6/1999 | Rudnic et al. |
| 5,919,826 A | 7/1999 | Caruso |
| 6,046,232 A | 4/2000 | Kelleher et al. |
| 6,057,364 A | 5/2000 | Jasys et al. |
| 6,066,652 A | 5/2000 | Zenner et al. |
| 6,114,392 A | 9/2000 | Gilad et al. |
| 6,183,770 B1 | 2/2001 | Muchin et al. |
| 6,187,338 B1 | 2/2001 | Caruso et al. |
| 6,194,000 B1 | 2/2001 | Smith et al. |
| 6,217,905 B1 | 4/2001 | Edgren et al. |
| 6,251,430 B1 | 6/2001 | Zhang et al. |
| 6,284,276 B1 | 9/2001 | Rudnic et al. |
| 6,290,990 B1 | 9/2001 | Grabowski et al. |
| 6,372,255 B1 | 4/2002 | Saslawski et al. |
| 6,384,083 B1 | 5/2002 | Ludwig et al. |
| 6,392,104 B1 | 5/2002 | Ishii et al. |
| 6,444,702 B1 | 9/2002 | Wang et al. |
| 6,479,553 B1 | 11/2002 | McCarthy |
| 6,491,949 B2 | 12/2002 | Faour et al. |
| 6,569,463 B2 | 5/2003 | Patel et al. |
| 6,620,845 B2 | 9/2003 | Wang et al. |
| 6,635,268 B2 | 10/2003 | Peery et al. |
| 6,715,485 B1 | 4/2004 | Djupesland |
| 6,717,012 B2 | 4/2004 | Wang et al. |
| 6,743,211 B1 | 6/2004 | Prausnitz et al. |
| 6,746,689 B2 | 6/2004 | Fischer et al. |
| 6,753,011 B2 | 6/2004 | Faour |
| 6,764,697 B1 | 7/2004 | Jao et al. |
| 6,852,889 B2 | 2/2005 | Wang et al. |
| 6,919,373 B1 | 7/2005 | Lam et al. |
| 6,923,800 B2 | 8/2005 | Chen et al. |
| 6,929,803 B2 | 8/2005 | Wong et al. |
| 6,939,556 B2 | 9/2005 | Lautenbach |
| 6,945,952 B2 | 9/2005 | Kwon |
| 6,962,717 B1 | 11/2005 | Huber et al. |
| 7,211,275 B2 | 5/2007 | Ying et al. |
| 7,619,007 B2 | 11/2009 | Went et al. |
| 7,718,677 B2 | 5/2010 | Quik et al. |
| 7,858,660 B2 | 12/2010 | Nguyen et al. |
| 7,981,930 B2 | 7/2011 | Nguyen et al. |
| 8,039,009 B2 | 10/2011 | Rastogi et al. |
| 8,058,291 B2 | 11/2011 | Went et al. |
| 8,168,209 B2 | 5/2012 | Went et al. |
| 8,173,708 B2 | 5/2012 | Went et al. |
| 8,252,331 B2 | 8/2012 | Meyer et al. |
| 8,263,125 B2 | 9/2012 | Vaya et al. |
| 8,268,352 B2 | 9/2012 | Vaya et al. |
| 8,283,379 B2 | 10/2012 | Went et al. |
| 8,293,794 B2 | 10/2012 | Went et al. |
| 8,313,770 B2 | 11/2012 | Pathak et al. |
| 8,329,752 B2 | 12/2012 | Went et al. |
| 8,338,485 B2 | 12/2012 | Went et al. |
| 8,338,486 B2 | 12/2012 | Went et al. |
| 8,357,397 B2 | 1/2013 | Bouwstra et al. |
| 8,362,085 B2 | 1/2013 | Went et al. |
| 8,389,008 B2 | 3/2013 | Baichwal et al. |
| 8,389,578 B2 | 3/2013 | Went et al. |
| 8,426,472 B2 | 4/2013 | Went et al. |
| 8,574,626 B2 | 11/2013 | Vergez et al. |
| 8,580,858 B2 | 11/2013 | Went et al. |
| 8,591,947 B2 | 11/2013 | Vergez et al. |
| 8,598,233 B2 | 12/2013 | Went et al. |
| 8,637,080 B2 | 1/2014 | Pastini et al. |
| 8,741,343 B2 | 6/2014 | Went et al. |
| 8,796,337 B2 | 8/2014 | Went et al. |
| 8,821,928 B2 | 9/2014 | Hemmingsen et al. |
| 8,889,740 B1 | 11/2014 | Went et al. |
| 8,895,614 B2 | 11/2014 | Went et al. |
| 8,895,615 B1 | 11/2014 | Went et al. |
| 8,895,616 B1 | 11/2014 | Went et al. |
| 8,895,617 B1 | 11/2014 | Went et al. |
| 8,895,618 B1 | 11/2014 | Went et al. |
| 8,920,837 B2 | 12/2014 | Pilgaonkar et al. |
| 8,987,333 B2 | 3/2015 | Went et al. |
| 9,072,697 B2 | 7/2015 | Went et al. |
| 2001/0031278 A1 | 10/2001 | Oshlack et al. |
| 2002/0071863 A1 | 6/2002 | Dong et al. |
| 2003/0045577 A1 | 3/2003 | Madhat |
| 2003/0082230 A1 | 5/2003 | Baichwal et al. |
| 2003/0170302 A1 | 9/2003 | Seth et al. |
| 2003/0203055 A1 | 10/2003 | Rao et al. |
| 2004/0087658 A1 | 5/2004 | Moebius |
| 2004/0097484 A1 | 5/2004 | Cantillion et al. |
| 2004/0102525 A1 | 5/2004 | Kozachuk |
| 2004/0106681 A1 | 6/2004 | Rao et al. |
| 2004/0122090 A1 | 6/2004 | Lipton |
| 2004/0185097 A1 | 9/2004 | Kannan et al. |
| 2004/0224020 A1 | 11/2004 | Schoenhard |
| 2005/0031651 A1 | 2/2005 | Gervais et al. |
| 2005/0065219 A1 | 3/2005 | Lipton et al. |
| 2005/0119249 A1 | 6/2005 | Buntinx |
| 2005/0124701 A1 | 6/2005 | Went et al. |
| 2005/0153953 A1 | 7/2005 | Trippodi-Murphy et al. |
| 2005/0191349 A1 | 9/2005 | Boehm et al. |
| 2005/0202088 A1 | 9/2005 | Hanshermann et al. |
| 2005/0208132 A1 | 9/2005 | Sathyan et al. |
| 2005/0209218 A1 | 9/2005 | Meyerson et al. |
| 2005/0232990 A1 | 10/2005 | Boehm et al. |
| 2005/0245460 A1 | 11/2005 | Meyerson et al. |
| 2005/0245617 A1 | 11/2005 | Meyerson et al. |
| 2005/0267176 A1 | 12/2005 | Barberich |
| 2005/0271708 A1 | 12/2005 | Thombre |
| 2006/0008527 A1 | 1/2006 | Lagoviyer et al. |
| 2006/0051416 A1 | 3/2006 | Rastogi et al. |
| 2006/0052370 A1 | 3/2006 | Meyerson et al. |
| 2006/0062851 A1 | 3/2006 | Vergez et al. |
| 2006/0063810 A1 | 3/2006 | Vergez et al. |
| 2006/0142398 A1 | 6/2006 | Went et al. |
| 2006/0159763 A1 | 7/2006 | Meyer et al. |
| 2006/0189694 A1 | 8/2006 | Went et al. |
| 2006/0240043 A1 | 10/2006 | Meyerson et al. |
| 2006/0251717 A1 | 11/2006 | Firestone et al. |
| 2006/0252788 A1 | 11/2006 | Went et al. |
| 2007/0036843 A1 | 2/2007 | Hirsh et al. |
| 2007/0104778 A1 | 5/2007 | Zeng et al. |
| 2007/0184112 A1 | 8/2007 | Wong et al. |
| 2007/0270443 A1 | 11/2007 | Went et al. |
| 2008/0057123 A1 | 3/2008 | Grenier et al. |
| 2008/0089861 A1 | 4/2008 | Went et al. |
| 2008/0227743 A1 | 9/2008 | Nguyen et al. |
| 2008/0248107 A1 | 10/2008 | Pilgaonkar et al. |
| 2008/0260825 A1 | 10/2008 | Quik et al. |
| 2008/0274061 A1 | 11/2008 | Schollmayer et al. |
| 2008/0279819 A1 | 11/2008 | Went et al. |
| 2009/0041820 A1 | 2/2009 | Wu et al. |
| 2009/0169587 A1 | 7/2009 | Baichwal et al. |
| 2009/0196908 A1 | 8/2009 | Lee et al. |
| 2009/0220613 A1 | 9/2009 | Odidi et al. |
| 2009/0247481 A1 | 10/2009 | Nguyen et al. |
| 2010/0004251 A1 | 1/2010 | Barberich |
| 2010/0029723 A1 | 2/2010 | Quik et al. |
| 2010/0047342 A1 | 2/2010 | Went et al. |
| 2010/0092554 A1 | 4/2010 | Reess et al. |
| 2010/0092562 A1 | 4/2010 | Hollenbeck et al. |
| 2010/0137448 A1 | 6/2010 | Lipton et al. |
| 2010/0158895 A1 | 6/2010 | Quik et al. |
| 2010/0159001 A1 | 6/2010 | Cardinal et al. |
| 2010/0166735 A1 | 7/2010 | Quik et al. |
| 2010/0196463 A1 | 8/2010 | Quik et al. |
| 2010/0221324 A1 | 9/2010 | Petereit et al. |
| 2010/0221328 A1 | 9/2010 | Wertz et al. |
| 2010/0239635 A1 | 9/2010 | McClain et al. |
| 2010/0260838 A1 | 10/2010 | Went et al. |
| 2010/0266684 A1 | 10/2010 | Went et al. |
| 2010/0311697 A1 | 12/2010 | Went et al. |
| 2011/0053981 A1 | 3/2011 | Ieni et al. |
| 2011/0059169 A1 | 3/2011 | Went et al. |
| 2011/0064804 A1 | 3/2011 | Went et al. |
| 2011/0077276 A1 | 3/2011 | Quik et al. |
| 2011/0142905 A1 | 6/2011 | Bar-Shalom et al. |
| 2011/0189273 A1 | 8/2011 | Went et al. |

(56) References Cited

U.S. PATENT DOCUMENTS

| | | |
|---|---|---|
| 2011/0230432 A1 | 9/2011 | Nguyen et al. |
| 2011/0287094 A1 | 11/2011 | Penhasi et al. |
| 2012/0045506 A1 | 2/2012 | Baer et al. |
| 2012/0045508 A9 | 2/2012 | Went et al. |
| 2012/0046365 A1 | 2/2012 | Went et al. |
| 2012/0064167 A1 | 3/2012 | Hall et al. |
| 2012/0264783 A1 | 10/2012 | Went et al. |
| 2012/0264829 A1 | 10/2012 | Went et al. |
| 2012/0264978 A1 | 10/2012 | Went et al. |
| 2012/0288560 A1 | 11/2012 | Went et al. |
| 2013/0022676 A1 | 1/2013 | Mullen et al. |
| 2013/0059008 A1 | 3/2013 | Atkinson et al. |
| 2013/0115249 A1 | 5/2013 | Vergez et al. |
| 2013/0131110 A1 | 5/2013 | Went et al. |
| 2013/0165517 A1 | 6/2013 | Went et al. |
| 2013/0165527 A1 | 6/2013 | Went et al. |
| 2013/0317115 A1 | 11/2013 | Went et al. |
| 2014/0134243 A1 | 5/2014 | Went et al. |
| 2014/0179797 A1 | 6/2014 | Went et al. |
| 2014/0193490 A1 | 7/2014 | Schoenhard |
| 2014/0242163 A1 | 8/2014 | Went et al. |
| 2014/0323582 A1 | 10/2014 | Went et al. |
| 2014/0336266 A1 | 11/2014 | Went et al. |
| 2014/0343152 A1 | 11/2014 | Went et al. |
| 2014/0343153 A1 | 11/2014 | Went et al. |
| 2014/0343154 A1 | 11/2014 | Went et al. |
| 2014/0343163 A1 | 11/2014 | Went et al. |
| 2014/0343164 A1 | 11/2014 | Went et al. |
| 2014/0356425 A1 | 12/2014 | Went et al. |
| 2015/0045438 A1 | 2/2015 | Went et al. |
| 2015/0045439 A1 | 2/2015 | Went et al. |
| 2015/0045446 A1 | 2/2015 | Went et al. |
| 2015/0045447 A1 | 2/2015 | Went et al. |
| 2015/0045448 A1 | 2/2015 | Went et al. |
| 2015/0051292 A1 | 2/2015 | Went et al. |
| 2015/0057355 A1 | 2/2015 | Went et al. |
| 2015/0087721 A1 | 3/2015 | Went et al. |
| 2015/0119465 A1 | 4/2015 | Went et al. |
| 2015/0126605 A1 | 5/2015 | Went et al. |
| 2015/0126612 A1 | 5/2015 | Went et al. |
| 2015/0150991 A1 | 6/2015 | Pilgaonkar et al. |
| 2015/0157579 A1 | 6/2015 | Went et al. |
| 2015/0297537 A1 | 10/2015 | Went et al. |
| 2016/0151307 A1 | 6/2016 | Went et al. |
| 2016/0256413 A1 | 9/2016 | Went et al. |
| 2016/0256414 A1 | 9/2016 | Went et al. |
| 2016/0263052 A1 | 9/2016 | Went et al. |
| 2016/0263053 A1 | 9/2016 | Went et al. |
| 2016/0263054 A1 | 9/2016 | Went et al. |
| 2016/0263055 A1 | 9/2016 | Went et al. |
| 2016/0263056 A1 | 9/2016 | Went et al. |
| 2016/0263057 A1 | 9/2016 | Went et al. |
| 2016/0263058 A1 | 9/2016 | Went et al. |
| 2017/0056340 A1 | 3/2017 | Went et al. |
| 2017/0151183 A1 | 6/2017 | Went et al. |
| 2017/0151184 A1 | 6/2017 | Went et al. |
| 2017/0151185 A1 | 6/2017 | Went et al. |
| 2017/0151186 A1 | 6/2017 | Went et al. |
| 2017/0151189 A1 | 6/2017 | Went et al. |
| 2017/0151190 A1 | 6/2017 | Went et al. |

FOREIGN PATENT DOCUMENTS

| | | |
|---|---|---|
| EP | 0392059 A1 | 10/1990 |
| EP | 0502642 A1 | 9/1992 |
| EP | 0524968 A1 | 2/1993 |
| EP | 0870757 A2 | 10/1998 |
| EP | 0927711 A1 | 7/1999 |
| EP | 0870757 A3 | 6/2000 |
| EP | 1600156 A2 | 11/2005 |
| EP | 1827385 A2 | 9/2007 |
| EP | 1832298 A1 | 9/2007 |
| EP | 1845968 A2 | 10/2007 |
| EP | 1509232 B1 | 11/2008 |
| EP | 2343057 A1 | 7/2011 |
| EP | 2506709 A2 | 10/2012 |
| EP | 1827385 B1 | 3/2013 |
| EP | 2623099 A1 | 8/2013 |
| GB | 1173492 A | 12/1969 |
| JP | S584718 A | 1/1983 |
| JP | H10203966 A | 8/1998 |
| JP | 2002506047 A | 2/2002 |
| JP | 2003523989 A | 8/2003 |
| WO | WO-8909051 A1 | 10/1989 |
| WO | WO-9106291 A1 | 5/1991 |
| WO | WO-9114445 A1 | 10/1991 |
| WO | WO-9405275 A1 | 3/1994 |
| WO | WO-9513796 A1 | 5/1995 |
| WO | WO-9714415 A1 | 4/1997 |
| WO | WO-9818457 A1 | 5/1998 |
| WO | WO-9945963 A1 | 9/1999 |
| WO | WO-0000197 A1 | 1/2000 |
| WO | WO-0018378 A1 | 4/2000 |
| WO | WO-0119901 A2 | 3/2001 |
| WO | WO-0132148 A1 | 5/2001 |
| WO | WO-0146291 A1 | 6/2001 |
| WO | WO-0162706 A1 | 8/2001 |
| WO | WO-0119901 A3 | 9/2001 |
| WO | WO-0245710 A1 | 6/2002 |
| WO | WO-03101458 A1 | 12/2003 |
| WO | WO-2004012700 A2 | 2/2004 |
| WO | WO-2004012700 A3 | 4/2004 |
| WO | WO-2004/037190 A2 | 5/2004 |
| WO | WO-2004/037190 A3 | 5/2004 |
| WO | WO-2004037234 A2 | 5/2004 |
| WO | WO-2004037234 A3 | 8/2004 |
| WO | WO-2004087116 A2 | 10/2004 |
| WO | WO-2004087116 A3 | 12/2004 |
| WO | WO-2005072705 A1 | 8/2005 |
| WO | WO-2005079773 A2 | 9/2005 |
| WO | WO-2005079773 A3 | 10/2005 |
| WO | WO-2006058059 A2 | 6/2006 |
| WO | WO-2006058236 A2 | 6/2006 |
| WO | WO-2006058059 A3 | 7/2006 |
| WO | WO-2006070781 A1 | 7/2006 |
| WO | WO-2006089494 A1 | 8/2006 |
| WO | WO-2006121560 A2 | 11/2006 |
| WO | WO-2007022255 A2 | 2/2007 |
| WO | WO-2007136737 A1 | 11/2007 |
| WO | WO-2008112775 A1 | 9/2008 |
| WO | WO-2011069010 A2 | 6/2011 |
| WO | WO-2011069010 A3 | 7/2011 |
| WO | WO-2014204933 A1 | 12/2014 |

OTHER PUBLICATIONS

Guidance for Industry—Statistical approaches to establishing bioequivalence. U.S. Department of Health and Human Services Food and Drug Administration Center for Drug Evaluation and Research (CDER). Jan. 2001. BP.

Neutel, et al. Novel delivery system for verapamil designed to achieve maximal blood pressure control during the early morning. American heart journal 132.6 (1996): 1202-1206.

Parkes, J. D. Clinical pharmacology of amantadine and derivatives. Early Diagnosis and Preventive Therapy in Parkinson's Disease. Springer Vienna, 1989. 335-341.

U.S. Pharmacopoeia, Chapter 711-Dissolution (Jan. 2006). Available from http://www.pharmacopeia.cn/v29240/usp29nf24s0_c711h.html.

2006 Chemical Abstracts Service Catalog. Published 2006 by Chemical Abstracts Service, p. 52.

Alisky et al., A case history illustrating how extended release cholinesterase inhibitors could improve management of Alzheimer's disease. J. Alzheimer's Dis. Dec. 2003, 5(6):477-78.

Amantadine Drug Info. Website (http://www.nlm.nih.gov/medlineplus/druginfo/meds/a682064.html; available at least by Dec. 7, 2008; accessed online Jun. 2, 2015.

Ambrozi, et al. Treatment of Impaired Cerebral Function in Psychogeriatric Patients with Memantine—Results of a Phase II Double-Blind Study. Pharmacopsychiat. 1988; 21(3):144-46.

(56) References Cited

OTHER PUBLICATIONS

Anand et al., "Dissolution Testing: An FDA Perspective," AAPS Workshop, Physical Pharmacy and Biopharmaceutics, May 13, 2009, 1-32.
Antonelli, et al. Experimental studies and theoretical aspects on A2A/D2 receptor interactions in a model of Parkinson's disease. Relevance for L-dopa induced dyskinesias. J Neurol Sci 2006;248:16-22.
Avery's Drug Treatment: Principles and Practice of Clinical Pharmacology and Therapeutics, 3rd Edition, 1987, edited by Trevor M. Speight, Chapter VIII, pp. 255-282.
AXURA Summary of Product Characteristics, 2002, p. 1-16.
Bandini, et al. The visuo-cognitive and motor effect of amantadine in non-Caucasian patients with Parkinson's disease. A clinical and electrophysiological study. J Neural Transm. 2002;109(1):41-51.
Bara-Jimenez, et al. Effects of serotonin 5-HT1A agonist in advanced Parkinson's disease. Mov Disord 2005; 20:932-936.
Beers, M.H. and Berkow, R. Editors-in-chief, The Merck Manual of Diagnosis and Therapy, 17th Edition, pp. 1525-1544,1999.
Bentue-Ferrer, et al. Medication in Alzheimer's disease, Rev. Geriatr. 26(6):511-522 (2001), (in French with English summary).
Berman, et al. Antidepressant effects of ketamine in depressed patients. Biol. Psychiatry. 2000; 47:351-354.
Bhat, et al. Localization of the N-methyl-D-aspartate R1 receptor subunit in specific anterior pituitary hormone cell types of the female rat. Neuroendocrinol. 1995; 62(2):178-186.
Bibbiani, et al. Serotonin 5-HT1A agonist improves motor complications in rodent and primate parkinsonian models. Neurology 2001;27:1829-1834.
Blanpied, et al. Trapping Channel Block of NMDA-Activated Responses by Amantadine and Memantine, J. of Neurophysiology, 77: 309-323 (1997).
Bliss, et al. A synaptic model of memory: long-term potentiation in the hippocampus. Nature. 1993; 361:31-39.
Bonelli, R. Editorial comment—How to treat vascular dementia? Stroke. Oct. 2003, 34(10):2331-2. Epub. Sep. 18, 2003.
Bonnett, A. Involvement of Non-Dopaminergic Pathways in Parkinson's Disease: Pathophysiology and Therapeutic Implications. CNS Drugs, vol. 13, No. 5, May 2000 , pp. 351-364(14).
Braga, et al. Making crystals from crystals: a green route to crystal engineering and polymorphism, Chemical Communications pp. 3635-3645 (2005).
Bredt, et al. Localization of nitric oxide synthase indicating a neural role for nitric oxide. Nature. 1990; 347:768-770.
Budziszewska, et al. Antidepressant drugs inhibit glucocorticoid receptor-mediated gene transcription—a possible mechanism. Br. J. Pharmacol. Jul. 2000; 130(6):1385-93.
Cacabelos, et al. Pharmacological treatment of Alzheimer disease: From psychotropic drugs and cholinesterase inhibitors to pharmacogenomics. Drugs Today. 2000; 36(7):415-499.
CDER "Guidance for Industry Extended Release Oral Dosage Forms: Development, Evaluation, and Application of In Vitro/In Vivo Correlations" Sep. 1997, U.S. Department of Health and Human Services Food and Drug Administration, pp. 1-24.
Cersosimo, et al. Amantadine for the treatment of levodopa dyskinesias in Parkinson's disease. Medicina (B Aires). 2000; 60(3):321-5. (full English translation).
Chen, et al. Open-channel block of N-methyl-D-aspartate (NMDA) responses by memantine: therapeutic advantage against NMDA receptor-mediated neurotoxicity. J. Neurosci. 1992; 12(11):4427-4436.
Choi, DW. Glutamate neurotoxicity and diseases of the nervous system. Neuron. 1988; 1:623-634.
Chung, et al. Clinical pharmacokinetics of doxazosin in a controlled-release gastrointestinal therapeutic system (GITS) formulation, Br. J. Clin. Pharmacol. 1999, 48:678-87.
Colomiso, et al. Task Force Report on Scales to Assess Dyskinesia in Parkinson's Disease: Critique and Recommendations. Movement Disorders, 2010, p. 1-12.
Crosby, et al. Amantadine for dyskinesia in Parkinson's disease. Cochrane Database of Systematic Reviews 2003, Issue 2. DOI: 10.1002/14651858.CD003467.
Crosby, et al. Amantadine in Parkinson's disease. Cochrane Database of Systematic Reviews 2003, Issue 1. DOI: 10.1002/14651858.CD003468.
Cummings, J. L. Depression and Parkinson's Disease: A Review. The American Journal of Psychiatry. 1992; 149(4): 443-454.
Cutler, RG. Human longevity and aging: possible role of reactive oxygen species. Ann. New York Acad. Sci. 1991; 621:1-28.
Da Silva-Junior, et al. Amantadine reduces the duration of levodopa-induced dyskinesia: A randomized, double-blind, placebo-controlled study. Parkinsonism Relat Disord. Nov. 2005;11(7):449-52.
Danysz, et al. Aminoadamantanes as NMDA receptor antagonists and antiparkinsonian agents—preclinical studies. Neurosci. Biobehav. Rev. 1997; 21(4):455-468.
Das, et al. Controlled-Release of Oral Dosage Forms. "Formulation, Fill & Finish," 10-16 (2003).
Declaration of Richard C. Moreton in Support of Defendants' Opening Claim Construction Brief. Mar. 26, 2015, pp. 1-17.
Declaration of Richard F. Bergstrom, Ph.D. Mar. 26, 2015, pp. 1-50.
Defendants' Opening Claim Construction Brief. Mar. 27, 2015, pp. 1-35.
Defendants' Reply Claim Construction Brief. Jul. 15, 2015, pp. 1-14.
Defendants' Second Revised Joint Initial Invalidity Contentions. Jan. 23, 2015, pp. 1-122.
Del Dotto, et al. Intravenous amantadine improves levadopa-induced dyskinesias: an acute double-blind placebo-controlled study. Mov Disord. May 2001;16(3):515-20.
Di Monte, et al. Relationship among nigrostriatal denervation, parkinsonism, and dyskinesias in the MPTP primate model. Mov Disord. May 2000;15(3):459-66.
Ditzler, K. Efficacy and Tolerability of Memantine in Patients with Dementia Syndrome, Arnzneim.-Forsch./Drug Res. 41 (II), Nr. 8, 773-780 (1991), Bad Krozingen, Germany.
EBIXA Package leaflet, 2012, p. 1-7.
Engber, et al. NMDA receptor blockade reverses motor response alterations induced by levodopa. Neuroreport. Dec. 20, 1994; 5(18):2586-88.
Erkulwalter and Pillai, Southern Medical Journal, "Amantadine HCl for treatment of dementia," 79:9, Suppl. 2, 30 (1986).
European search report dated Apr. 22, 2013 for EP Application No. 10835150.3.
European search report dated Jun. 10, 2011 for EP 10179758.7.
European search report dated Sep. 27, 2010 for EP 10075323.5.
European search report dated Oct. 15, 2007 for Application No. 07000173.0.
Fachinfo-Service: Amantadin-CT 100 mg Filmtabletten. 2004, Rote Liste Service GmBh, Berlin, pp. 1-5. (in German with English translation).
Fahn, et al. Long-term evaluation of amantadine and levodopa combination in parkinsonism by double-blind crossover analyses. Neurology. Aug. 1975; 25(8):695-700.
FDA Medical Review for Namenda.RTM. NDA 21-487, Oct. 2, 2003, pp. 1-190.
Fehling, C. The effect of adding amantadine to optimum L-dopa dosage in Parkinson's syndrome. Acta Neurol Scand. 1973;49(2):245-51.
Fleischhacker, et al. Memantine in the treatment of senile dementia of the Alzheimer type. Prog. Neuropsychopharmacol. Biol. Psychiatry. 1986; 10(1):87-93.
Forest Pharmaceuticals Inc. Namenda 2003 Label.
Forstl, H. Symptomatic therapy of Alzheimer dementia. Wien Med Wochenschr. 2002; 152(3-4):77-80 (in German with English translation).
Foster, et al. Neurobiology. Taking apart NMDA receptors. Nature. 1987; 329(6138):395-6.
Fox, et al. Memantine combined with an acetyl cholinesterase inhibitor—hope for the future? Neuropsychiatr. Dis. Treat. Jun. 2006; 2(2):121-25.

(56) References Cited

OTHER PUBLICATIONS

Franz et al., "Percutaneous Absorption on the Relevance of In Vitro Data," J. Invest. Derm. vol. 64, 1975, pp. 194-195.
Fredriksson, et al. Co-administration of memantine and amantadine with sub/suprathreshold doses of L-Dopa restores motor behaviour of MPTP-treated mice. J. Neural Transm. 2001; 108(2):167-87.
Fung et al., "Drugs for Parkinson's Disease," Australian Prescriber, 24(4) (2001), pp. 92-95.
Galinsky., "Basic Pharmacokinetcs. Remington: The Practice and Science of Pharmacy, 20th Ed. (2000), Ch. 58, p. 1127-1144."
Garthwaite, et al. Endothelium-derived relaxing factor release on activation of NMDA receptors suggests role as intercellular messenger in the brain. Nature. 1988; 336(6197):385-88.
Goetz, et al. Sarizotane as a treatment of dykinesias in parkinson's disease: a double-blind Placebo controlled trial. Mov Disord 2007;22:179-186.
Goetz, et al. Movement Disorder Society Task Force report on the Hoehn and Yahr staging scale: status and recommendations. Mov Disord. Sep. 2004;19(9):1020-8.
Goetz, et al. Movement Disorder Society-sponsored revision of the Unified Parkinson's Disease Rating Scale (MDS-UPDRS): scale presentation and clinimetric testing results. Mov Disord. Nov. 15, 2008;23(15):2129-70. doi: 10.1002/mds.22340.
Gracies JM, Olanow CW; Current and Experimental Therapeutics of Parkinson's Disease; Neuropsychopharmacology: the Fifth Generation of Progress, p. 1802; American College of Neuropsychopharmacology (2002).
Greenamyre et al., "Antiparkinsonian effects of remacemide hydrochloride, a glutamate antagonist, in rodent and primate models of Parkinson's disease" Annals of Neurology, vol. 35, No. 6, 1994, pp. 655-661, XP009068858 ISSN: 0364-5134.
Greenberg, et al. Treatment of Major Depression and Parkinson's Disease with Combined Phenelzine and Amantadine. Am. J. Psychiatry. 1985; 142(2):273-274.
Greene, T.W. Protective Groups in Organic Synthesis. John Wiley & Sons, pp. 70-71 (1981).
Grynkiewicz, et al. A new generation of Ca2+ indicators with greatly improved fluorescence properties. J. Biol. Chem. 1985; 260(6):3440-3450.
Guidance for Industry: Food Effect Bioavailability and Fed Bioequivalence Studies. U.S. Department of Health and Human Services, FDA, CDER, Dec. 2002.
Guidance for Industry: Bioavailability and Bioequivalence Studies for Orally Administered Drug Products—General Considerations. U.S. Department of Health and Human Services, FDA, CDER, Mar. 2003.
Guidance for Industry. Waiver of In Vivo Bioavailability and Bioequivalence Studies for Immediate-Release Solid Oral Dosage Forms Based on a Biopharmaceutics Classification System. U.S. Department of Health and Human Services, FDA, CDER, Aug. 2000.
Guide to MS Medications, Multiple Sclerosis Society of Canada, 2004, p. 9.
Guideline on the investigation of bioequivalence. Committee for Medicinal Productsfor Human Use CHMP), CPMP/EWP/QWP/1401/98 Rev. 1, Jan. 20, 2010.
Guttman, et al. Current concepts in the diagnosis and management of Parkinson's disease. CMAJ. Feb. 4, 2003;168(3):293-301.
Hartmann, et al. Tolerability of memantine in combination with cholinesterase inhibitors in dementia therapy. Int. Clin. Physchopharmacol, 2003, 18(2):81-85.
Hayden, "Differences in Side Effects of Amantadine Hydrochloride and Rimantadine Hydrochloride Relate to Differences in Pharmacokinetics," AAC, 23(3) 1983, pp. 458-464.
Hayden, et al. Comparative single-dose pharmacokinetics of amantadine hydrochloride and rimantadine hydrochloride in young and elderly adults. Antimicrob Agents Chemother. Aug. 1985;28(2):216-21.
Hayden, et al. Comparative Toxicity of Amantadine Hydrochloride and Rimantadine Hydrochloride in Healthy Adults. Antimicrobial Agents and Chemotherapy, vol. 19, No. 2, Feb. 1981, p. 226-233.
Hoffman, A. Pharmacodynamic aspects of sustained release preparations. Adv Drug Deliv Rev. Sep. 7, 1998;33(3):185-199.
Ing et al., "Toxic Effects of Amantadine in Patients with Renal Failure," CMA Journal, Mar. 1979, vol. 120, pp. 695-697.
International search report dated Feb. 7, 2011 for PCT/US2010/058789.
International search report dated Aug. 9, 2006 for PCT Application No. US2005/42780.
International search report dated Apr. 5, 2002 for PCT Application No. US2001/48516.
International search report dated May 8, 2006 for PCT Application No. US2005/42424.
International Search Report for PCT/US2006/013506, dated Jan. 12, 2007, Feb. 23, 2007 Corrected.
International written opinion dated Feb. 7, 2011for PCT/US2010/058789.
International written opinion dated Aug. 8, 2006 for PCT Application No. US2005/42780.
Jackson, et al. Chemoprophylaxis of viral respiratory diseases. Pan American Health Organization. 1967;595-603.
Jackson, "Prevention and control of influenza by chemoprophylaxis and chemotherapy. Prospects from examination of recent experience," JAMA, 235(25), (1976), 2739-2742.
Jain, et al. Polymorphism in Pharmacy, Indian Drugs 23(6):315-29 (1986).
Jenner, P. Preventing and controlling dyskinesia in Parkinson's disease—a view of current knowledge and future opportunities. Mov Disord. 2008;23 Suppl 3:S585-98.
Jones, R.W. Drug treatment of Alzheimer's disease. Reviews in Clinical Gerontology (2002) vol. 12, pp. 165-173.
Karcz-Kubicha, et al. Anxiolytic activity of glycine-B antagonists and partial agonists—no relation to intrinsic activity in the patch clamp. Neuropharmacol. 1997; 36(10):1355-67.
Klockgether, et al. Excitatory amino acids and the basal ganglia: implications for the therapy of Parkinson's disease. Trends Neurosci. 1989; 12(8):285-286.
Klockgether, et al. NMDA antagonists potentiate antiparkinsonian actions of L-dopa in monoamine-depleted rats. Ann. Neurol. Oct. 1990; 28(4):539-46.
Konitsiotis, et al. AMPA receptors blockade improves levodopa-induced dyskinesia in MPTP monkeys. Neurology 2000;54:1589-1595.
Kornhuber, et al. Amantadine and Memantine are NMDA receptor antagonists with neuroprotective properties. J. Neural Transm. Suppl. 1994; 43:91-104.
Kornhuber, et al. Cerebrospinal fluid and serum concentrations of the N-methyl-D-aspartate (NMDA) receptor antagonist memantine in man. Neurosci. Lett. 1995; 195(2):137-39.
Kornhuber, et al. Effects of the 1-amino-adamantanes at the MK-801-binding site of the NMDA-receptor-gated ion channel: a human postmortem brain study. Eur J. Pharmacol. 1991; 206(4):297-300.
Kornhuber, et al. Memantine displaces [3H]MK-801 at therapeutic concentrations in postmortem human frontal cortex. Eur. J. Pharmacol. 1989; 166(3):589-90.
Letter from British Library dated Aug. 11, 2008 re MMW Fortschritte.
Lewitt, et al. Adenosine A2A receptor antagonist istradefylline (KW-6002) reduces "off" time in Parkinson's disease: a double-blind, randomized, multicenter clinical trial (6002-US-005). Ann Neurol 2008;63:295-302.
Longer, M. A. Sustained-Release Drug Delivery Systems. In Remington's Pharmaceutical Sciences (1990) (Mack Publishing Company, 1990, 18th Ed.; Chapter 91: 1676-1693.
Luginger, et al. Beneficial effects of amantadine on L-dopa-induced dyskinesias in Parkinson's disease. Mov Disord. Sep. 2000;15(5):873-8.
Manson, et al. Idazoxan is ineffective for levodopa-induced dyskinesias in Parkinson's disease. Mov Disord 2000;15:336-337.

(56) References Cited

OTHER PUBLICATIONS

Marcea et al., Effect of memantine versus dh-Ergotoxin on Cerebro-organic Psycho-syndrome. Therapiewoche. 1988, 38:3097-3100 (with English summary).
McLean, et al. Prophylactic and therapeutic efficacy of memantine against seizures produced by soman in the rat. Toxicol Appl Pharmacol. Jan. 1992; 112(1):95-103.
Merims, et al. Riluzole for levodopa-induced dyskinesias in advanced Parkinson's disease. Lancet. May 22, 1999; 353(9166):1764-65.
Metman, et al. A trial of dextromethorphan in parkinsonian patients with motor response complications. Mov. Disord. May 1998; 13(3):414-17.
Metman, et al. Amantadine as treatment for dyskinesias and motor fluctuations in Parkinson's disease. Neurology. May 1998; 50(5):1323-26.
Metman, et al. Amantadine for levodopa-induced dyskinesias: a 1-year follow-up Study. Arch Neurol 1999;56:1383-1386.
Moryl, et al. Potential antidepressive properties of amantadine, memantine and bifemelane. Pharmacol. Toxicol. 1993; 72(6):394-397.
ND 21-487 Namenda Approved Labeling. 2003; p. 1-20.
Note for guidance on modified release oral and transdermal dosage forms: Section II (Pharmacokinetic and clinical evaluation). Committee for proprietary medicinal products, CPMP/EWP/280/96, Jul. 28, 1999.
Notice of allowance dated Jan. 23, 2015 for U.S. Appl. No. 14/451,262.
Notice of allowance dated Jan. 24, 2013 for U.S. Appl. No. 11/286,448.
Notice of allowance dated Apr. 11, 2014 for U.S. Appl. No. 12/959,321.
Notice of allowance dated May 18, 2015 for U.S. Appl. No. 14/591,641.
Notice of allowance dated Jun. 4, 2014 for U.S. Appl. No. 13/958,153.
Notice of allowance dated Oct. 9, 2014 for U.S. Appl. No. 14/328,440.
Notice of allowance dated Oct. 9, 2014 for U.S. Appl. No. 14/451,242.
Notice of allowance dated Oct. 9, 2014 for U.S. Appl. No. 14/451,250.
Notice of allowance dated Oct. 10, 2014 for U.S. Appl. No. 14/451,282.
Notice of allowance dated Oct. 14, 2014 for U.S. Appl. No. 14/451,273.
Notice of allowance dated Oct. 15, 2014 for U.S. Appl. No. 14/451,226.
Office action dated Jan. 5, 2009 for U.S. Appl. No. 11/286,448.
Office action dated Mar. 5, 2012 for U.S. Appl. No. 11/286,448.
Office action dated Mar. 7, 2012 for U.S. Appl. No. 12/959,321.
Office action dated Mar. 16, 2015 for U.S. Appl. No. 14/591,687.
Office action dated Mar. 16, 2015 for U.S. Appl. No. 14/591,707.
Office action dated Mar. 17, 2015 for U.S. Appl. No. 14/591,641.
Office action dated Mar. 20, 2015 for U.S. Appl. No. 14/523,688.
Office action dated Mar. 24, 2015 for U.S. Appl. No. 14/523,477.
Office action dated Mar. 24, 2015 for U.S. Appl. No. 14/523,565.
Office action dated Mar. 24, 2015 for U.S. Appl. No. 14/523,607.
Office action dated Mar. 27, 2015 for U.S. Appl. No. 14/523,535.
Office action dated Mar. 29, 2011 for U.S. Appl. No. 11/286,448.
Office action dated Mar. 31, 2015 for U.S. Appl. No. 14/523,589.
Office action dated Apr. 1, 2015 for U.S. Appl. No. 14/523,674.
Office action dated Apr. 3, 2015 for U.S. Appl. No. 14/591,662.
Office action dated Apr. 15, 2013 for U.S. Appl. No. 12/840,132.
Office action dated Apr. 16, 2013 for U.S. Appl. No. 13/756,275.
Office action dated Apr. 29, 2013 for U.S. Appl. No. 12/959,321.
Office action dated May 7, 2012 for U.S. Appl. No. 12/959,321.
Office action dated May 20, 2014 for U.S. Appl. No. 13/958,153.
Office action dated Jun. 10, 2015 for U.S. Appl. No. 14/267,597.
Office action dated Jul. 13, 2012 for U.S. Appl. No. 12/840,132.
Office action dated Jul. 22, 2010 for U.S. Appl. No. 11/286,448.
Office action dated Aug. 7, 2013 for U.S. Appl. No. 12/959,321.
Office Action dated Aug. 8, 2014 for U.S. Appl. No. 13/863,140.
Office action dated Sep. 16, 2009 for U.S. Appl. No. 11/286,448.
Office Action dated Sep. 22, 2014 for U.S. Appl. No. 14/328,440.
Office Action dated Sep. 22, 2014 for U.S. Appl. No. 14/451,226.
Office Action dated Sep. 22, 2014 for U.S. Appl. No. 14/451,242.
Office Action dated Sep. 22, 2014 for U.S. Appl. No. 14/451,250.
Office Action dated Sep. 22, 2014 for U.S. Appl. No. 14/451,273.
Office action dated Sep. 22, 2014 for U.S. Appl. No. 14/451,262.
Office Action dated Sep. 23, 2014 for U.S. Appl. No. 14/451,282.
Office action dated Oct. 2, 2015 for U.S. Appl. No. 14/052,507.
Office action dated Oct. 26, 2012 for U.S. Appl. No. 13/559,478.
Office action dated Nov. 20, 2013 for U.S. Appl. No. 13/958,153.
Office action dated Dec. 29, 2014 for U.S. Appl. No. 14/267,597.
Olanow, et al. Multicenter, openlabel, trial of sarizotan in Parkinson disease patients with levodopa-induced dyskinesias (the SPLEN-DID Study). Clin Neuropharmacol 2004;27:58-62.
Opposition by Adamas Pharmaceuticals, Inc. against the grant of European Patent 1509232 B1 in the name of H. Lundbeck A/S dated Aug. 19, 2009.
Pahwa, et al. Practice Parameter: treatment of Parkinson disease with motor fluctuations and dyskinesia (an evidence-based review): report of the Quality Standards Subcommittee of the American Academy of Neurology. Neurology. Apr. 11, 2006; 66(7):983-95.
Papa, et al. Levodopa-induced dyskinesias improved by a glutamate antagonist in Parkinsonian monkeys. Ann Neurol. May 1996;39(5):574-8.
Parkes, et al. Amantadine dosage in treatment of Parkinson's disease. The Lancet. 1970; 295:1130-1133.
Parkes, et al. Treatment of Parkinson's disease with amantadine and levodopa. A one-year study. Lancet. May 29, 1971;1(7709):1083-7.
Parsons et al.: 'Glutamate in CNS disorders as a target for drug development: an update', XP002908604 Retrieved from STN Database accession No. 131:13198 & Drug News Perspect. vol. 11, No. 9, 1998, pp. 523-569.
Parsons, et al. Memantine is a clinically well tolerated N-methyl-D-aspartate (NMDA) receptor antagonist—a review of preclinical data. Neuropharmacology, 38:735-767 (1999).
Pharmaceutical Dosage Forms: Tablets, Second Edition, Revised and Expanded, published by Marcel Dekker, Inc., edited by Lieberman, Lachman, and Schwartz. 1990; pp. 462-472.
Pharmacokinetics, Drugs and the Pharmaceutical Sciences, Gibaldi and Perrier Eds., vol. 1, (1975), pp. 101-102.
PK-Merz ® film-coated tablet, "Summary of Product Characteristics." 2003, p. 1-11.
Rajput, et al. New use for an old drug: amantadine benefits levodopa induced dyskiensias. Mov Disord 1998;13:851-854.
Rascol, et al. Idazoxan, an alpha-2 antagonist, and L-DOPA-induced dyskinesias in patients with Parkinson's disease. Mov Disord 2001;16:708-713.
Rausch, et al. Effects of L-deprenyl and amantadine in an MPTP-model of parkinsonism. J. Neural Transm. 1990; 32:269-275.
Reisberg, et al. Memantine in moderate-to-severe Alzheimer's disease, N. Eng. J. Med. 2003; 348(14):1333-1341.
Remington's The Science and Practice of Pharmacy, 21st Ed., pp. 944-945, 1179, 1199-1202 (2006).
Reply Declaration of Richard F. Bergstrom, Ph.D. Jul. 15, 2015, pp. 1-14.
Riederer, et al. Pharmacotoxic psychosis after memantine in Parkinson's disease. Lancet. 1991; 338:1022-1023.
Rollins., "Clinical Pharmacokinetics. Remington: The Practice and Science of Pharmacy, 20th Ed. (2000), Ch. 59, p. 1145-1155."
Ruzicka, et al. Amantadine infusion treatment of motor fluctuations and dyskinesias in Parkinson's disease. J Neural Trans 2000;102:1297-1306.
Sakai, Saori. How to Read or Understand a Prescription. Insomnia. Journal of Recipe 2008 7(2), p. 16-28 (with translation).
Sansom, L.R. Oral extended-release products. Aust. Prescr. 1999, 22:88-90.
Savery, F. Amantadine and a fixed combination of levodopa and carbidopa in the treatment of Parkinson's disease. Dis Nerv Syst. Aug. 1977;38(8):605-8.

(56) References Cited

OTHER PUBLICATIONS

Schmidt, et al. Excitatory amino acids and Parkinson's disease. Trends Neurosci. 1990; 13(2):46-47.
Schneider, et al. Effects of oral memantine administration on Parkinson symptoms. Results of a placebo-controlled multicenter study. Dtsch. Med. Wschr. 1984; 109(25):987-990. (in German with English abstract).
Schwab, et al. Amantadine in Parkinson's Disease Review of More Than Two Years' Experience. JAMA, vol. 222, No. 7, Nov. 13, 1972, p. 792-795.
Schwab, et al. Amantadine in the treatment of Parkinson's disease. JAMA. May 19, 1969;208(7):1168-70.
Shannon, et al. Amantadine and motor fluctuations in chronic Parkinson's disease. Clin Neuropharmacol. Dec. 1987;10(6):522-6.
Shefrin, SL. Therapeutic advances in idiopathic Parkinsonism. Expert Opin. Investig. Drugs. Oct. 1999; 8(10):1565-1588.
Siemers, E. Recent progress in the treatment of Parkinson's disease. Comprehensive Therapy. 1992; 18(9):20-24.
Silver, et al. Livedo reticularis in Parkinson's disease patients treated with amantadine hydrochloride. Neurology. Jul. 1972;22(7):665-9.
Silverman, R. The Organic Chemistry of Drug Design and Drug Action, published 1992 by Academic Press, pp. 19-21 and 352-397.
Snow, et al. The effect of amantadine on levodopa-induced dyskinesias in Parkinson's disease: a double-blind, placebo-controlled study. Clin Neuropharmacol. Mar.-Apr. 2000;23(2):82-5.
Spieker, et al. The NMDA antagonist budipine can alleviate levodopa-induced motor fluctuations. Mov. Disord. May 1999; 14(3):517-19.
Standaert, et al. Chapter 22: Treatment of central nervous system degenerative disorders. Goodman and Gilman's The Pharmacological Basis of Therapeutics 10th Ed., Hardman Limbird and Gilman Eds., McGraw-Hill, New York, 2001.
Stedman's Medical Dictionary. 27th ed. Lippincott, Williams and Wilkins. Baltimore 2000.
Sviridov, et al. C-hydroxyalkylation of N-adamantylanilines by hexafluoroacetone and methyl trifluoropyruvate. Izv. Akad. Nauk. SSSR, Ser. Khim. 1989; 10:2348-2350 (English translation).
Tal, M. A novel antioxidant alleviates heat hyperalgesia in rats with an experimental painful peripheral neuropathy. Neuroreport. May 31, 1996; 7(8):1382-84.
Tariot, et al. Memantine treatment in patients with moderate to severe Alzheimer disease already receiving donepezil: a randomized controlled trial. JAMA, 2004, 291(3):317-324.
Tempel, D. Memantine in the organic brain syndrome psycho. Therapiewoche. 1989;39:946-952 (with English summary).
Thanvi, et al. Long term motor complications of levodopa: clinical features, mechanisms, and management strategies. Postgrad Med J. Aug. 2004;80(946):452-8.
The Merck Manual of Diagnosis and Therapy, 17th Edition, published 1999 by Merck Research Laboratories, pp. 1393-1400.
Third Party Submission in Published Application Under 37 C.F.R. 1.99 dated Apr. 20, 2010 regarding U.S. Appl. No. 12/512,701, filed Jul. 30, 2009. 149 pgs.
Thomas, et al. Duration of amantadine benefit on dyskinesia of severe Parkinson's disease. J Neurol Neurosurg Psychiatry 2004;75:141-143.
Timmer, et al. Pharmacokinetic evaluation of gepirone immediate-release capsules and gepirone extended-release tablets in healthy volunteers. J Pharm Sci. Sep. 2003;92(9):1773-8.
Timmins, et al. Optimization and characterization of a pH-independent extended-release hydrophilic matrix tablet. Pharm Dev Technol. Feb. 1997;2(1):25-31.
Toutain, et al. Bioavailability and its assessment. J Vet Pharmacol Ther. Dec. 2004;27(6):455-66.
Troy, et al. Bioavailability of once-daily venlafaxine extended release compared with the immediate-release formulation in healthy adult volunteers. Current Therapeutic Research. Aug. 1997; 58(8):492-503.

Wolf, et al. Long-term antidyskinetic efficacy of amantadine in Parkinson's disease. Mov Disord. Published online Mar. 2, 2010. [Epub ahead of print].
Yamada, el at. Changes in symptoms and plasma homovanillic acid with amantadine hydrochloride in chronic schizophrenia. Biol. Psychiatry. May 15, 1997; 41(10):1062-64.
Ziemann, et al. Pharmacological control of facilitatory I-wave interaction in the human motor cortex. A paired transcranial magnetic stimulation study. Electroencephalogr. Clin. Neurophysiol. 1998;109(4):321-330.
U.S. Appl. No. 60/701857, filed Jul. 22, 2005.
Vale, et al. Amantadine in depression. Lancet. 1971; 11:437.
Vippagunta, et al. Crystalline Solids, Advanced Drug Delivery Reviews 48:3-26 (2001).
Vitale, et al. Unawareness of dyskinesias in Parkinson's and Huntington's diseases. Neurol Sci. Feb. 2001;22(1):105-6.
Walker, et al. A qualitative and quantitative evaluation of amantadine in the treatment of Parkinson's disease. J Chronic Dis. Mar. 1972;25(3):149-82.
Walker, et al. Amantadine and levodopa in the treatment of Parkinson's disease. Clin Pharmacol Ther. Jan.-Feb. 1972;13(1):28-36.
Walsh, et al. Parkinson's Disease and Anxiety. Postgraduate Medical Journal, Feb. 2001; 77:89-93.
Warren, et al. The use of amantadine in Parkinson's disease and other Akinetic-rigid disorders. ACNR 2004; 4(5):38-41.
Wessell, et al. NR2B selective NMDA receptor antagonist CP-101,606 prevents levodopa-induced motor response alterations in hemi-parkinsonian rats. Neuropharmacology. Aug. 2004; 47(2):184-94.
Wilkinson, GR. Chapter 1: Pharmacokinetics. Goodman and Gilman's The Pharmacological Basis of Therapeutics 10th Ed., Hardman Limbird and Gilman Eds., McGraw-Hill, New York, 2001.
Williams, et al. Calcium gradients in single smooth muscle cells revealed by the digital imaging microscope using Fura-2. Nature. 1985; 318:558-561.
Wimo, et al. Effect of long-term treatment with memantine, and nmda antagonist on costs associated with advanced Alzheimer's disease: results of a 28-week, randomized, double-blind, placebo-controlled study. Abstracts from the 8th International Conference on Alzheimer's Disease and Related Disorders. Stockholm, Sweden. Jul. 20-25, 2002. No. 167.
Wimo, et al. Pharmacoeconomics and dementia. Abstracts from the 8th International Conference on Alzheimer's Disease and Related Disorders. Stockholm, Sweden. Jul. 20-25, 2002. No. 541.
Co-pending U.S. Appl. No. 15/397,200, filed Jan. 3, 2017.
Co-pending U.S. Appl. No. 15/400,179, filed Jan. 6, 2017.
Co-pending U.S. Appl. No. 15/408,213, filed Jan. 17, 2017.
Co-pending U.S. Appl. No. 15/416,409, filed Jan. 26, 2017.
Co-pending U.S. Appl. No. 15/419,809, filed Jan. 30, 2017.
Co-pending U.S. Appl. No. 15/428,878, filed Feb. 9, 2017.
Co-pending U.S. Appl. No. 15/428,899, filed Feb. 9, 2017.
Co-pending U.S. Appl. No. 15/428,920, filed Feb. 9, 2017.
Co-pending U.S. Appl. No. 15/428,946, filed Feb. 9, 2017.
Wilson, et al. Combination drug regimens hold great promise for Alzheimer treatment. Science Blog. Available at http://www.scienceblog.com/community/older/archives/K/5/pub5611.html. Accessed Jan. 29, 2010. Published Jul. 23, 2002.
Co-pending U.S. Appl. No. 15/429,053, filed Feb. 9, 2017.
Co-pending U.S. Appl. No. 15/429,057, filed Feb. 9, 2017.
Co-pending U.S. Appl. No. 15/430,084, filed Feb. 10, 2017.
Co-pending U.S. Appl. No. 15/432,866, filed Feb. 14, 2017.
European search report and search opinion dated Dec. 20, 2016 for EP Application No. 16176422.
MedLinePlus: Amantadine citation retrieved from https://www.nlm.nih.gov/medlineplus/druginfo/meds/a682064.html. Accessed Jan. 25, 2016. Published Sep. 1, 2010.
Office action dated Jan. 12, 2017 for U.S. Appl. No. 14/863,035.
Office action dated May 31, 2016 for U.S. Appl. No. 14/863,035.
Office action dated Jul. 1, 2016 for U.S. Appl. No. 14/857,509.
Office action dated Jul. 6, 2016 for U.S. Appl. No. 14/863,051.
Office action dated Jul. 18, 2016 for U.S. Appl. No. 14/863,002.
Office action dated Jul. 27, 2016 for U.S. Appl. No. 14/863,067.

(56) References Cited

OTHER PUBLICATIONS

Office action dated Aug. 1, 2016 for U.S. Appl. No. 14/865,773.
Office Action dated Aug. 15, 2016 for U.S. Appl. No. 14/856,398.
Office Action dated Aug. 18, 2016 for U.S. Appl. No. 14/865,830.
Office action dated Aug. 25, 2016 for U.S. Appl. No. 14/865,736.
Office action dated Nov. 28, 2016 for U.S. Appl. No. 14/856,406.
Paci, et al. Amantadine for dyskinesia in patients affected by severe Parkinson's disease. Neurological Sciences 22.1 (2001): 75-76.
Symmetrel. Amantadine hydrochloride. Retrieved from the Internet: URL—http://www.pbs.gov.au/meds%2Fpi%2Fnvpsymor10611.pdf (retrieved on Jul. 25, 2012). Published Jun. 29, 2011.
Co-pending U.S. Appl. No. 15/434,491, filed Feb. 16, 2017.
Adamas Pharmaceuticals, Inc. Press Release (2017). Adamas announces FDA approval of Gocovri™ as first and only medication for the treatment of dyskinesia in Parkinson's disease patients, 4 total pages.
Aoki et al. (1985). Amantadine kinetics in healthy elderly men: implications for influenza prevention. Clin. Pharmacol. Ther. 37:137-44.
Aoki et al. (1979) Amantadine kinetics in healthy young subjects after long-term dosing. Clin. Pharmacol. Ther. 26:729-36.
Applicant Initiated Interview Summary dated Jul. 13, 2017, for U.S. Appl. No. 15/430,084, filed Feb. 10, 2017, 2 pages.
Aricept® (2012). Highlights of prescribing information, 14 pages.
CT-Arzneimittel—Amantadine-CT 100 mg film coated tablets (2008). Summary of product characteristics, 19 pages (with English Translation).
Daugirdas, et al. Binding of amantadine to red blood cells. Ther Drug Monit. 1984;6(4):399-401.
Declaration of Gregory T. Went under 37 C.F.R § 1.132 in support of U.S. Appl. No. 15/428,878, filed Feb. 9, 2017, 111 pages.
Declaration of Peter LeWitt under 37 C.F.R § 1.132 in support of U.S. Appl. No. 15/428,878, filed Feb. 9, 2017, 155 pages.
Examiner Initiated Interview Summary dated Sep. 11, 2017, in U.S. Appl. No. 15/428,878, filed Feb. 9, 2017, 1 page.
Gocovri™ (2017). Highlights of prescribing information, 19 total pages.
Gralise (2011). Highlights of prescribing information, 24 total pages.
Guide to MS Medications, Multiple Sclerosis Society of Canada, 2004, pp. 1-75.
Hauser et al. (2000). A home diary to assess functional status in patients with parkinson's disease with motor fluctuations and dyskinesia, Clin. Neurolog. 23:75-81.
Morrison, D. et al. (2007). A randomized, crossover study to evaluate the pharmacokinetics of amantadine and oseltamlvlr administered alone and in combination, PLoS ONE 2(12):e1305.
Namenda XR (2010). Highlights of prescribing information, 21 total pages.
Neurontin® Product Information (2013). Parke-Davis, Pfizer, 37 pages.

Notice of Allowance and Fees Due dated Sep. 11, 2017, for U.S. Appl. No. 15/428,878, filed Feb. 9, 2017, 9 pages.
Non-Final Office Action dated May 19, 2017, for U.S. Appl. No. 15/428,878, filed Feb. 9, 2017, 16 pages.
Non-Final Office Action dated Jul. 19, 2017, for U.S. Appl. No. 15/428,899, filed Feb. 9, 2017, 18 pages.
Non-Final Office Action dated Jul. 13, 2017, for U.S. Appl. No. 15/430,084, filed Feb. 10, 2017, 18 pages.
Opposition by Dr. Gabriele Ahrens against the grant of European Patent 2 506 709 in the name of Adamas Pharmaceuticals, Inc. dated Apr. 20, 2017, 32 total pages.
Parkes, D. (1974). Amantadine. Adv. Drug. Res. 8:11-81.
Symmetrel® Product Information (2009). Endo Pharmaceuticals Inc., 15 pages.
U.S. Appl. No. 15/434,491, filed Mar. 16, 2017.
U.S. Appl. No. 15/460,787, filed Mar. 16, 2017.
U.S. Appl. No. 15/633,379, filed Jun. 26, 2017.
Covera-HS® Extended-Release Tablets Controlled-Onset Description (2011). 17 total pages.
Declaration of Gregory T. Went under 37 C.F.R § 1.132 in support of U.S. Appl. No. 15/428,980, filed Feb. 9, 2017, 111 pages.
Declaration of Peter LeWitt under 37 C.F.R § 1.132 in support of U.S. Appl. No. 15/428,980, filed Feb. 9, 2017, 171 pages.
Declaration of Gregory T. Went under 37 C.F.R § 1.132 in support of U.S. Appl. No. 15/428,899, filed Feb. 9, 2017, 111 pages.
Declaration of Peter LeWitt under 37 C.F.R § 1.132 in support of U.S. Appl. No. 15/428,899, filed Feb. 9, 2017, 85 pages.
Declaration of Gregory T. Went under 37 C.F.R § 1.132 in support of U.S. Appl. No. 15/430,084, filed Feb. 10, 2017, 111 pages.
Declaration of Peter LeWitt under 37 C.F.R § 1.132 in support of U.S. Appl. No. 15/430,084, filed Feb. 10, 2017, 84 pages.
Notice of Allowance dated Oct. 26, 2017, for U.S. Appl. No. 15/430,084, filed Feb. 10, 2017, 7 pages.
Pahwa et al. (2017). "ADS-5102 (Amantadine) Extended-Release Capsules for Levodopa-Induced Dyskinesia in Parkinson Disease (EASE LID Study): A Randomized Clinical Trial," *Jama Neurol.* 74:941-949.
Pahwa et al. (2015). "Amantadine extended release for levodopa-induced dyskinesia in Parkinson's disease (EASED Study)," *Mov. Disord.* 30:788-795.
Symmetrel Summary of Basis of Approval (1972). NDA 17-117 and NDA 17-118, 30 total pages.
Symmetrel, EXP-105-1 Medical Officer's Review of Revised Labeling, NDA 16-020 and NDA 16-023 (1979), 21 total pages.
Symmetrel NDA 16-020 and NDA 16-023 (1964). Amendments and Medical Review, 143 total pages.
Symmetrel (1982). Letter from FDA regarding Disclosable Reviews of Symmetrel, 49 total pages.
Symmetrel (1979). NDA 18-101, 52 total pages.
Symmetrel (1973). NDA 17-117, 69 total pages.
Woodburn et al. (1994). "Neuroprotective Actions of Excitatory Amino Acid Receptor Antagonists," in *Advances in Pharmacology*, vol. 30, pp. 1-21.

Dissolution Profiles of Amantadine ER Formulations

Simulation based on results of Adamas steady state PK study ADS-PD-104.

METHOD OF ADMINISTERING AMANTADINE PRIOR TO A SLEEP PERIOD

CROSS-REFERENCE

This application is a continuation of U.S. patent application Ser. No. 14/863,035, filed Sep. 23, 2015, which is a continuation of U.S. patent application Ser. No. 14/523,535, filed Oct. 24, 2014, now abandoned, which is a continuation of U.S. patent application Ser. No. 14/267,597, filed May 1, 2014, now abandoned, which is a continuation of U.S. patent application Ser. No. 12/959,321, filed Dec. 2, 2010, now U.S. Pat. No. 8,741,343, which claims benefit of U.S. Provisional Application No. 61/266,053, filed Dec. 2, 2009, all of which applications are incorporated herein by reference in their entirety.

BACKGROUND OF THE INVENTION

The field of the invention is extended release compositions of amantadine and uses thereof.

Amantadine is indicated for various conditions that can be treated by NMDA receptor antagonists including the treatment of idiopathic Parkinson's disease (Parlysis Agitans), postencephalitic Parkinsonism, and symptomatic Parkinsonism which may follow injury to the nervous system by carbon monoxide intoxication. Amantadine also has activity as a viral M2 channel inhibitor and is used for the prophylaxis and treatment of infection of viral diseases, especially influenza A virus.

Currently marketed forms of amantadine are immediate release formulations that are typically administered two or more times a day. Amantadine's use is limited by dose related CNS side effects including dizziness, confusion, hallucinations, insomnia and nightmares (Gracies J M, Olanow C W; Current and Experimental Therapeutics of Parkinson's Disease; *Neuropsychopharmacology: the Fifth Generation of Progress*, p. 1802; American College of Neuropsychopharmacology 2002), which can be particularly exacerbated when amantadine is administered at night.

It is known that immediate release amantadine can act as a stimulant, causing insomnia and sleep disturbance. Therefore, the last dose is typically administered no later than 4 pm in order to minimize these side effects. Such dosing of amantadine results in peak plasma amantadine concentrations occurring in the evening or night, and very low plasma concentrations in the morning.

Extended release forms of amantadine have been described in the art. U.S. Pat. No. 5,358,721, to Guittard et al., and U.S. Pat. No. 6,217,905, to Edgren et al., each disclose an oral osmotic dosage form comprising an antiviral or anti-Parkinson's drug, respectively, where in each case amantadine is listed as a possible drug to be utilized in the dosage form. U.S. Pat. No. 6,194,000, to Smith et al., discloses analgesic immediate and controlled release pharmaceutical compositions utilizing NMDA receptor antagonists, such as amantadine, as the active agent. U.S. Patent Appl. Publication Nos. US 2006/0252788, US 2006/0189694, US 2006/0142398, and US 2008/0227743, all to Went et al., each disclose the administration of an NMDA receptor antagonist, such as amantadine, optionally in controlled release form.

SUMMARY OF THE INVENTION

The inventors have identified a need in the art for improved formulations of amantadine that result in a patient having higher plasma concentrations of amantadine upon waking in the morning without adversely affecting sleep. Further, the inventors have identified a need in the art for a method of administering amantadine in the late afternoon or evening, e.g. after 4 pm, which reduces side effects of insomnia and sleep disturbance and provides effective plasma concentrations of amantadine upon waking.

Therefore, there exists a need in the art for improved methods of amantadine therapy which can be administered to a patient shortly before they wish to sleep (e.g., at bedtime) without causing insomnia or sleep disturbance. In addition, there is a need for an amantadine therapy which can be taken by the patient before they go to sleep and then provides a suitable plasma concentration of amantadine when they wake up, e.g. in the morning, after a full night's sleep.

In addition, many Parkinson's disease patients have difficulty swallowing and are on multiple medications. Hence there is a need for amantadine therapy that delivers a therapeutically effective dose of the drug, can be administered once daily and is in an oral dosage form that is small in size and does not unduly increase the pill burden.

One aspect of the invention is a method of administering amantadine to a patient in need thereof, said method comprising orally administering an extended release (ER) composition comprising amantadine, or a pharmaceutically acceptable salt thereof, less than three hours before bedtime (i.e. the time at which the subject wishes to go to sleep for the night). This aspect also includes the use of such compositions and the use of amantadine for the manufacture of a medicament as described below. Alternatively, the composition is administered less than about 4 hours before bedtime.

In a second aspect, the invention provides a method of reducing sleep disturbance in a human subject undergoing treatment with amantadine, said method comprising administering an extended release (ER) composition comprising amantadine, or a pharmaceutically acceptable salt thereof, less than about three hours before bedtime (i.e. the time at which the subject wishes to go to sleep for the night). This aspect also includes the use of such compositions and the use of amantadine for the manufacture of a medicament as described below. Alternatively, the composition is administered less than about 4 hours before bedtime.

In a third aspect, the invention provides a method of treating levodopa induced dyskinesia, or fatigue, or dementia, or any other symptom of Parkinson's disease, said method comprising administering an extended release (ER) composition comprising amantadine, or a pharmaceutically acceptable salt thereof, less than about three hours before bedtime (i.e. the time at which the subject wishes to go to sleep for the night). This aspect also includes the use of such compositions and the use of amantadine for the manufacture of a medicament as described below.

In a fourth aspect, the invention provides a method of treating brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, neuropsychiatric disorders, said method comprising administering an extended release (ER) composition comprising amantadine, or a pharmaceutically acceptable salt thereof, less than about three hours before bedtime (i.e. the time at which the subject wishes to go to sleep for the night). This aspect also includes the use of such compositions and the use of amantadine for the manufacture of a medicament as described below.

In one embodiment of any of the above aspects, administration occurs less than two and a half, less than two, less than one and a half, less than one or less than half hour before bedtime (i.e. the time at which the subject wishes to go to sleep for the night).

In one embodiment of any of the above aspects the patient has been diagnosed with Parkinson's disease.

In one embodiment of any of the above aspects, the composition is administered once daily. In another aspect, the daily dose exceeds 200 mg, and is given in 1, 2 or 3 capsules of size 0, 1 or 2.

In one embodiment of any of the above aspects, administration of the composition to a Parkinson's disease patients results in a significant reduction in levodopa induced dyskinesia (LID). In a specific embodiment, administration of the composition results in about 5%, 10%, 15%, 20%, 25%, 30%, 35%, 40%, 45%, 50%, 55%, 60%, 65%, 70%, 75% or 80% reduction in levodopa induced dyskinesia. In further embodiments, the reduction in levodopa induced dyskinesia is measured on a numeric scale that is used by the FDA to evaluate effectiveness of drugs indicated to reduce LID. In further specific embodiments, the scale used in measuring the reduction in LID could be UDysRS, UPDRS Part IV (subscores 32, 33), Dyskinesia Rating Scale (DRS), Abnormal Involuntary Movement Scale (AIMS), or other scales developed for this purpose.

In one embodiment of any of the above aspects, administration of the composition to a Parkinson's disease patients results in a significant reduction in Parkinson's disease fatigue. In a specific embodiment, administration of the composition results in about 5%, 10%, 15%, 20%, 25%, 30%, 35%, 40%, 45%, 50%, 55% or 60% reduction in Parkinson's disease fatigue. In further specific embodiments, the reduction in fatigue is measured on a numeric scale that is used by the FDA to evaluate effectiveness of drugs indicated to reduce fatigue. In further specific embodiments, the scale used in measuring the reduction in fatigue could be the Fatigue Severity Scale (FSS).

In one embodiment of any of the above aspects, administration of the composition to a Parkinson's disease patients results in a significant reduction in Parkinson's disease symptoms. In a specific embodiment, administration of the composition results in about 5%, 10%, 15%, 20%, 25%, 30%, 35%, or 40% reduction in Parkinson's symptoms. In further specific embodiments, the reduction in Parkinson's symptoms is measured on a numeric scale that is used by the FDA to evaluate effectiveness of drugs indicated to reduce Parkinson's symptoms. In further specific embodiments, the scale used in measuring the reduction in Parkinson's symptoms could be the Unified Parkinson's Disease Rating Scale (UPDRS).

In one embodiment of any of the above aspects, the composition is added to food, and in a more specific embodiment to a small amount of soft food (e.g. applesauce or chocolate pudding), prior to administration. Addition to food may involve a capsule being opened and the contents sprinkled over the patient's food. This is advantageous if the patient is unable or unwilling to swallow the composition.

In one embodiment of any of the above aspects, there is no increase in plasma concentration of amantadine for at least one hour after the administration at steady state plasma concentrations.

In one embodiment of any of the above aspects, there is no increase in the plasma concentration of amantadine for at least two hours after the administration at steady state plasma concentrations.

In one embodiment of any of the above aspects, the administration of the composition to a human subject at steady state amantadine plasma concentrations increases the amantadine plasma concentration by less than 5%, 10%, 15%, 20% or 25% at 1, 2, 2.5 or 3 hours following such administration. For example, administration of the composition to a human subject at steady state amantadine plasma concentrations increases the amantadine plasma concentration by less than 5% at 1, 2, 2.5 or 3 hours following such administration; or by less than 10% at 1, 2, 2.5 or 3 hours following such administration; or by less than 15% at 1, 2, 2.5 or 3 hours following such administration; or by less than 20% at 1, 2, 2.5 or 3 hours following such administration; or by less than 25% at 1, 2, 2.5 or 3 hours following such administration.

In one embodiment of any of the above aspects the amantadine has a single dose Tmax of 9 to 15 hours. In a more specific embodiment, the amantadine has a single dose Tmax of 10 to 14 hours after administration. In another more specific embodiment, the amantadine has a single dose Tmax of 11 to 13 hours after administration.

In one embodiment of any of the above aspects the amantadine has a steady state Tmax of 7 to 13 hours. In a more specific embodiment, the amantadine has a steady state Tmax of 8 to 12 hours after administration. In another more specific embodiment, the amantadine has a steady state Tmax of 9 to 11 hours after administration.

In one embodiment of any of the above aspects peak plasma concentration of amantadine is achieved between 6 and 16 hours after administration of a single dose of the composition. In a more specific embodiment, peak amantadine plasma concentration is achieved 8 to 14 hours after administration of a single dose of the composition. In another more specific embodiment, peak amantadine plasma concentration is achieved 10 to 12 hours after administration of a single dose of the composition. In additional specific embodiments, peak amantadine plasma concentration is achieved between 6, 7, 8, 9, 10, 11 or 12 hours to about 9, 10, 11, 12, 13, 14, 15, 16, 17, 18, 19, 20, 21, 22, 23 or 24 hours after administration of a single dose of the composition.

In one embodiment of any of the above aspects, a once daily oral administration of the composition to a human subject provides a steady state plasma concentration profile characterized by a concentration increase of amantadine of less than 25% at three hours after the administration. In a more specific embodiment, the steady state plasma concentration profile is characterized by a concentration increase of amantadine of less than 25% at four hours after the administration.

In one embodiment of any of the above aspects, the composition is administered once a day and the ratio of Cmax to Cmin at steady state is 1.5 to 2.0, or, more specifically, 1.7 to 1.9, or, more specifically, about 1.8.

In one embodiment of any of the above aspects, the steady state plasma concentration profile following multiple administrations to a human subject of the composition at bedtime is characterized by an average plasma concentration during the day ("C-ave-day", defined as the average day time amantadine plasma concentration as measured in a human PK study) that is 1.1 to 2.0 times the average plasma concentration during the night ("C-ave-night", defined as the average night time amantadine plasma concentration as measured in a human PK study). In more specific embodiments the C-ave-day is the average amantadine plasma concentration as measured between the hours of 5 am, 6 am, 7 am, 8 am or 9 am to the hours of 4 pm, 5 pm, 6 pm, 7 pm or 8 pm; for example, between the hours of 6 am and 4 pm, between the hours of 7 am and 6 pm, or between the hours of 7 am and 5 pm. The C-ave-night is the average amantadine plasma concentration as measured between the hours of 4 pm, 5 pm, 6 pm, 7 pm, 8 pm, 9 pm, 10 pm or 11 pm to the hours of 5 am, 6 am, 7 am, 8 am or 9 am; for example, between the hours of 10 pm and 6 am, between the hours of 7 pm and 6 am, or between the hours of 8 pm and 6 am.

In one embodiment of any of the above aspects, the steady state plasma concentration profile following multiple administrations to a human subject of the composition at bedtime is characterized by an average plasma concentration during the morning ("C-ave-morning", defined as the average amantadine plasma concentration as measured in a human PK study during the morning hours) that is 1.1 to 2.0 times the average plasma concentration during the night. In one embodiment the C-ave-morning is the average amantadine plasma concentration as measured between the hours of 5 am, 6 am, 7 am, 8 am or 9 am to the hours of 11 am, 11:30 am, 12 pm, 12:30 pm or 1:00 pm; for example, between the hours of 5 am and 11 am, or between the hours of 7 am and 12 pm. More preferably, the ratio of C-ave-morning/C-ave-night at steady state is 1.2 to 1.6.

In one embodiment of any of the above aspects, the steady state plasma concentration profile following daily administration of the composition is characterized by an average plasma concentration during the period 8 hours to 12 hours after administration ("C-ave-8-12 hrs") that is 1.1 to 2.0 times the average plasma concentration during the first 8 hours after administration ("C-ave-0-8 hrs"). More preferably, the ratio of C-ave-8-12 hrs/C-ave-0-8 hrs at steady state is 1.2 to 1.6.

In one embodiment of any of the above aspects, administration of a single dose of the composition to a human subject provides a plasma concentration profile characterized by: a fractional AUC from 0 to 4 hours that is less than 5%, and preferably less than 3% of $AUC_{0-inf}$; a fractional AUC from 0 to 8 hours that is about 5 to 15%, and preferably about 8 to 12% of $AUC_{0-inf}$; a fractional AUC from 0 to 12 hours that is about 10 to 40%, and preferably about 15 to 30% of $AUC_{0-inf}$; a fractional AUC from 0 to 18 hours that is about 25 to 60%, and preferably about 30 to 50% of $AUC_{0-inf}$; and a fractional AUC from 0 to 24 hours that is about 40 to 75%, and preferably about 50 to 70% of $AUC_{0-inf}$.

In one embodiment of any of the above aspects, a once daily oral administration of the composition to a human subject provides a steady state plasma concentration profile characterized by: a fractional AUC from 0 to 4 hours that is about 2 to 25%, and preferably about 5 to 20% of $AUC_{24}$; a fractional AUC from 0 to 8 hours that is about 15 to 50%, and preferably about 20 to 40% of $AUC_{24}$; a fractional AUC from 0 to 12 hours that is about 30 to 70%, and preferably about 40 to 60% of $AUC_{24}$: and a fractional AUC from 0 to 18 hours that is about 60 to 95%, and preferably about 75 to 90% of $AUC_{24}$.

In one embodiment of any of the above aspects, a once daily oral administration of the composition to a human subject provides a steady state plasma concentration profile characterized by: a fractional AUC from 0 to 8 hours that is about 15 to 40%, and preferably about 20 to 32% of $AUC_{24}$; a fractional AUC from 8 to 16 hours that is about 30 to 50%, and preferably about 35 to 45% of $AUC_{24}$; and a fractional AUC from 16 to 24 hours that is about 20 to 35%, and preferably about 25 to 33% of $AUC_{24}$.

In one embodiment of any of the above aspects the amantadine is administered as a pharmaceutically acceptable salt. In a more specific embodiment, the amantadine is administered as hydrochloride or amantadine sulfate.

In one embodiment of any of the above aspects, a total daily dose of 50 mg to 600 mg of amantadine, or a pharmaceutically acceptable salt thereof is administered to a patient. More specifically the daily dose of amantadine or pharmaceutically acceptable salt thereof administered may be in the range of 100 to 440 mg. In another specific embodiment, the daily dose of amantadine or pharmaceutically acceptable salt thereof maybe in the range of 260 to 420 mg. In another embodiment, the daily dose of amantadine or pharmaceutically acceptable salt thereof administered exceeds 300 mg per day. In various specific embodiments, the daily dose of amantadine or pharmaceutically acceptable salt thereof may be 50 to 75 mg, 70 to 95 mg, 90 to 115 mg, 110 to 135 mg, 130 to 155 mg, 150 to 175 mg, 170 to 195 mg, 190 to 215 mg, 210 to 235 mg, 230 to 255 mg, 250 to 275 mg, 270 to 295 mg, 290 to 305 mg, 300 to 315 mg, 310 to 325 mg, 320 to 335 mg, 330 to 345 mg, 340 to 355 mg, 350 to 365 mg, 360 to 375 mg, 370 to 385 mg, 380 to 395 mg, 390 to 405 mg, 400 to 415 mg, 410 to 425 mg, 420 to 435 mg, 430 to 445 mg or 440 to 455 mg.

In one embodiment of any of the above aspects, the composition comprises 50 mg to 600 mg of amantadine, or a pharmaceutically acceptable salt thereof. More specifically, the composition may comprise 100 mg to 450 mg of amantadine, or a pharmaceutically acceptable salt thereof. Still more specifically, the composition may comprise 130-210 mg of amantadine, or a pharmaceutically acceptable salt thereof. In various specific embodiments, a dosage form containing the composition comprises 50 to 75 mg, 70 to 95 mg, 90 to 115 mg, 110 to 135 mg, 130 to 155 mg, 150 to 175 mg, 170 to 195 mg, 190 to 215 mg, 210 to 235 mg, 230 to 255 mg, 250 to 275 mg, 270 to 295 mg, 290 to 305 mg, 300 to 315 mg, 310 to 325 mg, 320 to 335 mg, 330 to 345 mg, 340 to 355 mg, 350 to 365 mg, 360 to 375 mg, 370 to 385 mg, 380 to 395 mg, 390 to 405 mg, 400 to 415 mg, 410 to 425 mg, 420 to 435 mg, 430 to 445 mg or 440 to 455 mg of amantadine, or a pharmaceutically acceptable salt thereof. In a more specific embodiment, the composition comprises about 110, 120, 130, 140, 150, 160 170, 180, 190, 210, or 220 mg amantadine, or a pharmaceutically acceptable salt thereof. In another more specific embodiment, the composition comprises 110 mg amantadine hydrochloride. In another more specific embodiment, the composition comprises 130 mg amantadine hydrochloride. In another more specific embodiment, the composition comprises 170 mg amantadine hydrochloride. In another more specific embodiment, the composition comprises 210 mg amantadine hydrochloride.

In one embodiment of any of the above aspects, the composition is administered as one, two, three or four unit dosage forms each comprising 100 to 175 mg amantadine, or a pharmaceutically acceptable salt thereof. In a more specific embodiment, the composition is administered as two unit dosage forms each comprising 100 to 175 mg amantadine, or a pharmaceutically acceptable salt thereof.

In one embodiment of any of the above aspects, the composition is administered as one, two, or three unit dosage forms each comprising 50 to 250 mg amantadine, or a pharmaceutically acceptable salt thereof. In a more specific embodiment, the composition is administered as one or two unit dosage forms each comprising 65 to 220 mg amantadine, or a pharmaceutically acceptable salt thereof.

In one embodiment of any of the above aspects, oral administration of a single dose of the composition to a human subject in a fasted state provides a maximum plasma concentration (Cmax) of 1.0 to 2.8 ng/ml per mg of amantadine. In a more specific embodiment, oral administration of a single dose of the composition to a human subject in a fasted state provides a maximum plasma concentration (Cmax) of 1.6 to 2.4 ng/ml per mg of amantadine and an $AUC_{0\text{-}inf}$ (Area under the concentration-curve curve from t=0 to t=infinity) of 40 to 75 ng*h/mL per mg of amantadine.

In one embodiment of any of the above aspects, the daily oral administration of a dose of the composition to a human subject provides a steady state plasma concentration profile characterized by at least one of: (i) a Cmax of 2.4 to 4.2 ng/ml per mg of amantadine, (ii) a Cmin of 1.1 to 2.6 ng/ml per mg of amantadine, and (iii) an $AUC_{0\text{-}24}$ of 44 to 83 ng*h/mL per mg of amantadine. In a more specific example, all three criteria of (i), (ii) and (iii) are met.

In a more specific embodiment, the steady state plasma concentration profile is further characterized by: (iv) no increase in concentration of amantadine for at least one hour after the administration; and (v) Cmax/Cmin ratio of 1.5 to 2.0. In a more specific embodiment, both criteria of (iv) and (v) are met.

In another more specific embodiment, the steady state plasma concentration profile is further characterized by at least one of: (iv) no increase in plasma concentration of amantadine for at least two hours after the administration; and (v) a Cmax/Cmin ratio of 1.7 to 1.9. In a more specific embodiment, both criteria of (iv) and (v) are met.

In one embodiment of any of the above aspects the composition has an in vitro dissolution profile of amantadine which shows at least one of (i) not more than 25% dissolution at 2 hours, (ii) not more 55-85% dissolution at 6 hours, and (iii) at least 80% dissolution at 12 hours, using a USP Apparatus II (Paddles) at 50 rpm with 500 ml water at 37° C. as the dissolution medium. In a more specific embodiment two of criteria (i), (ii) and (iii) are met. In a more specific embodiment, all three of criteria (i), (ii) and (iii) are met.

In one embodiment of any of the above aspects the composition has an in vitro dissolution profile of amantadine which shows at least one of (i) not more than 25% dissolution at 2 hours, (ii) not more than 25-55% dissolution at 6 hours, and (iii) at least 80% dissolution at 12 hours, using a USP Apparatus II (Paddles) at 50 rpm with 500 ml water at 37° C. as the dissolution medium. In a more specific embodiment two of criteria (i), (ii) and (iii) are met. In a more specific embodiment, all three of criteria (i), (ii) and (iii) are met.

In one embodiment of any of the above aspects the composition has an in vitro dissolution profile of amantadine which shows at least one of (i) not more than 20% dissolution at 1 hour, (ii) about 25-45% dissolution at 2 hours, (iii) not more than 50-80% dissolution at 4 hours, and (iv) at least 80% dissolution at 8 hours, using a USP Apparatus II (Paddles) at 50 rpm with 500 ml water at 37° C. as the dissolution medium. In a more specific embodiment two of criteria (i), (ii), (iii) and (iv) are met. In a more specific embodiment, all four of criteria (i), (ii), (iii) and (iv) are met.

In one embodiment of any of the above aspects the in vitro dissolution profile of amantadine is further characterized by release of amantadine of: (i) not more than 10% at 1 hour, or (ii) 30-50% at 4 hours, or (iii) at least 90% at 12 hours using a USP Apparatus II (Paddles) at 50 rpm with 500 ml water at 37° C. as the dissolution medium. In a more specific embodiment two of criteria (i), (ii) and (iii) are met. In a more specific embodiment, all three criteria of (i), (ii) and (iii) are met.

In another aspect, the present invention provides a pharmaceutical composition comprising or consisting of a pellet-in-capsule, wherein a pellet comprises a core that comprises a core seed with a mixture of amantadine and a binder coated onto the core seed, and an extended release coating surrounding the core comprising ethyl cellulose, a pore forming agent such as hydroxypropyl methyl cellulose or povidone, and a plasticizer.

In another aspect, the present invention provides a pharmaceutical composition for use in the methods of the aspects described above, wherein said composition is for oral administration and comprises a capsule for oral administration, said capsule comprising a plurality of pellets, each pellet comprising: (a) a pellet core comprising amantadine, or a pharmaceutically acceptable salt thereof, and (b) an extended release coating surrounding the pellet core.

In one embodiment, the extended release coating comprises ethyl cellulose and at least one of povidone and hydroxypropyl methyl cellulose, and a plasticizer. In a more specific embodiment, the extended release coating comprises ethyl cellulose, povidone, and a plasticizer.

In one embodiment, the pellet core comprises amantadine and a binder coated onto a core seed. In one embodiment, the core seed is a sugar sphere (nonpareil) or microcrystalline cellulose seed (e.g. Celphere®). In a more specific embodiment, the core seed is a microcrystalline cellulose core. In another specific embodiment, the core seed has a diameter in the range of 100 microns to 1,000 microns. In additional specific embodiments, the core seed has a diameter of 100, 200, 300, 400, 500, 600 or 700 microns. In preferred specific embodiments, the core seed has a diameter of less than 500 microns.

In one embodiment, based on the combined weight of the pellet core and extended release coating, the amantadine, or a pharmaceutically acceptable salt thereof, is present in amounts from 20 to 80 wt %, with a bulk density of 0.3 to 1.2 g/cm³.

In one embodiment, based on the combined weight of the pellet core and extended release coating, the amantadine, or a pharmaceutically acceptable salt thereof, is present in amounts from 40 to 60 wt %, with a bulk density of 0.5 to 1.2 g/cm³.

In one embodiment, based on the combined weight of the pellet core and extended release coating, the amantadine, or a pharmaceutically acceptable salt thereof, is present in amounts from 60 to 80 wt %, with a bulk density of 0.5 to 1.2 g/cm³.

In one embodiment, based on the combined weight of the pellet core and extended release coating, the binder is present in amounts from 8 to 25 wt %.

In one embodiment, based on the combined weight of the pellet core and extended release coating, the core seed is present in amounts from 8 to 25 wt %.

In one embodiment, based on the combined weight of the pellet core and extended release coating, the ethyl cellulose is present in amounts from 10 to 20 wt %.

In one embodiment, based on the combined weight of the pellet core and extended release coating, the povidone is present in amounts from 1 to 4 wt %.

In one embodiment, based on the combined weight of the pellet core and extended release coating, and the plasticizer is present in amounts from 1 to 4 wt %.

In one embodiment, the coated pellet has a diameter in the range of 200 microns to 1700 micros. In additional specific embodiments, the coated pellet has a diameter of 200, 300, 400, 500, 600, 700, 800, 900, 1000, 1100, 1200, 1300 or 1500 microns. In certain specific embodiments, the coated pellet has a diameter of less than 1000 microns, e.g., from 500 to 1000 microns.

In one embodiment, based on the combined weight of the pellet core and extended release coating, the binder is present in amounts from 5 to 25 wt %.

In one embodiment, based on the combined weight of the pellet core and extended release coating, the core seed is present in amounts from 1 to 15 wt %.

In one embodiment, based on the combined weight of the pellet core and extended release coating, the ethyl cellulose is present in amounts from 5 to 20 wt %.

In one embodiment, based on the combined weight of the pellet core and extended release coating, the povidone is present in amounts from 0.25 to 4 wt %.

In one embodiment, based on the combined weight of the pellet core and extended release coating, and the plasticizer is present in amounts from 0.25 to 4 wt %.

In one embodiment, the pellet further comprises a seal coating between the pellet core and the extended release coating. In some embodiments, an inert coating can be applied to the inert core prior to drug coating or on drug-coated pellets or on controlled release coated pellets. In another embodiment, an enteric coating can be applied to the drug coated pellets or controlled release pellets.

In one embodiment, the pellet core comprises a binder, selected from the group consisting of hydroxypropyl methyl cellulose, copovidone, and mixtures thereof.

In one embodiment, the above composition is provided in a size 3, size 2, size 1, size 0 or size 00 capsule.

In one embodiment, the therapeutically effective daily dose of the above composition is administered in no more than two capsules. In another embodiment, the therapeutically effective daily dose of the composition is administered in no more than three size 1 capsules. In another embodiment, the therapeutically effective daily dose of the composition is administered in no more than two size 0 capsules. In a still more preferred embodiment, the therapeutically effective daily dose of the composition is administered in no more than two size 1 capsules. In another embodiment, the therapeutically effective daily dose of the composition is administered in no more than three size 2 capsules.

In a preferred embodiment, the above composition is provided in an amount of 50 to 110 mg of amantadine or a pharmaceutically acceptable salt thereof in a size 2 capsule, and in the amount of 110 mg to 210 mg of amantadine or a pharmaceutically acceptable salt thereof in a size 1 capsule. In additional embodiments, the above composition comprises coated pellets of diameter 300 to 1000 microns, with amantadine or pharmaceutically acceptable salt thereof content of 40-80% wt % and at a bulk density of 0.5-1.2 g/cm$^3$. In a further preferred embodiment, the above composition has an in vitro dissolution profile of amantadine which shows at least one of (i) not more than 25% dissolution at 2 hours, (ii) not more than 55-85% dissolution at 6 hours, and (iii) at least 80% dissolution at 12 hours, using a USP Apparatus II (Paddles) at 50 rpm with 500 ml water at 37° C. as the dissolution medium. In a more specific embodiment two of criteria (i), (ii) and (iii) are met. In a more specific embodiment, all three of criteria (i), (ii) and (iii) are met.

In one embodiment, the plasticizer is selected from the group consisting of medium chain triglycerides, diethyl phthalate, citrate esters, polyethylene glycol, glycerol, acetylated glycerides, and castor oil. In a more specific embodiment, the plasticizer is medium chain triglycerides, e.g. Miglyol 812 N.

In another aspect, the present invention provides method of administering amantadine, or a pharmaceutically acceptable salt thereof, to a human subject in need thereof, said method comprising orally administering a composition of any of the above aspects.

In another aspect, the present invention provides a method of treating Parkinson's disease in a human subject in need thereof, said method comprising orally administering a composition of any of the above aspects. In a preferred aspect, the present invention provides a method of treating disease in a human subject in need thereof, said method comprising orally administering a composition of any of the above aspects once daily at nighttime, administering 1, 2 or 3 capsules.

References to administering amantadine to a subject in need thereof include treating a patient with a disease or condition which may be treated, prevented or cured by a NMDA antagonist. More specifically, administering amantadine to a subject in need thereof includes treating a patient with Parkinson's Disease, brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, neuropsychiatric disorders.

DETAILED DESCRIPTION OF THE INVENTION

Figure 1:
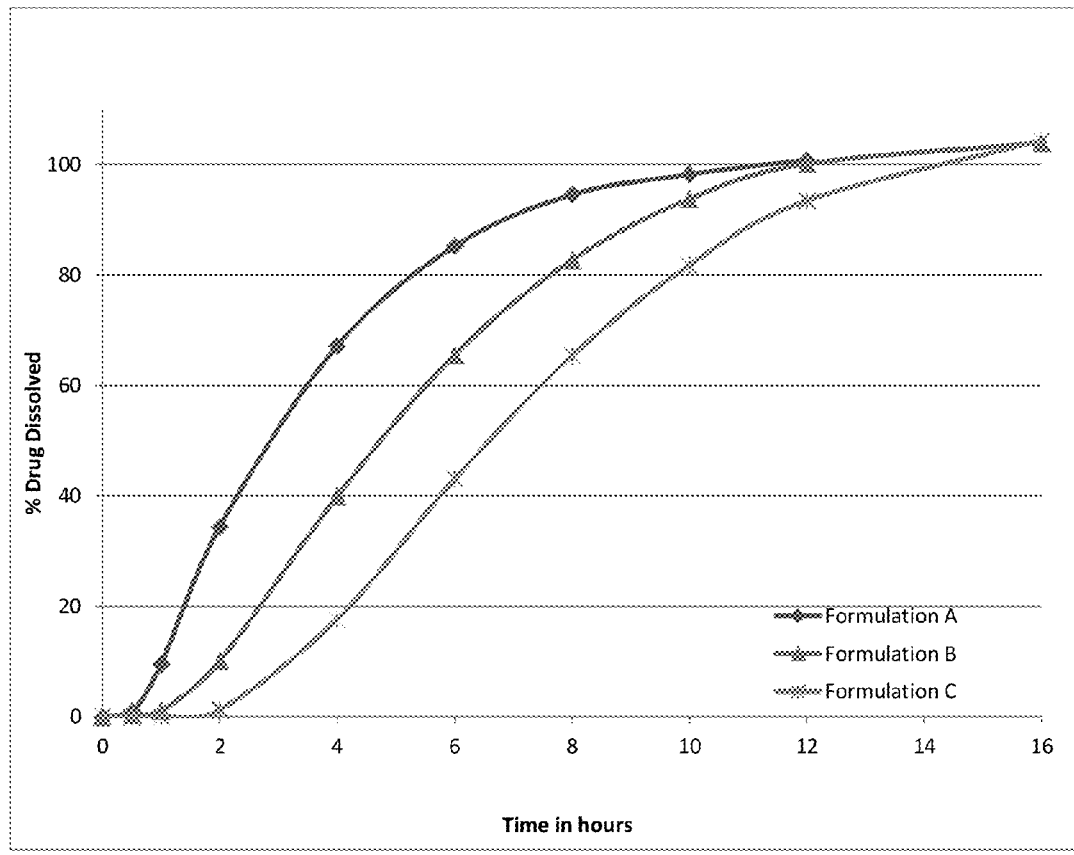
FIG. 1 shows the dissolution profiles for three amantadine ER formulations, A, B, C referred to in Example 3.

The invention provides a method of reducing sleep disturbances in a patient undergoing treatment with amantadine. The method comprises administering amantadine to a patient in need thereof, such that the amantadine does not interfere with sleep, yet provides maximum benefit in morning hours when often needed most by many patients who take amantadine and further, provides nighttime coverage of symptoms of Parkinson's disease if needed. Nighttime coverage includes providing benefit if the patient wakes up and wishes to return to sleep.

The method of the invention comprises orally administering to the patient an extended release (ER) amantadine composition designed for nighttime administration. The composition is taken less than three hours before bedtime, and preferably less than two and a half, less than two, less than one and a half, or less than one hour before bedtime. Most preferably the ER amantadine composition is taken less than half hour before bedtime (i.e. the time at which the subject wishes to go to sleep for the night). As used herein, a reference to amantadine is intended to encompass pharmaceutically acceptable salts thereof (e.g. amantadine hydrochloride, amantadine sulfate, etc.). Alternatively, the composition is administered less than about 4 hours before bedtime.

As used herein, "extended release" includes "controlled release", "modified release", "sustained release", "timed release", "delayed release", and also mixtures of delayed release, immediate release, enteric coated, etc. with each of the above.

The patient may be diagnosed with any disease or disorder for which amantadine is prescribed, such as Parkinson's disease, multiple sclerosis, drug-induced extrapyramidal reactions, levodopa-induced dyskinesia, and viral diseases (e.g. influenza, HBV, and HCV). In a specific embodiment, the patient has Parkinson's disease, which, as used herein, also encompasses a diagnosis of parkinsonism. In one embodiment, the patient has early stage Parkinson's disease, and the amantadine is used as a monotherapy or in combination with a monoamine oxidase type B (MAO-B) inhibitor without concomitant use of levodopa. In another embodiment, the patient has late stage Parkinson's disease and the patient takes levodopa in addition to the amantadine. In another embodiment, the patient has multiple sclerosis and the amantadine is used for the treatment of fatigue. In other embodiments, the patient has a brain injury, brain injury, brain trauma, dementia, Alzheimer's disease, stroke, Huntington's disease, ALS, Multiple Sclerosis, neurodegenerative diseases, dementias, cerebrovascular conditions, movement disorders, cranial nerve disorders, neuropsychiatric disorders.

An ER amantadine composition for use in the invention is adapted for nighttime administration by providing a plasma concentration profile that does not interfere with the subject's sleep. The composition of the invention will, upon administration to a human subject, result in a gradual initial increase in plasma concentration of amantadine such that, at steady state conditions, administration of a dose of the composition results in an increase in plasma concentration of amantadine of less than 25% at three hours after the dose is administered. For example, if a subject's steady state plasma concentration of amantadine is 500 ng/ml at the time a dose of the composition is administered, three hours later the subject's plasma concentration of amantadine will be less than 625 ng/ml. Preferably, the increase in plasma concentration of amantadine is less than 15%, and most preferably, less than 10%. Particularly preferred compositions have a plasma concentration profile further characterized by no increase in amantadine plasma concentration, or even a decrease (at steady state conditions), for at least one or, in a preferred embodiment, two hours after the administration. The composition for use in the invention is further adapted for bedtime (i.e. the time at which the subject wishes to go to sleep for the night) administration by providing a maximum concentration of amantadine (Cmax) in the morning hours. The time to reach Cmax (Tmax), as measured after single dose administration in the fasted state, is at least, 8 hours and up to 13, 14, 15, or 16 hours, or at least 9 hours and up to 13, 14, 15, or 16 hours, or at least 10 hours, and up to 13, 14, 15, or 16 hours. In specific embodiments, the Tmax is 9 to 15 hours, preferably 10 to 14 hours, and most preferably 11 to 13 hours. At steady state, with once daily administration of the composition, the Tmax is 7 to 13 hours, preferably 8 to 12 hours, and most preferably 9 to 11 hours. A suitable ER amantadine composition may be further characterized by having a steady-state Cmax/Cmin ratio of 1.5 to 2.0, and preferably 1.7 to 1.9, resulting in a composition with optimal fluctuation.

In more specific, preferred embodiments, the plasma concentration profile is further characterized by having an AUC profile after administration of a single dose of the composition characterized by: a fractional AUC from 0 to 4 hours that is less than 5%, and preferably less than 3% of $AUC_{0-inf}$; a fractional AUC from 0 to 8 hours that is about 5 to 15%, and preferably about 8 to 12% of $AUC_{0-inf}$; a fractional AUC from 0 to 12 hours that is about 10 to 40%, and preferably about 15 to 30% of $AUC_{0-inf}$; a fractional AUC from 0 to 18 hours that is about 25 to 60%, and preferably about 30 to 50% of $AUC_{0-inf}$; and a fractional AUC from 0 to 24 hours that is about 40 to 75%, and preferably about 50 to 70% of $AUC_{0-inf}$.

In a further preferred embodiment, the plasma concentration profile is further characterized by having an AUC profile after once daily dosing of the composition at steady state conditions characterized by: a fractional AUC from 0 to 4 hours that is about 2 to 25%, and preferably about 5 to 20% of $AUC_{24}$; a fractional AUC from 0 to 8 hours that is about 15 to 50%, and preferably about 20 to 40% of $AUC_{24}$; a fractional AUC from 0 to 12 hours that is about 30 to 70%, and preferably about 40 to 60% of $AUC_{24}$: and a fractional AUC from 0 to 18 hours that is about 60 to 95%, and preferably about 75 to 90% of $AUC_{24}$.

In some embodiments of any of the above aspects, the steady state plasma concentration profile following multiple administrations to a human subject of the composition at bedtime is characterized by an average plasma concentration during the day ("C-ave-day", defined as the average day time amantadine plasma concentration as measured in a human PK study) that is 1.1 to 2.0 times the average plasma concentration during the night ("C-ave-night", defined as the average night time amantadine plasma concentration as measured in a human PK study). In some embodiments, the ratio of C-ave-day/C-ave-night at steady state is within one of the ranges 1.1 to 1.9, 1.1 to 1.8, 1.1 to 1.7, 1.1 to 1.6, 1.1 to 1.5, 1.1 to 1.4, 1.2 to 1.9, 1.2 to 1.7, 1.2 to 1.6, 1.2 to 1.5, 1.3 to 1.9, 1.3 to 1.8, 1.3 to 1.7, 1.3 to 1.6, 1.4 to 1.9, 1.4 to 1.8, 1.4 to 1.7, 1.5 to 1.9, 1.5 to 1.8, 1.5 to 1.7, 1.6 to 1.9, 1.6 to 1.8 or 1.7 to 1.9. In some embodiments, the ratio of C-ave-day/C-ave-night at steady state is 1.1, 1.15, 1.2, 1.25, 1.3, 1.35, 1.4, 1.45, 1.5, 1.55, 1.6, 1.65, 1.7, 1.75, 1.8, 1.85, 1.9, 1.95, or 2.0. In some embodiments, the C-ave-day is the average amantadine plasma concentration as measured between the hours of 5 am, 6 am, 7 am, 8 am or 9 am to the hours of 4 pm, 5 pm, 6 pm, 7 pm or 8 pm and the C-ave-night is the average amantadine plasma concentration as measured between the hours of 4 pm, 5 pm, 6 pm, 7 pm, 8 pm, 9 pm, 10 pm or 11 pm to the hours of 5 am, 6 am, 7 am, 8 am or 9 am. In some embodiments, the C-ave-day is the average amantadine plasma concentration as measured within any four to twelve hour period between the hours of 5 am and 8 pm; and the C-ave-night is the average amantadine plasma concentration as measured within any four to twelve hour period between the hours of 8 pm and 5 am. In some embodiments, the C-ave-day is the average amantadine plasma concentration as measured within any four, five, six, seven, eight, nine, ten, eleven or twelve hour period between the hours of 5 am and 8 pm; and the C-ave-night is the average amantadine plasma concentration as measured within any four, five, six, seven, eight, nine, ten, eleven or twelve hour period between the hours of 8 pm and 5 am.

In some embodiments described herein an amantadine composition is administered to a patient from 0 to 4 hours prior to bedtime. In some embodiments, the amantadine composition is administered to a patient from 0 to 3, 0 to 2 or 0 to 1 hours prior to bedtime. In some embodiments, the amantadine composition is administered to a patient from 0 to 240 minutes, from 0 to 180 minutes, e.g. from 0 to 120 minutes, from 0 to 60 minutes, from 0 to 45 minutes, from 0 to 30 minutes, from 0 to 15 minutes or from 0 to 10 minutes prior to bedtime. In some embodiments, the amantadine composition is administered to a patient from 60 to 240 minutes, from 60 to 180 minutes, from 60 to 120 minutes or from 60 to 90 minutes prior to bedtime.

It is to be understood that administration to a patient includes administration by a healthcare professional and self administration by the patient.

Unless otherwise specified herein, the term "bedtime" has the normal meaning of a time when a person retires for the primary sleep period during a twenty-four hour period of time. While for the general populace, bedtime occurs at night, there are patients, such as those who work nights, for whom bedtime occurs during the day. Thus, in some embodiments, bedtime may be anytime during the day or night.

As used herein, unless otherwise indicated, reference to a plasma concentration profile or a specific pharmacokinetic property (e.g. Cmax, Cmin, AUC, Tmax, etc.) in a human subject refers to a mean value obtained from healthy adults s determined in a typical phase I clinical trial designed to measure pharmacokinetic properties of a drug (see e.g. Examples 5, 6 and 7, below). References herein to Tmax refer to values obtained after administration of a single dose at fasted states, unless otherwise indicated.

In some embodiments of the invention, the dose of the amantadine administered in accordance with the present invention is within or above the ranges normally prescribed for immediate release compositions of amantadine. In other embodiments, the doses of the amantadine administered with the present invention are higher than the ranges normally prescribed for immediate release compositions of amantadine. For example, the recommended dose of amantadine for the treatment of Parkinson's disease is 100 mg administered twice daily. In limited cases of the patient not deriving sufficient benefit at that dose and subject to the patient being able to tolerate such higher dose, the dose may be increased to 300 mg or 400 mg in divided doses. The most commonly prescribed doses of amantadine are 100 mg to 200 mg per day, with the latter administered in divided doses. More than 200 mg (for example 300 mg) is always given in divided doses. For the present invention, doses of 50 to 600 mg, or more preferably, 200 to 450 mg are administered for treatment of Parkinson's disease, and the methods and compositions of the invention may comprise administration of a dose as defined by any of these ranges. In specific embodiments the administration of such higher doses may be once daily. In additional embodiments the administration of such higher doses may be at night. In additional embodiments the administration of such higher doses may be in the form of 1, 2 or 3 capsules of size 0, 1 or 2 administered once daily.

In one embodiment of any of the above aspects the amantadine is administered as a pharmaceutically acceptable salt. In a more specific embodiment, the amantadine is administered as hydrochloride or amantadine sulfate.

In one embodiment of any of the above aspects, a total daily dose of 50 mg to 600 mg of amantadine, or a pharmaceutically acceptable salt thereof is administered to a patient. More specifically the daily dose of amantadine or pharmaceutically acceptable salt thereof administered may be in the range of 100 mg to 440 mg. In another specific embodiment, the daily dose of amantadine or pharmaceutically acceptable salt thereof maybe in the range of 260 mg to 420 mg. In another embodiment, the daily dose of amantadine or pharmaceutically acceptable salt thereof administered exceeds 300 mg per day. In various specific embodiments, the daily dose of amantadine or pharmaceutically acceptable salt thereof may be 50 to 75 mg, 70 to 95 mg, 90 to 115 mg, 110 to 135 mg, 130 to 155 mg, 150 to 175 mg, 170 to 195 mg, 190 to 215 mg, 210 to 235 mg, 230 to 255 mg, 250 to 275 mg, 270 to 295 mg, 290 to 305 mg, 300 to 315 mg, 310 to 325 mg, 320 to 335 mg, 330 to 345 mg, 340 to 355 mg, 350 to 365 mg, 360 to 375 mg, 370 to 385 mg, 380 to 395 mg, 390 to 405 mg, 400 to 415 mg, 410 to 425 mg, 420 to 435 mg, 430 to 445 mg or 440 to 455 mg.

In one embodiment of any of the above aspects, the composition comprises 50 to 600 mg of amantadine, or a pharmaceutically acceptable salt thereof. More specifically, the composition may comprise 100 to 450 mg of amantadine, or a pharmaceutically acceptable salt thereof. Still more specifically, the composition may comprise 130-210 mg of amantadine, or a pharmaceutically acceptable salt thereof. In various specific embodiments, the dosage form comprises 50 to 75 mg, 70 to 95 mg, 90 to 115 mg, 110 to 135 mg, 130 to 155 mg, 150 to 175 mg, 170 to 195 mg, 190 to 215 mg, 210 to 235 mg, 230 to 255 mg, 250 to 275 mg, 270 to 295 mg, 290 to 305 mg, 300 to 315 mg, 310 to 325 mg, 320 to 335 mg, 330 to 345 mg, 340 to 355 mg, 350 to 365 mg, 360 to 375 mg, 370 to 385 mg, 380 to 395 mg, 390 to 405 mg, 400 to 415 mg, 410 to 425 mg, 420 to 435 mg, 430 to 445 mg or 440 to 455 mg of amantadine, or a pharmaceutically acceptable salt thereof. In a more specific embodiment, the composition comprises about 110, 120, 130, 140, 150, 160 170, 180, 190, 210, or 220 mg amantadine, or a pharmaceutically acceptable salt thereof. In another more specific embodiment, the composition comprises 110 mg amantadine hydrochloride. In another more specific embodiment, the composition comprises 130 mg amantadine hydrochloride. In another more specific embodiment, the composition comprises 170 mg amantadine hydrochloride. In another more specific embodiment, the composition comprises 210 mg amantadine hydrochloride.

In one embodiment of any of the above aspects, the composition comprises from about 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg of amantadine, or a pharmaceutically acceptable salt thereof to about 75 mg, 85 mg, 95 mg, 105 mg, 115 mg, 125 mg, 135 mg, 145 mg, 155 mg, 165 mg, 175 mg, 185 mg, 195 mg, 205 mg, 215 mg, 225 mg, 235 mg, 245 mg, 255 mg, 265 mg, 275 mg, 285 mg, 295 mg, 305 mg, 315 mg, 325 mg, 335 mg, 345 mg, 355 mg, 365 mg, 375 mg, 385 mg, 395 mg, 405 mg, 415 mg, 425 mg, 435 mg, 445 mg of amantadine, or a pharmaceutically acceptable salt thereof.

In a specific embodiment of the invention, a subject's entire daily dose of amantadine is administered once, during a period of less than about three, two or one hours before bedtime (i.e. the time at which the subject wishes to go to sleep for the night). In other embodiments, at least one half of the daily dose of amantadine is taken during said period before bedtime. Preferably at least ⅔ of the dose of amantadine is taken in said period before bedtime, with the remainder taken in morning or afternoon. The morning or afternoon dose of the amantadine may be provided in a conventional, immediate release dosage form, or in an extended release form.

In one embodiment of any of the above aspects, administration of the composition to a Parkinson's disease patients results in a significant reduction in levodopa induced dyskinesia. In a specific embodiment, administration of the composition results in about 5%, 10%, 15%, 20%, 25%, 30%, 35%, 40%, 45%, 50%, 55%, 60%, 65%, 70%, 75% or 80% reduction in levodopa induced dyskinesia. In further embodiments, the reduction in levodopa induced dyskinesia is measured on a numeric scale that is used by or accepted by the FDA or other regulatory agencies to evaluate the effectiveness of and to approve for licensure drugs for the treatment of LID. In further specific embodiments, the scale used in measuring the reduction in LID could be UDysRS, UPDRS Part IV (subscores 32, 33), Dyskinesia Rating Scale (DRS), Abnormal Involuntary Movement Scale (AIMS), Rush Dyskinesia Rating Scale, Parkinson Disease Dyskinesia Scale (PDYS-26), Obeso Dyskinesia Rating Scale (CAPIT), Clinical Dyskinesia Rating Scale (CDRS), Lang-Fahn Activities of Daily Living Dyskinesia or other scales developed for this purpose.

In one embodiment of any of the above aspects, administration of the composition to a Parkinson's disease patients results in a significant reduction in Parkinson's disease fatigue. In a specific embodiment, administration of the composition results in about 5%, 10%, 15%, 20%, 25%, 30%, 35%, 40%, 45%, 50%, 55%, or 60% reduction in Parkinson's disease fatigue. In further specific embodiments, the reduction in fatigue is measured on a numerical scale used by or accepted by the FDA or other regulatory agencies to evaluate the effectiveness of and to approve for licensure drugs for the treatment of fatigue. In further specific embodiments, the scale used in measuring the reduction in fatigue could be the Fatigue Severity Scale (FSS), Fatigue Assessment Inventory, Functional Assessment of Chronic Illness Therapy-Fatigue (FACIT Fatigue), Multidimensional Fatigue Inventory (MFI-20), Parkinson Fatigue Scale (PFS-16) and the Fatigue Severity Inventory. In other specific embodiments, the reduction in fatigue is measured relative to placebo in a controlled clinical trial. In other embodiments, the reduction in fatigue is measured relative to baseline in a controlled clinical trial.

In one embodiment of any of the above aspects, administration of the composition to a Parkinson's disease patients results in a significant reduction in Parkinson's disease symptoms. In a specific embodiment, administration of the composition results in about 5%, 10%, 15%, 20%, 25%, 30%, 35%, or 40% reduction in Parkinson's symptoms. In further specific embodiments, the reduction in Parkinson's symptoms is measured on a numerical scale used by or accepted by the FDA or other regulatory agencies to evaluate the effectiveness of and to approve for licensure drugs for the treatment of Parkinson's symptoms. In further specific embodiments, the scale used in measuring the reduction in Parkinson's symptoms could be the Unified Parkinson's Disease Rating Scale (UPDRS). Unified Parkinson's Disease Rating Scale (UPDRS, MDS revision)—Part I: non-motor aspects of experiences of daily living (13 items), Part II: motor aspects of experiences of daily living (13 items)—Part III: motor examination (33 scored items)—Part I: mental status, behavior and mood—Part II: activities of daily living—Part III: motor examination (27 scored items) Hoehn and Yahr Staging Scale (Original or Modified).

In one embodiment of any of the above aspects, administration of the composition to a Parkinson's disease patients results in a significant reduction in levodopa induced dyskinesia. In a specific embodiment, administration of the composition results in about 5%, 10%, 15%, 20%, 25%, 30%, 35%, 40%, 45%, 50%, 55%, 60%, 65%, 70%, 75% or 80% reduction in levodopa induced dyskinesia. In further embodiments, the reduction in levodopa induced dyskinesia is measured on a numeric scale that is used by the FDA to evaluate effectiveness of drugs indicated to reduce LID. In further specific embodiments, the scale used in measuring the reduction in LID could be UDysRS, UPDRS Part IV (subscores 32, 33), Dyskinesia Rating Scale (DRS), Abnormal Involuntary Movement Scale (AIMS), or other scales developed for this purpose. In other specific embodiments, the reduction in LID is measured relative to placebo in a controlled clinical trial. In other embodiments, the reduction in LID is measured relative to baseline in a controlled clinical trial.

In one embodiment of any of the above aspects, administration of the composition to a Parkinson's disease patients results in a significant reduction in Parkinson's disease fatigue. In a specific embodiment, administration of the composition results in about 5%, 10%, 15%, 20%, 25%, 30%, 35%, or 40% reduction in Parkinson's disease fatigue. In further specific embodiments, the reduction fatigue is measured on a numeric scale that is used by the FDA to evaluate effectiveness of drugs indicated to reduce fatigue. In further specific embodiments, the scale used in measuring the reduction in fatigue could be the Fatigue Severity Scale (FSS). In other specific embodiments, the reduction in fatigue is measured relative to placebo in a controlled clinical trial. In other embodiments, the reduction in fatigue is measured relative to baseline in a controlled clinical trial.

In one embodiment of any of the above aspects, administration of the composition to a Parkinson's disease patients results in a significant reduction in Parkinson's disease symptoms. In a specific embodiment, administration of the composition results in about 5%, 10%, 15%, 20%, 25%, 30%, 35%, or 40% reduction in Parkinson's symptoms. In further specific embodiments, the reduction in Parkinson's symptoms is measured on a numeric scale that is used by the FDA to evaluate effectiveness of drugs indicated to reduce Parkinson's symptoms. In further specific embodiments, the scale used in measuring the reduction in Parkinson's symptoms could be the Unified Parkinson's Disease Rating Scale (UPDRS). In other specific embodiments, the reduction in Parkinson's disease symptoms is measured relative to placebo in a controlled clinical trial. In other embodiments, the reduction in Parkinson's disease symptoms is measured relative to baseline in a controlled clinical trial.

Extended Release Formulations

Extended release amantadine compositions suitable for use in the method of the invention can be made using a variety of extended release technologies, such as those described in the patent publications referenced in the above background section, which publications are incorporated herein by reference in their entireties. In some embodiments, the invention is a pellet in capsule dosage form. In some embodiments, the pellets comprise a pellet core, which is coated with at least one drug layer and at least one extended release coating layer. In some embodiments, the pellets are coated with at least one drug layer, an intermediate layer such as a seal coat and an extended release coating layer. In some embodiments, the pellet, the drug layer or both comprise one or more binders.

In some embodiments, the dosage unit comprises a plurality of coated pellets. In some embodiments, the pellets have a diameter of for example 300 to 1700 microns, in some cases 500 to 1200 microns. The pellets will comprise, for example, inert substrates, such as sugar spheres, microcrystalline cellulose (MCC) spheres, starch pellets. In some embodiments, pellets can be prepared by other processes such as pelletization, extrusion, spheronization, etc. or combinations thereof. The core pellets will comprise of amantadine hydrochloride and pharmaceutically acceptable excipients.

Coated Pellets

The pellet cores are coated with the active ingredient, e.g., amantadine or a pharmaceutically acceptable salt and/or polymorph thereof. In some embodiments, in addition to the active ingredient, the pellets also comprise one or more binders, such as for example hydroxypropyl methyl cellulose, copovidone, povidone, hydroxypropyl cellulose, hydroxyethyl cellulose, methyl cellulose, carboxymethyl cellulose etc. In some embodiments, the pellets also contain one or more additional excipients, such as anti-tack agents (e.g. talc, magnesium stearate etc.)

In some embodiments, the pellets cores are coated with a drug layer comprising active ingredient, and optionally one or more binders, anti-tack agents and/or solvents by conventional coating techniques such as fluidized bed coating, pan coating.

Intermediate Layer Coating

In some embodiments, the pellets are coated with an intermediate layer, such as a seal coat. In some embodiments, the seal coat is adapted to prevent ingredients in the extended release coating from interacting with ingredients in the pellet core, to prevent migration of the ingredients in the pellet core from diffusing out of the pellet core into the extended release layer, etc. As described herein, the seal coat of the present invention can comprise one or more film forming polymers including but not limited to hydroxypropylmethyl cellulose (HPMC), copovidone, povidone, polyvinyl pyrrolidone, hydroxypropyl cellulose, hydroxyethyl cellulose, methyl cellulose, carboxymethyl cellulose or any combination thereof and the like.

The seal coat can further comprise other additives like plasticizers, such as, propylene glycol, triacetin, polyethylene glycol, tributyl citrate and optionally anti-tacking agents, such as, magnesium stearate, calcium silicate, magnesium silicate, and colloidal silicon dioxide or talc.

Apart from plasticizers and anti-tacking agents as mentioned above, the seal coat can optionally contain buffers, colorants, opacifiers, surfactants or bases, which are known to those skilled in the art.

Seal coating can be applied to the core using conventional coating techniques such as fluidized bed coating, pan coating etc. In some embodiments, the drug coated pellets cores are coated with a seal coat layer that optionally comprises one or more binders, anti-tack agents and/or solvents by fluidized bed coating or pan coating.

Binders

In some embodiments, either the pellet cores, the intermediate coating layer, or both may comprise one or more binders (e.g., film forming polymers). Suitable binders for use herein include, e.g.: alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

Extended Release Coating

The pellets are coated with an extended release coating. The extended release coating is adapted to delay release of the drug from the coated drug cores for a period of time after introduction of the dosage form into the use environment. In some embodiments, the extended release coating includes one or more pH-dependent or non-pH-dependent extended release excipients. Examples of non-pH dependent extended release polymers include ethyl cellulose, hydroxypropylmethyl cellulose, hydroxyethyl cellulose, hydroxypropyl cellulose, carboxymethyl cellulose, copolymer of ethyl acrylate, methyl methacrylate (e.g. Eudgrait RS) etc. Examples of pH dependent extended release excipients include methacrylic acic copolymers, hydroxypropylmethyl cellulose acetate succinate, hydroxypropylmethyl cellulose phthalate, and cellulose acetate phthalate etc. The extended release coating may also include a pore former, such as povidone, polyethylene glycol, hydroxypropyl cellulose, hydroxypropylmethyl cellulose, etc., sugars such as sucrose, mannitol, lactose, and salts, such as sodium chloride, sodium citrate, etc., a plasticizer, such as acetylated citrated esters, acetylated glycerides, castor oil, citrate esters, dibutylsebacate, glyceryl monostearate, diethyl phthalate, glycerol, medium chain triglycerides, propylene glycol, polyethylene glycol. The extended release coating may also include one or more additional excipients, such as lubricants (e.g., magnesium stearate, talc etc.).

Extended release coating can be applied using conventional coating techniques such as fluidized bed coating, pan coating etc. The drug coated pellets cores, which optionally comprise a seal coat, are coated with the extended release coating by fluidized bed coating.

Extended Release Excipients (Coating Polymers)

As described herein, exemplary extended release excipients include, but are not limited to, insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkyl celluloses such as hydroxypropyl cellulose, hydroxypropylmethyl cellulose, sodium carboxymethyl cellulose, and cross-linked acrylic acid polymers like Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain embodiments, the plastic material can be a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain other embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In still other embodiments, the acrylic polymer is an acrylic resin lacquer such as that which is commercially available from Rohm Pharma under the trade name Eudragit®. In further embodiments, the acrylic polymer comprises a mixture of two acrylic resin lacquers commercially available from Rohm Pharma under the trade names Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit RL30D and 1:40 in Eudragit® RS30D. The mean molecular weight is about 150,000. Edragit® S-100 and Eudragit® L-100 are also suitable for use herein. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain an extended release formulation having a desirable dissolution profile. One skilled in the art will recognize that other acrylic polymers may also be used, such as, for example, Eudragit® L.

Pore Formers

In some embodiments, the extended release coating includes a pore former. Pore formers suitable for use in the extended release coating can be organic or inorganic agents, and include materials that can be dissolved, extracted or leached from the coating in the environment of use. Examples of pore formers include but are not limited to organic compounds such as mono-, oligo-, and polysaccharides including sucrose, glucose, fructose, mannitol, mannose, galactose, lactose, sorbitol, pullulan, dextran; polymers soluble in the environment of use such as water-soluble hydrophilic polymers, such as povidone, crospovidone, polyethylene glycol, hydroxypropyl cellulose, hydroxypropylmethyl cellulose, hydroxyalkyl celluloses, carboxyalkyl celluloses, cellulose ethers, acrylic resins, polyvinylpyrrolidone, cross-linked polyvinylpyrrolidone, polyethylene oxide, carbowaxes, Carbopol®, and the like, diols, polyols, polyhydric alcohols, polyalkylene glycols, polyethylene glycols, polypropylene glycols, or block polymers thereof, polyglycols, poly($\alpha$-$\Omega$) alkylenediols; inorganic compounds such as alkali metal salts, lithium carbonate, sodium chloride, sodium bromide, potassium chloride, potassium sulfate, potassium phosphate, sodium acetate, sodium citrate, suitable calcium salts, and the like. In certain embodiments, plasticizers can also be used as a pore former.

Capsules

The extended release pellets are introduced into a suitable capsule by using an encapsulator equipped with pellet dosing chamber. The capsule sizes may be 00, 0, 0EL, 1, 1EL, 2, 2EL, 3, 4 or 5. A particularly preferred composition that provides ideal pharmacokinetic properties and plasma concentration profiles is a pellet-in-capsule composition that comprises a plurality of pellets, typically having a diameter of about 500 µm to 1.2 mm, and preferably about 700 µm to 1000 µm, where each pellet comprises a core comprising amantadine and a binder, and an extended release coating surrounding the core that extends release of the amantadine so as to provide the desired pharmacokinetic properties and amantadine plasma concentration profiles described above.

In some embodiments, the pellets in the pellet-in-capsule are in a size 0 or smaller, preferably a size 1 or smaller capsule. Mean pellet diameters in some embodiments may be in a range of 500 µm to 1200 µm, e.g. from 500 µm to 1100 µm, from 500 µm to 1000 µm, from 500 µm to 900 µm, from 500 µm to 800 µm, from 500 µm to 700 µm, from 600 µm to 1100 µm, from 600 µm to 1000 µm, from 600 µm to 900 µm, from 600 µm to 800 µm, from 600 µm to 700 µm, from 700 µm to 1100 µm, from 700 µm to 1000 µm, from 700 µm to 900 µm, or from 700 µm to 800 µm. In some embodiments the mean particle diameters are, ±10%, e.g.: 500 µm, 550 µm, 600 µm, 650 µm, 700 µm, 750 µm, 800 µm, 850 µm, 900 µm, 950 µm, 1000 µm, 1050 µm, 1100 µm, 1150 µm or 1200 µm.

One preferred composition of the invention is a pellet-in-capsule composition wherein each pellet comprises a core that comprises a core seed with a mixture of amantadine and a binder coated onto the core seed, and an extended release coating surrounding the core comprising ethyl cellulose, a pore forming agent such as hydroxypropyl methyl cellulose or povidone, and a plasticizer. In some embodiments, the pellets may further comprise a seal coating between the pellet core and the extended release coating. The pellets are formulated using methods known in the art, such as those described in Example 1 below. In a specific embodiment, based on the combined weight of the pellet core and extended release coating, the amantadine is present in amounts from 20-80 wt %, 45-70 wt %, 40-50 wt %, 45-55 wt %, 50-60 wt %, 55-65 wt %, 60-70 wt %, 65-75 wt %, 70-80 wt %, or 40 to 60 wt %, the binder, which is preferably hydroxypropyl methyl cellulose, copovidone, or mixtures thereof, is present in amounts from 1 to 25 wt %, the core seed, preferably a sugar sphere (nonpareil) or microcrystalline cellulose seed (e.g. Celphere®), is present in amounts from 8 to 25 wt %, the ethyl cellulose is present in amounts from 10 to 20 wt %, the pore forming agent, preferably povidone, is present in amounts from 1 to 4 wt %, and the plasticizer is present in amounts from 1 to 4 wt %. In another specific embodiment, based on the combined weight of the pellet core and extended release coating, the amantadine is present in amounts from 50 to 70 wt %, the binder, which is preferably hydroxypropyl methyl cellulose, copovidone, or mixtures thereof, is present in amounts from 1 to 25 wt %, the core seed, preferably a sugar sphere (nonpareil) or microcrystalline cellulose seed (e.g. Celphere®), is present in amounts from 5 to 15 wt %, the ethyl cellulose is present in amounts from 1 to 15 wt %, the pore forming agent, preferably povidone, is present in amounts from 0.25 to 4 wt %, and the plasticizer is present in amounts from 0.25 to 4 wt %.

Additional embodiments of the invention are illustrated in the Table, below, entitled "Various Amantadine ER Capsule Size 1 Formulations". By means of methods and compositions described herein, formulations can be made that achieve the desired dissolution characteristics and target pharmacokinetic profiles described herein. More specifically, therapeutically effective doses of amantadine can be administered once daily in no more than two size 1 (or smaller, e.g. size 2 or 3) capsules using the manufacturing methods and compositions that have been described herein to achieve these results. In particular, higher drug loading can be achieved using compositions and manufacturing methods described herein. In some embodiments, higher drug loading may be achieved, with the required dissolution profile, using smaller core pellet sizes and concomitantly increased drug layering on smaller cores, but with no change in the extended release coat. In some embodiments, using alternative manufacturing approaches described herein, e.g. extrusion and spheronization, even higher drug loads can be achieved to realize the desired dissolution profile, enabling high amantadine drug loads with suitable pharmacokinetic profiles, resulting in compositions that are therapeutically more effective, and at least as well tolerated, and can be filled in relatively small sized capsules (e.g., size 1, 2 or 3), enabling ease of administration to patients.

from 30 to 55 wt %, from 30 to 52.5 wt %, from 30 to 50 wt %, from 30 to 47.5 wt %, from 30 to 45 wt %, from 30 to 42.5 wt %, from 30 to 40 wt %, from 40 to 80 wt %, from 40 to 77.5 wt %, from 40 to 75 wt %, from 40 to 72.5 wt %, from 40 to 70 wt %, from 40 to 67.5 wt %, from 40 to 65 wt %, from 40 to 62.5 wt %, from 40 to 60 wt %, from 40 to 57.5 wt %, from 40 to 55 wt %, from 40 to 52.5 wt %, from 40 to 50 wt %, from 40 to 47.5 wt %, from 40 to 45 wt %, from 50 to 80 wt %, from 50 to 77.5 wt %, from 50 to 75 wt %, from 50 to 72.5 wt %, from 50 to 70 wt %, from 50 to 67.5 wt %, from 50 to 65 wt %, from 50 to 62.5 wt %, from 50 to 60 wt %, from 50 to 57.5 wt %, from 50 to 55 wt %, from 60 to 80 wt %, from 60 to 77.5 wt %, from 60 to 75 wt %, from 60 to 72.5 wt %, from 60 to 70 wt %, from 60 to 67.5 wt %, from 60 to 65 wt %. In some embodiments, the bulk density is 0.3 to 1.2 g/cm$^3$, 0.3 to 1.15 g/cm$^3$, 0.3 to 1.1 g/cm$^3$, 0.3 to 1.05 g/cm$^3$, 0.3 to 1.0 g/cm$^3$, 0.3 to 0.9 g/cm$^3$, 0.3 to 0.8 g/cm$^3$, 0.3 to 0.7 g/cm$^3$, 0.3 to 0.6 g/cm$^3$, 0.3 to 0.5 g/cm$^3$, 0.3 to 0.4 g/cm$^3$, 0.4 to 1.2 g/cm$^3$, 0.4 to

TABLE

Various Amantadine ER Capsule Size 1 Formulations

| AMT Strength (mg) | Manufacture Method | Inert Core Pellet Size (mm) | Active Drug % w/w | Extended Release Coating % w/w | Bulk Density (g/cm$^3$) | % Fill in Size 1 Capsule | AMT Dissolution (%) (at T (hrs)): 2 hrs | 6 hrs | 12 hrs |
|---|---|---|---|---|---|---|---|---|---|
| 110 mg | Fluid bed coating | 0.3-0.5 | 40-50% | 10-30% | 0.6-1.0 | 60-70% | <25% | 40-80% | >80% |
| 140 mg | Fluid bed coating | 0.3-0.5 | 45-50% | 10-30% | 0.6-1.0 | 80-90% | <25% | 40-80% | >80% |
| 150 mg | Fluid bed coating | 0.3-0.5 | 50-55% | 10-30% | 0.6-1.0 | 80-90% | <25% | 40-80% | >80% |
| 170 mg | Fluid bed coating | 0.2-0.3 | 50-55% | 10-30% | 0.6-1.0 | 80-90% | <25% | 40-80% | >80% |
| 170 mg | Extrusion spheronization, pan or fluidized bed coating | N/A | 55-75% | 10-30% | 0.6-1.0 | 65-75% | <25% | | >80% |
| 190 mg | Extrusion spheronization, pan or fluidized bed coating | N/A | 55-75% | 10-30% | 0.6-1.0 | 75-85% | <25% | 40-80% | >80% |
| 210 mg | Extrusion spheronization, pan or fluidized bed coating | N/A | 55-75% | 10-30% | 0.6-1.0 | 80-90% | <25% | 40-80% | >80% |
| 230 mg | Extrusion spheronization, pan or fluidized bed coating | N/A | 55-75% | 10-30% | 0.6-1.0 | 85-95% | <25% | 40-80% | >80% |

In some embodiment, the amantadine, or a pharmaceutically acceptable salt thereof, is present in amounts from 20 to 80 wt % (based on the combined weight of the pellet core and extended release coating), with a bulk density of 0.3 to 1.2 g/cm$^3$. In some embodiments, the amantadine or pharmaceutically acceptable salt thereof is present in amounts from 20 to 77.5 wt %, from 20 to 75 wt %, from 20 to 72.5 wt %, from 20 to 70 wt %, from 20 to 67.5 wt %, from 20 to 65 wt %, from 20 to 62.5 wt %, from 20 to 60 wt %, from 20 to 57.5 wt %, from 20 to 55 wt %, from 20 to 52.5 wt %, from 20 to 50 wt %, from 20 to 47.5 wt %, from 20 to 45 wt %, from 20 to 42.5 wt %, from 20 to 40 wt %, from 20 to 37.5 wt %, from 20 to 35 wt %, from 20 to 32.5 wt %, from 20 to 30 wt %, from 30 to 80 wt %, from 30 to 77.5 wt %, from 30 to 75 wt %, from 30 to 72.5 wt %, from 30 to 70 wt %, from 30 to 67.5 wt %, from 30 to 65 wt %, from 30 to 62.5 wt %, from 30 to 60 wt %, from 30 to 57.5 wt %, 1.15 g/cm$^3$, 0.4 to 1.1 g/cm$^3$, 0.4 to 1.05 g/cm$^3$, 0.4 to 1.0 g/cm$^3$, 0.4 to 0.9 g/cm$^3$, 0.4 to 0.8 g/cm$^3$, 0.4 to 0.7 g/cm$^3$, 0.4 to 0.6 g/cm$^3$, 0.4 to 0.5 g/cm$^3$, 0.5 to 1.2 g/cm$^3$, 0.5 to 1.15 g/cm$^3$, 0.5 to 1.1 g/cm$^3$, 0.5 to 1.05 g/cm$^3$, 0.5 to 1.0 g/cm$^3$, 0.5 to 0.9 g/cm$^3$, 0.5 to 0.8 g/cm$^3$, 0.5 to 0.7 g/cm$^3$, 0.5 to 0.6 g/cm$^3$, 0.6 to 1.2 g/cm$^3$, 0.6 to 1.15 g/cm$^3$, 0.6 to 1.1 g/cm$^3$, 0.6 to 1.05 g/cm$^3$, 0.6 to 1.0 g/cm$^3$, 0.6 to 0.9 g/cm$^3$, 0.6 to 0.8 g/cm$^3$, 0.6 to 0.7 g/cm$^3$, 0.7 to 1.2 g/cm$^3$, 0.7 to 1.15 g/cm$^3$, 0.7 to 1.1 g/cm$^3$, 0.7 to 1.05 g/cm$^3$, 0.7 to 1.0 g/cm$^3$, 0.7 to 0.9 g/cm$^3$, 0.7 to 0.8 g/cm$^3$, 0.5 to 1.2 g/cm$^3$, 0.8 to 1.15 g/cm$^3$, 0.8 to 1.1 g/cm$^3$, 0.8 to 1.05 g/cm$^3$, 0.8 to 1.0 g/cm$^3$, 0.8 to 0.9 g/cm$^3$, 0.9 to 1.2 g/cm$^3$, 0.9 to 1.15 g/cm$^3$, 0.9 to 1.1 g/cm$^3$, 0.9 to 1.05 g/cm$^3$, or 0.9 to 1.0 g/cm$^3$. In some embodiments, the composition is in a dosage unit comprising a pellet in capsule formulation, wherein the capsule size is size 00, size 0, size 1, size 2 or size 3. In some preferred embodiments, the dosage unit includes pellets containing from 50 to 250 mg of amantadine in a size 0, 1, 2 or 3 capsule. In some embodiments, the dosage unit includes pellets containing from 100 to 250 mg, e.g. 100 to 200 mg of amantadine in a size 0, 1, 2 or 3 capsule, preferably a size 1, 2 or 3 capsule. In a more specific embodiment, the dosage unit comprises about 110, 120, 130, 140, 150, 160 170, 180, 190, 210, or 220 mg amantadine, or a pharmaceutically acceptable salt thereof. In another more specific embodiment, the dosage unit comprises 110 mg amantadine hydrochloride. In another more specific embodiment, the dosage unit comprises 130 mg amantadine hydrochloride. In another more specific embodiment, the dosage unit comprises 170 mg amantadine hydrochloride. In another more specific embodiment, the dosage unit comprises 210 mg amantadine hydrochloride.

Suitable plasticizers include medium chain triglycerides, diethyl phthalate, citrate esters, polyethylene glycol, glycerol, acetylated glycerides, castor oil, and the like. The pellets are filled into capsules to provide the desired strength of amantadine. An advantage of this composition is it provides the desired release properties that make the composition suitable for administration during said period before bedtime. A further advantage is that the extended release coating is sufficiently durable so that the capsule can be opened and the pellets sprinkled onto food for administration to patients who have difficulty swallowing pills, without adversely affecting the release properties of the composition. When the composition is administered by sprinkling onto food, it is preferred to use a soft food such as applesauce or chocolate pudding, which is consumed within 30 minutes, and preferably within 15 minutes. A yet further advantage of the above-described composition is that it has very good batch-to-batch reproducibility and shelf-life stability.

In some embodiments, the composition of the invention has an in vitro dissolution profile of amantadine of not more than 25% at 2 hours, 55-85% at 6 hours, and at least 80% at 12 hours, as measured using a USP Apparatus II (Paddles) at 50 rpm with 500 ml water at 37° C. as the dissolution medium. More preferably, the in vitro dissolution is further characterized by release of amantadine of not more than 10% at 1 hour, 30-50% at 4 hours, and at least 90% at 12 hours.

In additional embodiments, 110 mg to 210 mg of ER amantadine in a size 1 capsule of the composition of the invention has an in vitro dissolution profile of amantadine of not more than 25% at 2 hours, 55-85% at 6 hours, and at least 80% at 12 hours, as measured using a USP Apparatus II (Paddles) at 50 rpm with 500 ml water at 37° C. as the dissolution medium. More preferably, the in vitro dissolution is further characterized by release of amantadine of not more than 10% at 1 hour, 30-50% at 4 hours, and at least 90% at 12 hours.

In one embodiment of any of the above aspects the composition has an in vitro dissolution profile of amantadine which shows at least one of (i) not more than 25% dissolution at 2 hours, (ii) not more than 25-55% dissolution at 6 hours, and (iii) at least 80% dissolution at 12 hours, using a USP Apparatus II (Paddles) at 50 rpm with 500 ml water at 37° C. as the dissolution medium. In a more specific embodiment two of criteria (i), (ii) and (iii) are met. In a more specific embodiment, all three of criteria (i), (ii) and (iii) are met.

In one embodiment of any of the above aspects the composition has an in vitro dissolution profile of amantadine which shows at least one of (i) not more than 20% dissolution at 1 hour, (ii) about 25-45% dissolution at 2 hours, (iii) not more than 50-80% dissolution at 4 hours, and (iii) at least 80% dissolution at 8 hours, using a USP Apparatus II (Paddles) at 50 rpm with 500 ml water at 37° C. as the dissolution medium. In a more specific embodiment two of criteria (i), (ii) and (iii) are met. In a more specific embodiment, all three of criteria (i), (ii) and (iii) are met.

A preferred pellet-in-capsule compostion of the invention, in addition to having the above in vitro dissolution properties and any of the above-described pharmacokinetic properties (e.g. in vivo release profile, Tmax, Cmax/Cmin ratio, etc) that make the composition suitable for administration in said period before bedtime. The composition is further characterized by providing a Cmax of 1.6-2.4 ng/ml per mg of amantadine and an $AUC_{0-inf}$ of 40-75 ng*h/mL per mg of amantadine after oral administration of a single dose of the capsule to a human subject in a fasted state. A preferred pellet-in-capsule composition is further characterized by a steady state plasma concentration in which once daily oral administration of the capsule to a human subject provides a Cmax of 2.4 to 4.2 ng/ml per mg of amantadine, a Cmin of 1.1 to 2.6 ng/ml per mg of amantadine, and an $AUC_{0-24}$ of 48-73 ng*h/mL per mg of amantadine.

The above-described pellet-in-capsule compositions may be provided at a strength suitable for amantadine therapy. Typical strengths range from at least about 50 mg to about 250 mg. In a specific embodiment, the capsule strength is 70 mg, 80 mg, 90 mg, 110 mg, 120 mg, 125 mg, 130 mg, 140 mg, 150 mg, 160 mg, 160 mg, 170 mg, 180 mg, 190 mg, 210 mg, and 220 mg, that provides a single dose $AUC_{0-inf}$ per mg that is equivalent to a 100 mg tablet of an immediate release formulation of amantadine HCl (e.g. Symmetrel®, or other FDA Orange Book reference listed drug). One, two, or three, of such capsules can be administered to a subject in the period before bedtime. In a preferred embodiment, between 220 mg and 650 mg of amantadine is administered using 2 capsules of a suitable ER formulations once daily.

The invention may also be described in terms of the following numbered embodiments:

1. An extended release (ER) composition comprising amantadine, or a pharmaceutically acceptable salt thereof, for use in a method of administering amantadine to a subject in need thereof, said method comprising orally administering said composition less than three hours before bedtime (i.e. the time at which the subject wishes to go to sleep for the night).
2. Use of amantadine, or a pharmaceutically acceptable salt thereof, in the manufacture of a medicament for the treatment of a disease mediated by the NMDA receptor to a subject in need thereof, said medicament being an extended release (ER) composition, and said treatment comprising orally administering said composition less than three hours before bedtime (i.e. the time at which the subject wishes to go to sleep for the night).
3. An extended release (ER) composition comprising amantadine, or a pharmaceutically acceptable salt thereof, for use in a method of reducing sleep disturbance in a human subject undergoing treatment with amantadine, said method comprising administering said composition less than three hours before bedtime (i.e. the time at which the subject wishes to go to sleep for the night).
4. Use of amantadine, or a pharmaceutically acceptable salt thereof, in the manufacture of a medicament for reducing sleep disturbance in a human subject undergoing treatment with amantadine, said medicament being an extended release (ER) composition and being adapted for administration less than three hours before bedtime (i.e. the time at which the subject wishes to go to sleep for the night).

5. The use or composition of any one of embodiments 1-4 wherein administration occurs less than 1 hour before bedtime.

6. The use or composition of any one of embodiments 1-5, wherein the patient has been diagnosed with Parkinson's disease.

7. The use or composition of any one of embodiments 1-6, wherein the composition is administered once daily.

8. The use or composition of any one of embodiments 1-7, wherein the composition is added to food prior to administration.

9. The use or composition of any one of embodiments 1-8, wherein there is no increase in plasma concentration of amantadine for at least one hour after the administration at steady state.

10. The use or composition of any one of embodiments 1-9, wherein there is no increase in plasma concentration of amantadine for at least two hours after the administration at steady state.

11. The use of composition of any one of embodiments 1-10, wherein, the amantadine has a single dose Tmax of 9 to 15 hours and/or a steady state Tmax of 7 to 13 hours after administration.

12. The use or composition of any one of embodiments 1-11, wherein the amantadine has a single dose Tmax of 10 to 14 hours after administration, and/or a steady state Tmax of 8 to 12 hours after administration.

13. The use of composition of any one of embodiments 1-10, wherein, the amantadine has a single dose Tmax of 9 to 15 hours, and/or a steady state Tmax of 7 to 13 hours after administration.

14. The use or composition of any one of embodiments 1-11, wherein the amantadine has a single dose Tmax of 10 to 14 hours after administration, and/or a steady state Tmax of 8 to 12 hours after administration.

15. The use of composition of any one of embodiments 1-10, wherein, the amantadine has a single dose Tmax of 9 to 15 hours, and/or a steady state Tmax of 7 to 13 hours after administration.

16. The use or composition of any one of embodiments 1-11, wherein the amantadine has a single dose Tmax of 10 to 14 hours after administration, and/or a steady state Tmax of 8 to 12 hours after administration.

17. The use of composition of any one of embodiments 1-12, wherein the amantadine has a single dose Tmax of 11 to 13 hours after administration, and or a steady state Tmax of 9 to 11 hours after administration.

18. The use or composition of any one of embodiments 1-13, wherein a once daily oral administration of the composition to a human subject provides a steady state plasma concentration profile characterized by a concentration increase of amantadine of less than 25% at three hours after the administration.

19. The use or composition of any one of embodiments 1-14 having a Cmax/Cmin ratio of 1.5 to 2.0.

20. The use or composition of any one of embodiments 1-15 having a Cmax/Cmin ratio of 1.7 to 1.9.

21. The use or composition of any one of embodiments 1-16, wherein the amantadine is amantadine hydrochloride or amantadine sulfate.

22. The use or composition of any one of embodiments 1-17 wherein the composition comprises 50 to 600 mg of amantadine, or a pharmaceutically acceptable salt thereof.

23. The use or composition of embodiment 18, wherein the composition is administered as one, two, or three or four unit dosage forms each comprising 100 to 175 mg amantadine, or a pharmaceutically acceptable salt thereof.

24. The use or composition of any one of embodiments 1-19 wherein the composition comprises 200 to 420 mg of amantadine, or a pharmaceutically acceptable salt thereof.

25. The use or composition of embodiment 20, wherein the composition is administered as two unit dosage forms each comprising 110 to 175 mg amantadine, or a pharmaceutically acceptable salt thereof.

26. The use or composition of any one of embodiments 1 to 17, wherein the composition comprises 50 to 200 mg amantadine or a pharmaceutically acceptable salt thereof.

27. The use or composition of embodiment 22, wherein the composition comprises 100 to 125 mg amantadine, or a pharmaceutically acceptable salt thereof.

28. The use or composition of embodiment 23, wherein the composition comprises 110 mg amantadine hydrochloride.

29. The use or composition of any one of embodiments 1-24, wherein oral administration of a single dose of the composition to a human subject in a fasted state provides a maximum plasma concentration (Cmax) of amantadine of 1.6 to 2.4 ng/ml per mg of amantadine and an $AUC_{0-inf}$ of 40 to 75 ng*h/mL per mg of amantadine.

30. The use or composition of any one of embodiments 1-25, wherein once daily oral administration of a dose of the composition to a human subject provides a steady state plasma amantadine concentration profile characterized by:
(i) a Cmax of 2.4 to 4.2 ng/ml per mg of amantadine,
(ii) a Cmin of 1.1 to 2.6 ng/ml per mg of amantadine, and
(iii) an $AUC_{0-24}$ of 44 to 83 ng*h/mL per mg of amantadine.

31. The use or composition of embodiment 26, wherein the steady state plasma concentration profile is further characterized by:
(iv) no increase in plasma concentration of amantadine for at least one hour after the administration; and
(v) a Cmax/Cmin ratio of 1.5 to 2.0.

32. The use or composition of embodiment 27, wherein the steady state plasma concentration profile is further characterized by:
(iv) no increase in concentration of amantadine for at least two hours after the administration; and
(v) a Cmax/Cmin ratio of 1.7 to 1.9.

33. The use or composition of any one of embodiments 1-28, wherein the composition has an in vitro dissolution profile of amantadine of not more than 25% at 2 hours, 55-85% at 6 hours, and at least 80% at 12 hours, using a USP Apparatus II (Paddles) at 50 rpm with 500 ml water at 37° C. as the dissolution medium.

34. The use or composition of embodiment 29, wherein the in vitro dissolution profile of amantadine is further characterized by release of amantadine of not more than 10% at 1 hour, 30-50% at 4 hours, and at least 90% at 12 hours 35. The use or composition of any one of embodiments 1-30, wherein the composition has an AUC profile after administration of a single dose of the composition characterized by: a fractional AUC from 0 to 4 hours that is less than 5% of $AUC_{0-inf}$; a fractional AUC from 0 to 8 hours that is about 5 to 15% of $AUC_{0-inf}$; a fractional AUC from 0 to 12 hours that is about 10 to 40% of $AUC_{0-inf}$; a fractional AUC from 0 to 18 hours that is about 25 to 60% of $AUC_{0-inf}$; and a fractional AUC from 0 to 24 hours that is about 40 to 75% of $AUC_{0-inf}$.

36. The use or composition of any one of embodiments 1-31, wherein the composition has an AUC profile after once daily dosing of the composition at steady state conditions characterized by: a fractional AUC from 0 to 4 hours that is about 2 to 25% of $AUC_{24}$; a fractional AUC from 0 to 8 hours that is about 15 to 50% of $AUC_{24}$; a fractional AUC from 0 to 12 hours that is about 30 to 70% of $AUC_{24}$: and a fractional AUC from 0 to 18 hours that is about 60 to 95% of $AUC_{24}$.

37. A pharmaceutical composition as embodied in any one of embodiments 1, 3, or 5 to 32, or the use of any one of embodiments 2, 4 or 5 to 32, wherein said composition is for oral administration and comprises a capsule for oral administration, said capsule comprising a plurality of pellets, each pellet comprising:
    (a) a pellet core comprising amantadine, or a pharmaceutically acceptable salt thereof, and
    (b) an extended release coating surrounding the pellet core.

38. The use or composition of embodiment 32, wherein the extended release coating comprises ethyl cellulose, at least one of povidone and hydroxypropyl methyl cellulose, and a plasticizer.

39. The use or composition of any one of embodiments 33 or 34, wherein the pellet core comprises amantadine, or a pharmaceutically acceptable salt thereof, and a binder coated onto a core seed.

40. The use or composition of embodiment 35, wherein, based on the combined weight of the pellet core and extended release coating, the amantadine is present in amounts from 40 to 60 wt %, the binder is present in amounts from 8 to 25 wt %, the core seed is present in amounts from 8 to 25 wt %, the ethyl cellulose is present in amounts from 10 to 20 wt %, the povidone is present in amounts from 1 to 4 wt %, and the plasticizer is present in amounts from 1 to 4 wt %.

41. The use or composition of any one of embodiments 33 to 36, further comprising a seal coating between the pellet core and the extended release coating.

42. The use or composition of any one of embodiments 35 to 37, wherein the wherein the pellet core comprises a binder, selected from the group consisting of hydroxypropyl methyl cellulose, copovidone, and mixtures thereof.

43. The use or composition of any one of embodiments 18 to 38, wherein the plasticizer is selected from the group consisting of medium chain triglycerides, diethyl phthalate, citrate esters, polyethylene glycol, glycerol, acetylated glycerides and castor oil.

44. A composition of any one of embodiments 33 to 39, for use in a method of treating Parkinson's disease in a human subject in need thereof, said method comprising orally administering said composition.

Some embodiments herein provide a method of administering amantadine to a subject in need thereof, said method comprising orally administering an extended release (ER) composition comprising amantadine, or a pharmaceutically acceptable salt thereof, less than three hours before bedtime. In some embodiments, administration occurs less than 1 hour before bedtime. In some embodiments, the patient has been diagnosed with Parkinson's disease. In some embodiments, the composition is administered once daily. In some embodiments, the composition is added to food prior to administration. In some embodiments, there is no increase in plasma concentration of amantadine for at least one hour after the administration. In some embodiments, there is no increase in plasma concentration of amantadine for at least two hours after the administration. In some embodiments, the amantadine has a single dose Tmax of 9 to 15 hours, and/or a steady state Tmax of 7 to 13 hours. In some embodiments, the amantadine has a single dose Tmax of 10 to 14 hours after administration, and/or a steady state Tmax of 8 to 12 hours. In some embodiments, the amantadine has a single dose Tmax of 11 to 13 hours after administration, and/or a steady state Tmax of 9 to 11 hours. In some embodiments, a once daily oral administration of the composition to a human subject provides a steady state plasma concentration profile characterized by a concentration increase of amantadine of less than 25% at three hours after the administration. In some embodiments, the PK curve has a Cmax/Cmin ratio of 1.5 to 2.0. In some embodiments, the PK curve has a Cmax/Cmin ratio of 1.7 to 1.9. In some embodiments, the ratio of C-ave-day/C-ave night at steady state is 1.2 to 1.6. In some embodiments, the ratio of C-ave-morning/C-ave night at steady state is 1.3 to 1.5. In some embodiments, the average amantadine plasma concentration during the day (C-ave-day) at steady state is 500-2000 ng/ml. In some embodiments, the average amantadine plasma concentration in the morning (C-ave-morning) at steady state is 500-2000 ng/ml. In some embodiments, the amantadine is amantadine hydrochloride or amantadine sulfate. In some embodiments, the composition comprises 50 to 600 mg of amantadine, or a pharmaceutically acceptable salt thereof. In some embodiments, the composition is administered as one, two, or three or four unit dosage forms each comprising 100 to 175 mg amantadine, or a pharmaceutically acceptable salt thereof. In some embodiments, the composition is administered as one or two unit dosage forms each comprising 130 to 210 mg of extended release amantadine, or a pharmaceutically acceptable salt thereof. In some embodiments, the composition is within a capsule of capsule size #1. In some embodiments, the composition comprises 200 to 350 mg of amantadine, or a pharmaceutically acceptable salt thereof. In some embodiments, the composition is administered as two unit dosage forms each comprising 100 to 175 mg amantadine, or a pharmaceutically acceptable salt thereof. In some embodiments, the composition comprises 50 to 200 mg amantadine or a pharmaceutically acceptable salt thereof. In some embodiments, the composition comprises 100 to 125 mg amantadine, or a pharmaceutically acceptable salt thereof. In some embodiments, the composition comprises 110 mg amantadine hydrochloride. In some embodiments, oral administration of a single dose of the composition to a human subject in a fasted state provides a maximum plasma concentration (Cmax) of 1.6 to 2.4 ng/ml per mg of amantadine, and an $AUC_{0-inf}$ of 40 to 75 ng*h/mL per mg of amantadine. In some embodiments, once daily oral administration of a dose of the composition to a human subject provides a steady state plasma concentration profile characterized by: (a) a Cmax of 2.4 to 4.2 ng/ml per mg of amantadine; (b) a Cmin of 1.1 to 2.6 ng/ml per mg of amantadine, and (c) an $AUC_{0-24}$ of 44 to 83 ng*h/mL per mg of amantadine. In some embodiments, the steady state plasma concentration profile is further characterized by: (d) no increase in plasma concentration of amantadine for at least one hour after the administration; and (e) a Cmax/Cmin ratio of 1.5 to 2.0. In some embodiments, the steady state plasma concentration profile is further characterized by: (f) no increase in concentration of amantadine for at least two hours after the administration; and (g) a Cmax/Cmin ratio of 1.7 to 1.9. In some embodiments, the composition has an in vitro dissolution profile of amantadine of not more than 25% at 2 hours, 55-85% at 6 hours, and at least 80% at 12 hours, using a USP Apparatus II (Paddles) at 50 rpm with 500 ml water at 37° C. as the dissolution medium. In some embodiments, the composition has an in vitro dissolution profile of amantadine of not more than 25% at 2 hours, 25-55% at 6 hours, and at least 80% at 12 hours, using a USP Apparatus II (Paddles) at 50 rpm with 500 ml water at 37° C. as the dissolution medium. In some embodiments, the composition has an in vitro dissolution profile of amantadine of not more than 20% at 1 hour, 25-45% at 2 hours, 50-80% at 4 hours, and at least 80% at 8 hours, using a USP Apparatus II (Paddles) at 50 rpm with 500 ml water at 37° C. as the dissolution medium. In some embodiments, the in vitro dissolution profile of amantadine is further characterized by release of amantadine of not more than 10% at 1 hour, 30-50% at 4 hours, and at least 90% at 12 hours. In some embodiments, the composition has an AUC profile after administration of a single dose of the composition characterized by: a fractional AUC from 0 to 4 hours that is less than 5% of $AUC_{0-inf}$; a fractional AUC from 0 to 8 hours that is about 5 to 15% of $AUC_{0-inf}$; a fractional AUC from 0 to 12 hours that is about 10 to 40% of $AUC_{0-inf}$; a fractional AUC from 0 to 18 hours that is about 25 to 60% of $AUC_{0-inf}$; and a fractional AUC from 0 to 24 hours that is about 40 to 75% of $AUC_{0-inf}$. In some embodiments, the composition has an AUC profile after once daily dosing of the composition at steady state conditions characterized by: a fractional AUC from 0 to 4 hours that is about 2 to 25% of $AUC_{24}$; a fractional AUC from 0 to 8 hours that is about 15 to 50% of $AUC_{24}$; a fractional AUC from 0 to 12 hours that is about 30 to 70% of $AUC_{24}$: and a fractional AUC from 0 to 18 hours that is about 60 to 95% of $AUC_{24}$.

Some embodiments herein provide a method of reducing sleep disturbance in a human subject undergoing treatment with amantadine, said method comprising administering an extended release (ER) composition comprising amantadine, or a pharmaceutically acceptable salt thereof, less than three hours before bedtime. In some embodiments, administration occurs less than 1 hour before bedtime. In some embodiments, the patient has been diagnosed with Parkinson's disease. In some embodiments, the composition is administered once daily. In some embodiments, the composition is added to food prior to administration. In some embodiments, there is no increase in plasma concentration of amantadine for at least one hour after the administration. In some embodiments, there is no increase in plasma concentration of amantadine for at least two hours after the administration. In some embodiments, the amantadine has a single dose Tmax of 9 to 15 hours, and/or a steady state Tmax of 7 to 13 hours. In some embodiments, the amantadine has a single dose Tmax of 10 to 14 hours after administration, and/or a steady state Tmax of 8 to 12 hours. In some embodiments, the amantadine has a single dose Tmax of 11 to 13 hours after administration, and/or a steady state Tmax of 9 to 11 hours. In some embodiments, a once daily oral administration of the composition to a human subject provides a steady state plasma concentration profile characterized by a concentration increase of amantadine of less than 25% at three hours after the administration. In some embodiments, the PK curve has a Cmax/Cmin ratio of 1.5 to 2.0. In some embodiments, the PK curve has a Cmax/Cmin ratio of 1.7 to 1.9. In some embodiments, the ratio of C-ave-day/C-ave night at steady state is 1.2 to 1.6. In some embodiments, the ratio of C-ave-morning/C-ave night at steady state is 1.3 to 1.5. In some embodiments, the average amantadine plasma concentration during the day (C-ave-day) at steady state is 500-2000 ng/ml. In some embodiments, the average amantadine plasma concentration in the morning (C-ave-morning) at steady state is 500-2000 ng/ml. In some embodiments, the amantadine is amantadine hydrochloride or amantadine sulfate. In some embodiments, the composition comprises 50 to 600 mg of amantadine, or a pharmaceutically acceptable salt thereof. In some embodiments, the composition is administered as one, two, or three or four unit dosage forms each comprising 100 to 175 mg amantadine, or a pharmaceutically acceptable salt thereof. In some embodiments, the composition is administered as one or two unit dosage forms each comprising 130 to 210 mg of extended release amantadine, or a pharmaceutically acceptable salt thereof. In some embodiments, the composition is within a capsule of capsule size #1. In some embodiments, the composition comprises 200 to 350 mg of amantadine, or a pharmaceutically acceptable salt thereof. In some embodiments, the composition is administered as two unit dosage forms each comprising 100 to 175 mg amantadine, or a pharmaceutically acceptable salt thereof. In some embodiments, the composition comprises 50 to 200 mg amantadine or a pharmaceutically acceptable salt thereof. In some embodiments, the composition comprises 100 to 125 mg amantadine, or a pharmaceutically acceptable salt thereof. In some embodiments, the composition comprises 110 mg amantadine hydrochloride. In some embodiments, oral administration of a single dose of the composition to a human subject in a fasted state provides a maximum plasma concentration (Cmax) of 1.6 to 2.4 ng/ml per mg of amantadine, and an $AUC_{0-inf}$ of 40 to 75 ng*h/mL per mg of amantadine. In some embodiments, once daily oral administration of a dose of the composition to a human subject provides a steady state plasma concentration profile characterized by: (a) a Cmax of 2.4 to 4.2 ng/ml per mg of amantadine; (b) a Cmin of 1.1 to 2.6 ng/ml per mg of amantadine, and (c) an $AUC_{0-24}$ of 44 to 83 ng*h/mL per mg of amantadine. In some embodiments, the steady state plasma concentration profile is further characterized by: (d) no increase in plasma concentration of amantadine for at least one hour after the administration; and (e) a Cmax/Cmin ratio of 1.5 to 2.0. In some embodiments, the steady state plasma concentration profile is further characterized by: (f) no increase in concentration of amantadine for at least two hours after the administration; and (g) a Cmax/Cmin ratio of 1.7 to 1.9. In some embodiments, the composition has an in vitro dissolution profile of amantadine of not more than 25% at 2 hours, 55-85% at 6 hours, and at least 80% at 12 hours, using a USP Apparatus II (Paddles) at 50 rpm with 500 ml water at 37° C. as the dissolution medium. In some embodiments, the composition has an in vitro dissolution profile of amantadine of not more than 25% at 2 hours, 25-55% at 6 hours, and at least 80% at 12 hours, using a USP Apparatus II (Paddles) at 50 rpm with 500 ml water at 37° C. as the dissolution medium. In some embodiments, the composition has an in vitro dissolution profile of amantadine of not more than 20% at 1 hour, 25-45% at 2 hours, 50-80% at 4 hours, and at least 80% at 8 hours, using a USP Apparatus II (Paddles) at 50 rpm with 500 ml water at 37° C. as the dissolution medium. In some embodiments, the in vitro dissolution profile of amantadine is further characterized by release of amantadine of not more than 10% at 1 hour, 30-50% at 4 hours, and at least 90% at 12 hours. In some embodiments, the composition has an AUC profile after administration of a single dose of the composition characterized by: a fractional AUC from 0 to 4 hours that is less than 5% of $AUC_{0-inf}$; a fractional AUC from 0 to 8 hours that is about 5 to 15% of $AUC_{0-inf}$; a fractional AUC from 0 to 12 hours that is about 10 to 40% of $AUC_{0-inf}$; a fractional AUC from 0 to 18 hours that is about 25 to 60% of $AUC_{0-inf}$; and a fractional AUC from 0 to 24 hours that is about 40 to 75% of $AUC_{0-inf}$. In some embodiments, the composition has an AUC profile after once daily dosing of the composition at steady state conditions characterized by: a fractional AUC from 0 to 4 hours that is about 2 to 25% of $AUC_{24}$; a fractional AUC from 0 to 8 hours that is about 15 to 50% of $AUC_{24}$; a fractional AUC from 0 to 12 hours that is about 30 to 70% of $AUC_{24}$: and a fractional AUC from 0 to 18 hours that is about 60 to 95% of $AUC_{24}$.

Some embodiments herein provide a method of treating levodopa induced dyskinesia in a patient with Parkinson's disease, said method comprising orally administering once daily an extended release (ER) composition comprising amantadine, or a pharmaceutically acceptable salt thereof, less than about three hours before bedtime. In some embodiments, administration occurs less than 1 hour before bedtime. In some embodiments, the patient has been diagnosed with Parkinson's disease. In some embodiments, the composition is administered once daily. In some embodiments, the composition is added to food prior to administration. In some embodiments, there is no increase in plasma concentration of amantadine for at least one hour after the administration. In some embodiments, there is no increase in plasma concentration of amantadine for at least two hours after the administration. In some embodiments, the amantadine has a single dose Tmax of 9 to 15 hours, and/or a steady state Tmax of 7 to 13 hours. In some embodiments, the amantadine has a single dose Tmax of 10 to 14 hours after administration, and/or a steady state Tmax of 8 to 12 hours. In some embodiments, the amantadine has a single dose Tmax of 11 to 13 hours after administration, and/or a steady state Tmax of 9 to 11 hours. In some embodiments, a once daily oral administration of the composition to a human subject provides a steady state plasma concentration profile characterized by a concentration increase of amantadine of less than 25% at three hours after the administration. In some embodiments, the PK curve has a Cmax/Cmin ratio of 1.5 to 2.0. In some embodiments, the PK curve has a Cmax/Cmin ratio of 1.7 to 1.9. In some embodiments, the ratio of C-ave-day/C-ave night at steady state is 1.2 to 1.6. In some embodiments, the ratio of C-ave-morning/C-ave night at steady state is 1.3 to 1.5. In some embodiments, the average amantadine plasma concentration during the day (C-ave-day) at steady state is 500-2000 ng/ml. In some embodiments, the average amantadine plasma concentration in the morning (C-ave-morning) at steady state is 500-2000 ng/ml. In some embodiments, the amantadine is amantadine hydrochloride or amantadine sulfate. In some embodiments, the composition comprises 50 to 600 mg of amantadine, or a pharmaceutically acceptable salt thereof. In some embodiments, the composition is administered as one, two, or three or four unit dosage forms each comprising 100 to 175 mg amantadine, or a pharmaceutically acceptable salt thereof. In some embodiments, the composition is administered as one or two unit dosage forms each comprising 130 to 210 mg of extended release amantadine, or a pharmaceutically acceptable salt thereof. In some embodiments, the composition is within a capsule of capsule size #1. In some embodiments, the composition comprises 200 to 350 mg of amantadine, or a pharmaceutically acceptable salt thereof. In some embodiments, the composition is administered as two unit dosage forms each comprising 100 to 175 mg amantadine, or a pharmaceutically acceptable salt thereof. In some embodiments, the composition comprises 50 to 200 mg amantadine or a pharmaceutically acceptable salt thereof. In some embodiments, the composition comprises 100 to 125 mg amantadine, or a pharmaceutically acceptable salt thereof. In some embodiments, the composition comprises 110 mg amantadine hydrochloride. In some embodiments, oral administration of a single dose of the composition to a human subject in a fasted state provides a maximum plasma concentration (Cmax) of 1.6 to 2.4 ng/ml per mg of amantadine, and an $AUC_{0-inf}$ of 40 to 75 ng*h/mL per mg of amantadine. In some embodiments, once daily oral administration of a dose of the composition to a human subject provides a steady state plasma concentration profile characterized by: (a) a Cmax of 2.4 to 4.2 ng/ml per mg of amantadine; (b) a Cmin of 1.1 to 2.6 ng/ml per mg of amantadine, and (c) an $AUC_{0-24}$ of 44 to 83 ng*h/mL per mg of amantadine. In some embodiments, the steady state plasma concentration profile is further characterized by: (d) no increase in plasma concentration of amantadine for at least one hour after the administration; and (e) a Cmax/Cmin ratio of 1.5 to 2.0. In some embodiments, the steady state plasma concentration profile is further characterized by: (f) no increase in concentration of amantadine for at least two hours after the administration; and (g) a Cmax/Cmin ratio of 1.7 to 1.9. In some embodiments, the composition has an in vitro dissolution profile of amantadine of not more than 25% at 2 hours, 55-85% at 6 hours, and at least 80% at 12 hours, using a USP Apparatus II (Paddles) at 50 rpm with 500 ml water at 37° C. as the dissolution medium. In some embodiments, the composition has an in vitro dissolution profile of amantadine of not more than 25% at 2 hours, 25-55% at 6 hours, and at least 80% at 12 hours, using a USP Apparatus II (Paddles) at 50 rpm with 500 ml water at 37° C. as the dissolution medium. In some embodiments, the composition has an in vitro dissolution profile of amantadine of not more than 20% at 1 hour, 25-45% at 2 hours, 50-80% at 4 hours, and at least 80% at 8 hours, using a USP Apparatus II (Paddles) at 50 rpm with 500 ml water at 37° C. as the dissolution medium. In some embodiments, the in vitro dissolution profile of amantadine is further characterized by release of amantadine of not more than 10% at 1 hour, 30-50% at 4 hours, and at least 90% at 12 hours. In some embodiments, the composition has an AUC profile after administration of a single dose of the composition characterized by: a fractional AUC from 0 to 4 hours that is less than 5% of $AUC_{0-inf}$; a fractional AUC from 0 to 8 hours that is about 5 to 15% of $AUC_{0-inf}$; a fractional AUC from 0 to 12 hours that is about 10 to 40% of $AUC_{0-inf}$; a fractional AUC from 0 to 18 hours that is about 25 to 60% of $AUC_{0-inf}$; and a fractional AUC from 0 to 24 hours that is about 40 to 75% of $AUC_{0-inf}$. In some embodiments, the composition has an AUC profile after once daily dosing of the composition at steady state conditions characterized by: a fractional AUC from 0 to 4 hours that is about 2 to 25% of $AUC_{24}$; a fractional AUC from 0 to 8 hours that is about 15 to 50% of $AUC_{24}$; a fractional AUC from 0 to 12 hours that is about 30 to 70% of $AUC_{24}$: and a fractional AUC from 0 to 18 hours that is about 60 to 95% of $AUC_{24}$.

Some embodiments herein provide a pharmaceutical composition for any of the methods described herein, wherein said composition is for oral administration and comprises a capsule for oral administration, said capsule comprising a plurality of pellets, each pellet comprising: (a) a pellet core comprising amantadine, or a pharmaceutically acceptable salt thereof, and (b) an extended release coating surrounding the pellet core. In some embodiments, the extended release coating comprises ethyl cellulose, at least one of povidone and hydroxypropyl methyl cellulose, and a plasticizer. In some embodiments, the pellet core comprises amantadine, or a pharmaceutically acceptable salt thereof, and a binder coated onto a core seed. In some embodiments, based on the combined weight of the pellet core and extended release coating, the amantadine is present in amounts from 40 to 60 wt %, the binder is present in amounts from 8 to 25 wt %, the core seed is present in amounts from 1 to 25 wt %, the ethyl cellulose is present in amounts from 10 to 20 wt %, the povidone is present in amounts from 1 to 4 wt %, and the plasticizer is present in amounts from 1 to 4 wt %. In some embodiments, the composition further comprises a seal coating between the pellet core and the extended release coating. In some embodiments, the pellet core comprises a binder selected from the group consisting of hydroxypropyl methyl cellulose, copovidone, and mixtures thereof. In some embodiments, the plasticizer is selected from the group consisting of medium chain triglycerides, diethyl phthalate, citrate esters, polyethylene glycol, glycerol, acetylated glycerides and castor oil.

Some embodiments herein provide a method of administering amantadine, or a pharmaceutically acceptable salt thereof, to a human subject in need thereof, said method comprising orally administering a pharmaceutical composition comprising amantadine in a capsule for oral administration, said capsule comprising a plurality of pellets, each pellet comprising: (a) a pellet core comprising amantadine, or a pharmaceutically acceptable salt thereof, and (b) an extended release coating surrounding the pellet core. In some embodiments, the extended release coating comprises ethyl cellulose, at least one of povidone and hydroxypropyl methyl cellulose, and a plasticizer. In some embodiments, the pellet core comprises amantadine, or a pharmaceutically acceptable salt thereof, and a binder coated onto a core seed. In some embodiments, based on the combined weight of the pellet core and extended release coating, the amantadine is present in amounts from 40 to 60 wt %, the binder is present in amounts from 8 to 25 wt %, the core seed is present in amounts from 1 to 25 wt %, the ethyl cellulose is present in amounts from 10 to 20 wt %, the povidone is present in amounts from 1 to 4 wt %, and the plasticizer is present in amounts from 1 to 4 wt %. In some embodiments, the composition further comprises a seal coating between the pellet core and the extended release coating. In some embodiments, the pellet core comprises a binder selected from the group consisting of hydroxypropyl methyl cellulose, copovidone, and mixtures thereof. In some embodiments, the plasticizer is selected from the group consisting of medium chain triglycerides, diethyl phthalate, citrate esters, polyethylene glycol, glycerol, acetylated glycerides and castor oil. Some embodiments comprise treating Parkinson's disease in a human subject in need thereof.

Some embodiments herein provide a pharmaceutical composition suitable for once daily oral administration to a patient in need thereof said composition comprising a therapeutically effective amount of amantadine or a pharmaceutically acceptable salt thereof in an extended release form which can be administered as not more than two size 0 or smaller capsules in a single daily administration. In some embodiments, the composition comprises 110-220 mg of amantadine or pharmaceutically acceptable salt thereof. In some embodiments, the composition has an in vitro dissolution profile of amantadine of not more than 25% at 2 hours, 40-80% at 6 hours, and at least 80% at 12 hours, using a USP Apparatus II (Paddles) at 50 rpm with 500 ml water at 37° C. as the dissolution medium. In some embodiments, the composition comprises a plurality of pellets, each pellet comprising: (a) a pellet core comprising amantadine, or a pharmaceutically acceptable salt thereof, and (b) an extended release coating surrounding the pellet core. In some embodiments, the extended release coating comprises ethyl cellulose, at least one of povidone and hydroxypropyl methyl cellulose, and a plasticizer. In some embodiments, the pellet core comprises amantadine, or a pharmaceutically acceptable salt thereof, and a binder coated onto a core seed. In some embodiments, the composition comprises amantadine and, based on the combined weight of the pellet core and extended release coating, the amantadine is present in amounts from 40 to 70 wt %. In some embodiments, the pellet core comprises a core seed comprising sugar or microcrystalline cellulose that is between 100 and 500 microns in diameter. In some embodiments, the bulk density is between 0.5 and 1 gm/cm$^3$. In some embodiments, the composition comprises a seal coating between the pellet core and the extended release coating. In some embodiments, the pellet core comprises a binder selected from the group consisting of hydroxypropyl methyl cellulose, copovidone, and mixtures thereof. In some embodiments, the plasticizer is selected from the group consisting of medium chain triglycerides, diethyl phthalate, citrate esters, polyethylene glycol, glycerol, acetylated glycerides and castor oil.

Some embodiments herein provide a method of treating Parkinson's disease in a human subject, said method comprising orally administering a composition comprising a therapeutically effective amount of amantadine or a pharmaceutically acceptable salt thereof in an extended release form which can be administered as not more than two size 0 or smaller capsules in a single daily administration. In some embodiments, the composition comprises 110-220 mg of amantadine or pharmaceutically acceptable salt thereof. In some embodiments, the composition has an in vitro dissolution profile of amantadine of not more than 25% at 2 hours, 40-80% at 6 hours, and at least 80% at 12 hours, using a USP Apparatus II (Paddles) at 50 rpm with 500 ml water at 37° C. as the dissolution medium. In some embodiments, the composition comprises a plurality of pellets, each pellet comprising: (a) a pellet core comprising amantadine, or a pharmaceutically acceptable salt thereof, and (b) an extended release coating surrounding the pellet core. In some embodiments, the extended release coating comprises ethyl cellulose, at least one of povidone and hydroxypropyl methyl cellulose, and a plasticizer. In some embodiments, the pellet core comprises amantadine, or a pharmaceutically acceptable salt thereof, and a binder coated onto a core seed. In some embodiments, the composition comprises amantadine and, based on the combined weight of the pellet core and extended release coating, the amantadine is present in amounts from 40 to 70 wt %. In some embodiments, the pellet core comprises a core seed comprising sugar or microcrystalline cellulose that is between 100 and 500 microns in diameter. In some embodiments, the bulk density is between 0.5 and 1 gm/cm$^3$. In some embodiments, the composition comprises a seal coating between the pellet core and the extended release coating. In some embodiments, the pellet core comprises a binder selected from the group consisting of hydroxypropyl methyl cellulose, copovidone, and mixtures thereof. In some embodiments, the plasticizer is selected from the group consisting of medium chain triglycerides, diethyl phthalate, citrate esters, polyethylene glycol, glycerol, acetylated glycerides and castor oil.

Some embodiments herein provide a method of treating levodopa induced dyskinesia in a human subject, said method comprising orally administering a composition comprising a therapeutically effective amount of amantadine or a pharmaceutically acceptable salt thereof in an extended release form which can be administered as not more than two size 0 or smaller capsules in a single daily administration. Some embodiments herein provide a method of treating traumatic brain injury in a human subject, said method comprising orally administering a composition comprising a therapeutically effective amount of amantadine or a pharmaceutically acceptable salt thereof in an extended release form which can be administered as not more than two size 0 or smaller capsules in a single daily administration. Some embodiments provide a method of treating traumatic brain injury in a human subject, said method comprising orally administering a composition comprising a therapeutically effective amount of amantadine or a pharmaceutically acceptable salt thereof in an extended release form which can be administered as not more than two size 0 or smaller capsules in a single daily administration. Some embodiments provide a method of treating fatigue in a human subject, said method comprising orally administering a composition comprising a therapeutically effective amount of amantadine or a pharmaceutically acceptable salt thereof in an extended release form which can be administered as not more than two size 0 or smaller capsules in a single daily administration. In some embodiments, the composition comprises 110-220 mg of amantadine or pharmaceutically acceptable salt thereof. In some embodiments, the composition has an in vitro dissolution profile of amantadine of not more than 25% at 2 hours, 40-80% at 6 hours, and at least 80% at 12 hours, using a USP Apparatus II (Paddles) at 50 rpm with 500 ml water at 37° C. as the dissolution medium. In some embodiments, the composition comprises a plurality of pellets, each pellet comprising: (a) a pellet core comprising amantadine, or a pharmaceutically acceptable salt thereof, and (b) an extended release coating surrounding the pellet core. In some embodiments, the extended release coating comprises ethyl cellulose, at least one of povidone and hydroxypropyl methyl cellulose, and a plasticizer. In some embodiments, the pellet core comprises amantadine, or a pharmaceutically acceptable salt thereof, and a binder coated onto a core seed. In some embodiments, the composition comprises amantadine and, based on the combined weight of the pellet core and extended release coating, the amantadine is present in amounts from 40 to 70 wt %. In some embodiments, the pellet core comprises a core seed comprising sugar or microcrystalline cellulose that is between 100 and 500 microns in diameter. In some embodiments, the bulk density is between 0.5 and 1 gm/cm$^3$. In some embodiments, the composition comprises a seal coating between the pellet core and the extended release coating. In some embodiments, the pellet core comprises a binder selected from the group consisting of hydroxypropyl methyl cellulose, copovidone, and mixtures thereof. In some embodiments, the plasticizer is selected from the group consisting of medium chain triglycerides, diethyl phthalate, citrate esters, polyethylene glycol, glycerol, acetylated glycerides and castor oil. In some embodiments, the method comprises administering the composition to a patient less than three hours before bed time.

The present invention may be better understood by reference to the following examples, which are not intended to limit the scope of the claims.

Example 1: Amantadine Extended Release Coated Pellet Formulations

Amantadine HCl extended release coated pellet compositions designed for nighttime administration were prepared using the components and relative amounts shown in Table 1 below. For each composition, the drug coating solution was prepared by adding HPMC 5 cps and Copovidone to isopropyl alcohol with continuous stirring. Purified water was added to this dispersion and stirring continued until a clear solution is formed. Drug (Amantadine HCl) was then added to this binder solution and stirring continued until the drug was completely dissolved. Finally, talc was added and dispersed uniformly by stirring.

Celphere beads (screen sizes #35 to #50 i.e. 300 to 500 micron) were loaded in a Wurster coating unit. The drug coating dispersion was sprayed onto the beads followed by a period of drying. The resulting drug coated pellets were sieved to retain the fraction between screens #18 and #24 (approximately 700 µm to 1 mm diameter).

The seal coating solution was prepared by adding HPMC 5 cps to isopropyl alcohol with continuous stirring. Purified water was added to this dispersion and stirring continued until a clear solution was formed. Talc was added and dispersed uniformly by stirring. The sieved drug coated pellets were loaded in a Wurster coating unit. The seal coating dispersion was sprayed over the drug coated pellets followed by a period of drying to remove the residual solvent and water in the pellets. The resulting seal coated pellets were sieved to retain the fraction between screens #18 and #24.

The ER coating solution was prepared by dissolving ethyl cellulose (viscosity 7 cps) in isopropyl alcohol and purified water and stirring until a clear solution was formed. Povidone K-90 was then dissolved in this clear solution followed by addition of plasticizer Miglyol 812N with continuous stirring to form a clear solution. The sieved seal coated pellets were loaded in a Wurster coating unit. The ER coating solution was sprayed over the seal coated pellets followed by a period of drying to affect the ER coat and remove the residual solvent and water in the pellets. After drying, magnesium stearate was spread on the top bed of the coated pellets in the annulus region followed by recirculation of the pellets in the Wurster unit to blend the magnesium stearate with the coated pellets. The resulting ER coated pellets were sieved to retain the fraction between screens #18 and #24.

The desired weight of the ER coated pellets containing the unit dose were filled into empty 1 hard gelatin capsule shell (size 1 for 100-140 mg strength) using an encapsulator equipped with pellet dosing chamber.

TABLE 1

| Composition of amantadine HCl ER capsules | | |
|---|---|---|
| Component | Function | combined w/w of capsule |
| Pellet Core | | |
| Amantadine Hydrochloride USP | Active | 40-50% |
| Microcrystalline cellulose spheres (Celphere ®) | Core seeds | 10-15% |
| Hydroxypropyl methyl cellulose 5 cps USP | Binder | 10-15% |
| Copovidone | Binder | 1-5% |
| Talc USP | Anti-tack | 1-5% |

TABLE 1-continued

Composition of amantadine HCl ER capsules

| Component | Function | combined w/w of capsule |
|---|---|---|
| Isopropyl alcohol | Solvent | —[1] |
| Water | Solvent | —[1] |
| Seal Coating (optional) | | |
| Hydroxypropyl methyl cellulose 3 cps USP | Coating polymer | 5-10% |
| Talc USP | Anti-tack | 0-5% |
| Isopropyl alcohol | Solvent | —[1] |
| Water | Solvent | —[1] |
| Extended Release Coating | | |
| Ethyl cellulose | Coating polymer | 10-20% |
| Povidone | Pore former | 1-5% |
| Medium chain triglycerides | Plasticizer | 1-5% |
| Isopropyl alcohol | Solvent | —[1] |
| Water | Solvent | —[1] |
| Magnesium Stearate NF | Lubricant | 0-1% |
| Density of pellets | | 0.6-0.9 gm/cm$^3$ |

NF = National Formulary
[1]Purified water and isopropyl alcohol are removed during processing.

The in vitro dissolution of capsules prepared above was tested using a USP Apparatus II (Paddles) at 50 rpm with 500 ml water at 37° C. as the dissolution medium. Capsules meeting desired dissolution specifications released not more than 25% of the drug in 2 hours, 40-80% in 6 hours, and at least 80% at 12 hours. In an exemplary dissolution profile, there was 0% drug release at 1 hour, 12% release at 2 hours, 43% release at 4 hours, 68% release at 6 hours, 83% release at 8 hours, 92% release at 10 hours, and 97% release at 12 hours. Capsules prepared in accordance with the above method exhibited good shelf-stability, and batch-to-batch reproducibility upon scale-up.

Example 2: Amantadine Extended Release Coated Pellet Formulation with Higher Drug Loading Amantadine HCl extended release coated pellet compositions designed for nighttime administration are prepared using the components and relative amounts shown in Table 2 below and the manufacturing process described in example 1.

The diameter of the inert cores is 200-300 microns. The diameter of the coated pellets is 600-1200 microns. The bulk density of the coated pellets is 0.7-1.2 g/cm$^3$.

The desired weight of the ER coated pellets containing the unit dose are filled into an empty hard gelatin capsule shell (size 1 for 170 mg strength) using an encapsulator equipped with pellet dosing chamber.

TABLE 2

Composition of amantadine HCl ER capsules

| Component | Function | combined w/w of capsule |
|---|---|---|
| Pellet Core | | |
| Amantadine Hydrochloride USP | Active | 50-65% |
| Microcrystalline cellulose spheres (Celphere ®) | Core seeds | 1-15% |
| Hydroxypropyl methyl cellulose USP | Binder | 5-25% |
| Copovidone | Binder | 1-5% |
| Talc USP | Anti-tack | 1-5% |

TABLE 2-continued

Composition of amantadine HCl ER capsules

| Component | Function | combined w/w of capsule |
|---|---|---|
| Isopropyl alcohol | Solvent | —[1] |
| Water | Solvent | —[1] |
| Seal Coating (optional) | | |
| Hydroxypropyl methyl cellulose USP | Coating polymer | 0-10% |
| Talc USP | Anti-tack | 0-5% |
| Isopropyl alcohol | Solvent | —[1] |
| Water | Solvent | —[1] |
| Extended Release Coating | | |
| Ethyl cellulose | Coating polymer | 10-20% |
| Povidone | Pore former | 1-5% |
| Medium chain triglycerides | Plasticizer | 1-5% |
| Isopropyl alcohol | Solvent | —[1] |
| Water | Solvent | —[1] |
| Magnesium Stearate NF | Lubricant | 0-1% |

NF = National Formulary
[1]Purified water and isopropyl alcohol are removed during processing.

The in vitro dissolution of capsules prepared above are tested using a USP Apparatus II (Paddles) at 50 rpm with 500 ml water at 37° C. as the dissolution medium and release not more than 25% of the drug in 2 hours, 40-80% in 6 hours, and at least 80% at 12 hours.

Example 3: Amantadine Extended Release Coated Pellet Formulations

Amantadine HCl extended release coated pellet compositions suitable for nighttime administration were prepared using the components and relative amounts shown in Table 3 below and the manufacturing process described in Example 1.

The desired weight of the ER coated pellets containing the unit dose was filled into empty #1 hard gelatin capsule shell (100 mg strength) using an encapsulator equipped with pellet dosing chamber.

TABLE 3

Composition of amantadine HCl ER capsules

| | | combined w/w of capsule | | |
|---|---|---|---|---|
| Component | Function | A | B | C |
| Pellet Core | | | | |
| Amantadine Hydrochloride USP | Active | 50.15% | 47.94% | 45.15% |
| Microcrystalline cellulose spheres (Celphere ®) | Core seeds | 14.33% | 13.70% | 12.90% |
| Hydroxypropyl methyl cellulose USP | Binder | 13.37% | 12.79% | 12.04% |
| Copovidone | Binder | 3.34% | 3.2% | 3.01% |
| Talc USP | Anti-tack | 2.51% | 2.4% | 2.26% |
| Isopropyl alcohol | Solvent | —[1] | —[1] | —[1] |
| Water | Solvent | —[1] | —[1] | —[1] |
| Seal Coating (optional) | | | | |
| Hydroxypropyl methyl cellulose USP | Coating polymer | 7.61% | 7.27% | 6.85% |
| Talc USP | Anti-tack | 0.76% | 0.73% | 0.69% |
| Isopropyl alcohol | Solvent | —[1] | —[1] | —[1] |
| Water | Solvent | —[1] | —[1] | —[1] |

TABLE 3-continued

Composition of amantadine HCl ER capsules

| | | combined w/w of capsule | | |
|---|---|---|---|---|
| Component | Function | A | B | C |
| Extended Release Coating | | | | |
| Ethyl cellulose | Coating polymer | 6.23% | 9.46% | 13.53% |
| Povidone | Pore former | 0.85% | 1.29% | 1.84% |
| Medium chain triglycerides | Plasticizer | 0.75% | 1.13% | 1.62% |
| Isopropyl alcohol | Solvent | —[1] | —[1] | —[1] |
| Water | Solvent | —[1] | —[1] | —[1] |
| Magnesium Stearate NF | Lubricant | 0.1% | 0.1% | 0.1% |

NF = National Formulary
[1]Purified water and isopropyl alcohol are removed during processing.

The in vitro dissolution of capsules prepared above were tested using a USP Apparatus II (Paddles) at 50 rpm with 500 ml water at 37° C. as the dissolution medium. The results are shown in FIG. 1.

Example 4: Amantadine Extended Release Formulation Made by Extrusion Spheronization Amantadine HCl extended release compositions designed for nighttime administration are prepared using the components and relative amounts shown in Table 4 below and the manufacturing process described below.

A blend of amantadine HCl, microcrystalline cellulose and lactose monohydrate was prepared and a wet mass is prepared in a high shear granulator using an aqueous solution of povidone. The wet mass is extruded using 1 mm sieve and extruded mass is spheronized using a spheronizer. The pellets are dried in a tray drier to yield core pellets. The core pellets are coated with extended release coating solution in a pan coater. The desired weight of the ER coated pellets containing the unit dose is filled into empty 1 hard gelatin capsule shell (170 mg strength) using an encapsulator equipped with pellet dosing chamber.

TABLE 4

Composition of amantadine HCl ER capsules

| Component | Function | combined w/w of capsule |
|---|---|---|
| Pellet Core | | |
| Amantadine Hydrochloride USP | Active | 59.40% |
| Microcrystalline cellulose | Diluent | 18.67% |
| Lactose monohydrate | Diluent | 6.15% |
| Povidone | Binder | 0.64% |
| Water | Solvent | —[1] |
| Extended Release Coating | | |
| Ethyl cellulose | Coating polymer | 12.41% |
| Polyethylene glycol | Pore former | 1.24% |
| Dibutyl sebacate | Plasticizer | 1.49% |
| Ethanol | Solvent | —[1] |

The in vitro dissolution of capsules prepared above are tested using a USP Apparatus II (Paddles) at 50 rpm with 500 ml water at 37° C. as the dissolution medium and release not more than 25% of the drug in 2 hours, 40-80% in 6 hours, and at least 80% at 12 hours.

Example 5: Pharmacokinetic Measurement of Formulations of Amantadine ER Compared to IR Amantadine Objective: The primary objective of the study was to confirm the PK properties of extended release formulations in example 3, to determine the pharmacokinetic profiles, safety and tolerability of three prototype formulations of ER capsules of amantadine HCl described with different release properties in Example 3 relative to a 100 mg film-coated IR amantadine HCl tablet (SYMMETREL®) given as single doses to healthy adult subjects under fasting conditions.

Study design: This was a Phase 1, randomized, single dose, open-label, four-period, crossover, fasting pharmacokinetic study in which single 100 mg doses of three formulations of Amantadine ER capsules with different release properties were compared to single 100 mg doses of marketed amantadine IR tablets (SYMMETREL®). The three ER formulations differed in the amantadine release rates in vitro, as shown in FIG. 1.

Methods: Subjects were admitted to the unit for the first period of dosing within 21 days of study screening. Subjects were dosed on the day after checking into the unit and discharged at 24 hours post dose. Subjects were asked to return after discharge for follow-up visits at 56 hours and 152 hours after dosing. Each dosing period was separated by at least 7 day washout.

After an overnight fast, the formulation was administered to the subjects while in a sitting position with 240 mL of water. Blood samples were collected at 0 (pre-dose), 1, 2, 3, 4, 5, 6, 7, 8, 9, 10, 11, 12, 13, 14, 15, 16, 18, 24 (discharge), and 56 hours following each dose. Plasma samples were assayed for amantadine by a validated liquid chromatography/tandem mass spectroscopy (LC/MS/MS) method. Pharmacokinetic parameters were calculated using a non-compartmental analysis with WinNonlin software (version 4.1 or higher; Pharsight Corporation).

An analysis of variance (ANOVA) was performed on the natural logarithms of Cmax and AUC0-∞ determined from the data following a single dose of study drug using linear mixed effects model. The model included effects for subject, sequence, period, and regimen. The effects of sequence, period, and regimen were fixed, while the effect of subject was random. Ratio of ER to IR for both AUC (relative bioavailability for ER formualtions) and Cmax was calculated. (Adverse events were monitored throughout the study. Vital signs (pulse rate, blood pressure and body temperature), clinical laboratory measures (biochemistry, hematology, and urinalysis) and ECGs were collected at various times during the study.

Results: A total of 20 subjects participated in the study. The mean age was 25.5 years old (range 20-38 years). The study consisted of 8 male (40%) and 12 female (60%) subjects with a mean body mass index (BMI) of 23.6 kg/m2±2.85. The racial makeup was 100% Caucasian. Fifteen subjects received all 4 treatments.

Figure 5:
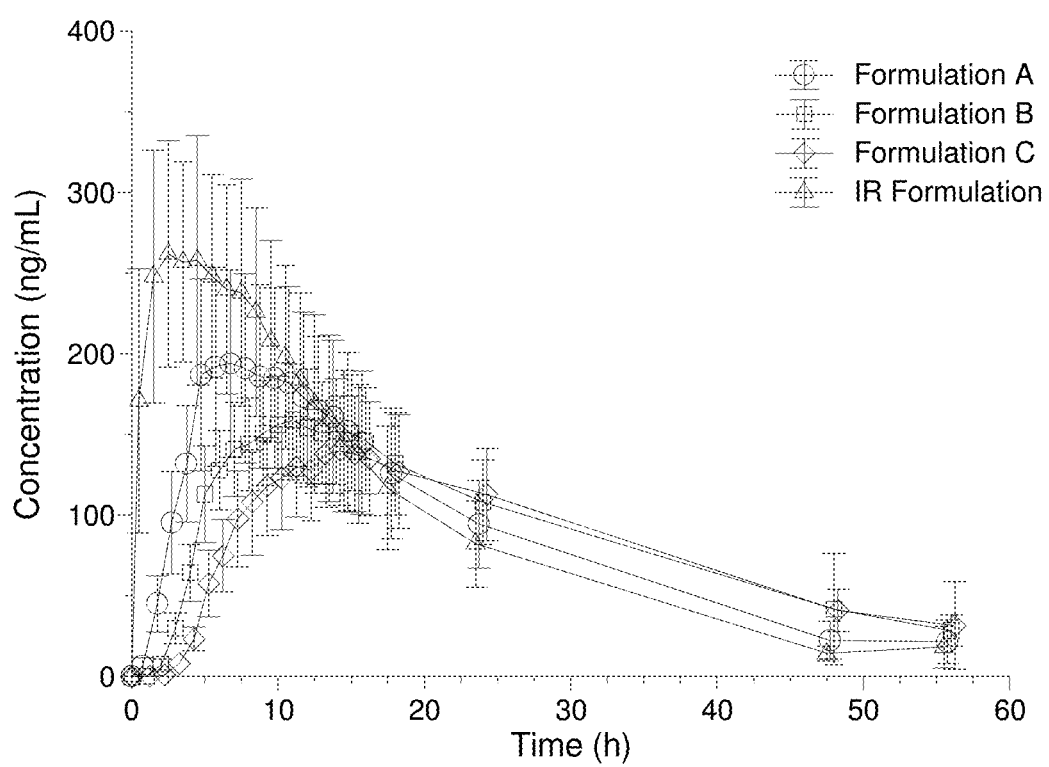
FIG. 5 shows a plot of mean (SD) plasma amantadine concentrations versus scheduled time for four (4) amantadine treatments.
Figure 6:
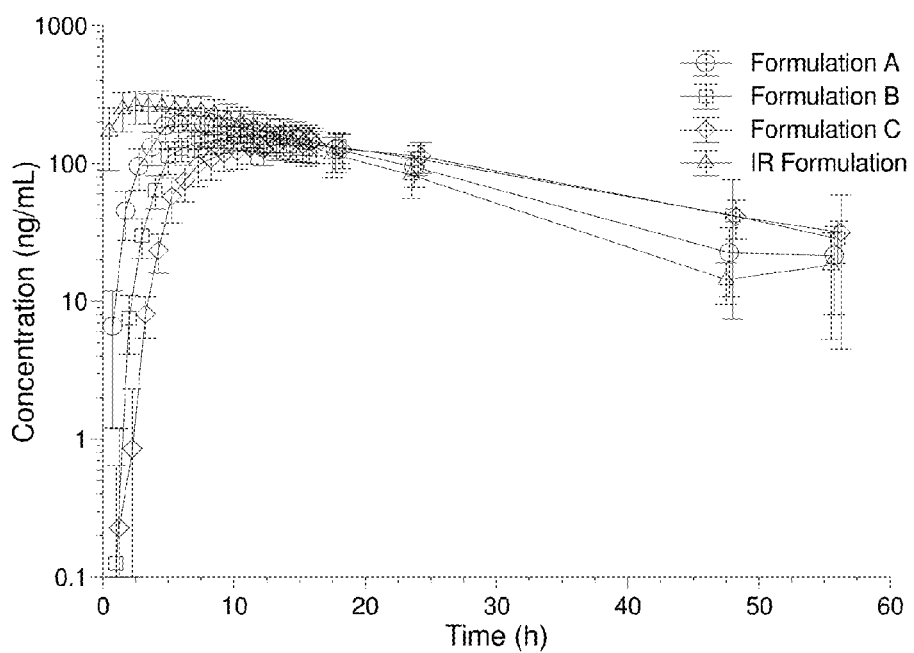
FIG. 6 shows a semi-logarithmic mean (SD) plasma amantadine concentrations versus scheduled time for four (4) amantadine treatments.

The PK results from this study showed that all three of the Amantadine ER formulations reduced the rate of absorption, based on the reduced values of Cmax and increased Tmax, compared to SYMMETREL® (Table 5, FIGS. 5, 6). The IR formulation had the highest mean Cmax (277±73.9 ng/mL) and shortest median Tmax (4 h) values. Formulations A, B, and C produced progressively lower Cmax and longer Tmax values. Cmax decreased from 204±61.4 to 166±34.8 to 149±34.4 ng/mL, and median Tmax increased from 7.0, to 11.0, to 14.0 h for formulations A, B, and C, respectively. Total amantadine exposure, as measured by AUC0-∞, was slightly lower in all three Amantadine ER formulations than SYMMETREL® but all three formulations had acceptable bioavailability (85-95%).

TABLE 5

Single Dose Pharmacokinetic Parameters of Three Formulations of Amantadine ER (Formulation A, B, and C), as Compared to SYMMETREL ® (Formulation IR)

| Parameter [a] | 100 mg Formulation A (n = 19) | 100 mg Formulation B (n = 17) | 100 mg Formulation C (n = 18) | 100 mg Formulation IR (n = 18) |
|---|---|---|---|---|
| $C_{max}$ (ng/mL) | 204 ± 61 | 166 ± 35 | 149 ± 34 | 277 ± 74 |
| $T_{max}$ (h) [range] | 7 [5-11] | 11 [5-15] | 14 [9-18] | 4 [2-6] |
| $AUC_{0-last}$ (ng*h/mL) | 5064 ± 1573 | 5028 ± 2328 | 4525 ± 1268 | 5488 ± 1730 |
| $AUC_{0-\infty}$ (ng*h/mL) | 5545 ± 1904 | 5724 ± 2369 | 5652 ± 2581 | 5907 ± 1907 |
| $t_{1/2}$ (h) | 13.9 ± 3.0 | 16.3 ± 5.2 | 18.3 ± 7.5 | 12.3 ± 3.5 |

[a] All parameters are reported as the mean ± standard deviation (SD), except $t_{max}$ which is reported as a median value (min to max range)

TABLE 6

Ratio ER/IR for $C_{max}$ and $AUC_{0-\infty}$

| Comparison | Variable | ER/IR[a] |
|---|---|---|
| A vs. IR | $C_{max}$ (ng/mL) | 66.0% |
|  | $AUC_{0-\infty}$ (ng*h/mL) | 85.3% |
| B vs. IR | $C_{max}$ (ng/mL) | 60.9% |
|  | $AUC_{0-\infty}$ (ng*h/mL) | 94.6% |
| C vs. IR | $C_{max}$ (ng/mL) | 51.2% |
|  | $AUC_{0-\infty}$ (ng*h/mL) | 88.5% |

[a] Point estimate of the geometric mean ratio (ER/IR).

Example 6: Food-Effect Evaluation of Amantadine ER

Objective:

The primary objective was to demonstrate that the amantadine ER formulations suitable for nighttime administration exhibit excellent bioavailability when administered with food. We determined the pharmacokinetics of a 100 mg capsule of an amantadine ER formulation (Example 3, Formulation B), when administered both with a high fat meal and in a fasted state.

Study Design:

This was a Phase 1, randomized, single dose, open-label, two-period, crossover, food-effect study to compare single 100 mg doses of Formulation I in healthy adult (18 to 45 years of age) male and female subjects in fed and fasted states. The study consisted of a 21-day to −2 day screening phase (prior to the scheduled dosing day) and two treatment periods, Period 1 and Period 2, with an 8-day wash-out period between treatment periods.

Methods:

After an overnight fast, the formulation was administered to the subjects while in a sitting position with 240 mL of water at ambient temperature for the fasted condition. For the fed condition, after the overnight fast, subjects were served a high fat and high calorie test meal (Guidance for Industry Food-Effect Bioavailability and Fed Bioequivalence Studies, December 2002) as breakfast, which they were required to consume completely within 30 minutes before taking the study medication. Subjects were randomized to one of two sequences, each composed of treatment administration under fed and fasted conditions separated by an eight day wash out period.

For each period, pharmacokinetic blood samples were collected at pre-dose and at 1, 2, 3, 4, 5, 6, 7, 8, 9, 10, 11, 12, 13, 14, 15, 16, 18, 24, 28, 48, 72, 96 and 144 hours after dosing in each period. Subjects were housed in the clinical facility at least 15 hours before investigational product administration and remained in the clinical facility for at least 28 hours after administration of the investigational product in each period. Samples after 28 hours in each period were collected on an ambulatory basis. Amantadine in plasma was quantified by a validated LC/MS/MS method. The pharmacokinetic parameters were calculated from the drug concentration-time profile by non-compartmental model using WinNonlin Professional Software—Version 5.0.1 (Pharsight Corporation, USA) for amantadine. Absence of food effect was defined as met if the point estimates and 90% confidence intervals (CI) for the ln-transformed $C_{max}$, $AUC_{last}$ and $AUC_\infty$ fed/fasting ratios of the population means were entirely within the standard accepted range of 80% to 125%. All statistical analyses for amantadine were performed using PROC MIXED of SAS® Release 9.1.3 (SAS Institute Inc., USA).

Routine safety monitoring was conducted during and after dosing in all subjects.

Results:

A total of 26 subjects participated in the study, 19 (73%) male and 7 (27%) female. The mean age was 26 years (range 19-44) and the mean BMI was 22.4 kg/m² (range 18.1-29.8). The racial makeup was 100% Asian. All subjects received at least one dose of study drug and were included in the safety analysis. Twenty-four (92.3%) subjects completed the study and were included in the pharmacokinetic analysis. Two subjects (7.7%) were withdrawn prior to completion of the study due protocol deviations.

The results of this study (Table 7) indicate that the single dose pharmacokinetics of Formulation B are not affected by food. The rate, as measured by $C_{max}$, and the extent, as measured by $AUC_{0-last}$ and $AUC_{0-\infty}$, of absorption of amantadine, administered with and without food, were equivalent (Table 8).

TABLE 7

Mean ± SD Pharmacokinetic Parameters after Single Dose Administration of 100 mg of Formulation B in Fed and Fasted States

| Parameters (Units)[a] | Mean ± SD (Un-transformed data) n = 24 | |
|---|---|---|
|  | Fasted State | Fed State |
| $T_{max}$ (h) | 11.9 ± 2.1 (8-15) | 9.5 ± 2.4 (5-16) |
| $C_{max}$ (ng/mL) | 198.8 ± 34.7 | 219.4 ± 41.5 |
| $AUC_{0-last}$ (ng*h/mL) | 5571.2 ± 1654.2 | 5394.4 ± 1581.5 |
| $AUC_{0-\infty}$ (ng*h/mL) | 5663.1 ± 1677.4 | 5476.6 ± 1590.7 |

TABLE 7-continued

Mean ± SD Pharmacokinetic Parameters after Single Dose
Administration of 100 mg of Formulation B in Fed and Fasted States

| | Mean ± SD (Un-transformed data) n = 24 | |
|---|---|---|
| Parameters (Units)[a] | Fasted State | Fed State |
| $t_{1/2}$ (h) | 11.9 ± 2.8 | 11.5 ± 2.0 |
| $t_{lag}$ (h) | 1.0 | 2.0 |

[a]All parameters are reported as the mean ± standard deviation (SD). $t_{max}$ is reported as the mean ± SD (min to max range).

TABLE 8

Geometric Least Squares Mean, Ratios and 90% Confidence Interval
for Formulation B (n = 24) in Fed and Fasted States

| | ln-transformed data Geometric Least Squares Mean | | | 90% Confidence |
|---|---|---|---|---|
| Parameters (Units) | Fed State | Fasted State | Ratio (Fed/Fasted)% | Interval (Parametric) |
| $C_{max}$ (ng/mL) | 215.6 | 195.8 | 110.1 | 104.4-116.2% |
| $AUC_{0\text{-}last}$ (ng*h/mL) | 5195.9 | 5344.2 | 97.2 | 91.0-103.8% |
| $AUC_{0\text{-}\infty}$ (ng*h/mL) | 5280.3 | 5434.7 | 97.2 | 90.9-103.8% |

Conclusion:

The results of this study indicate that the single dose pharmacokinetics of amantadine ER are not affected by food. The rate, as measured by $C_{max}$, and the extent, as measured by $AUC_{0\text{-}last}$ and $AUC_{0\text{-}\infty}$, of absorption of amantadine, administered with and without food, were equivalent.

Example 7: Pharmacokinetic Study Comparing Once-Daily Administration of Amantadine HCl ER Capsules with Twice-Daily Administration of Amantadine HCl IR Tablets in Healthy Adults Under Fasting Conditions Objective: The primary objective of this study was to measure at steady state under repeat or chronic dosing the pharmacokinetics of an ER amantadine formulation suitable for nighttime administration, and enable the calculation of critical PK parameters for future safety and efficacy studies (i.e., Cave-morning, Cave-day, Cave-night) of ER amantadine formulations administered at night. We compared the single dose and repeat dose pharmacokinetics of amantadine HCl administered twice daily as a commercially available immediate release (IR) formulation to a once daily amantadine extended release (ER) formulation (Example 3, Formulation B).

Study Design:

This was a two period, multiple dose, crossover study. After a 21 day screening period, 26 healthy male and female subjects were randomized to receive one of two treatments (amantadine ER 200 mg once daily or amantadine IR 100 mg twice daily) in Period-I, then crossed over to receive the other treatment in Period-II.

Methods:

Study drug administration started on day 1. Study drug was not administered on Day 2. Multiple dosing commenced on day 3 and continued for 7 days (through day 9). A washout period of 8 days separated the dose administrations. The study drug was administered with 240 mL of drinking water. No other fluids were allowed within 1 hour of dosing. For each period, pharmacokinetic blood samples were collected at pre-dose and at 1, 2, 3, 4, 5, 6, 8, 10, 11, 12, 13, 14, 15, 16, 17, 18, 20, 24, 28, 36, and 48 hours after the first dose. The morning trough (pre-dose) blood samples were collected on Days 7 and 8. Blood samples were again collected immediately before the morning dose on Day 9 and at 1, 2, 3, 4, 5, 6, 8, 10, 11, 12, 13, 14, 15, 16, 17, 18, 20, 24, 28, 48, 72, and 96 hours thereafter. Samples after 28 hours following the morning dose on day 9 were collected on an ambulatory basis in each period. Amantadine in plasma was quantified by a validated LC/MS/MS method. The pharmacokinetic parameters were calculated from the drug concentration-time profile by non-compartmental model using WinNonlin Professional Software-Version 5.0.1 (Pharsight Corporation, USA) for amantadine.

Statistical analyses were conducted to assess the pharmacokinetic profile of single dose and repeat dose amantadine HCl administered twice daily as a commercially available immediate release (IR) formulation compared to a once daily extended release (ER) formulation (Formulation B). An analysis of variance (ANOVA) was performed on the natural logarithms of $C_{max}$, $C_{min}$, and $AUC_{24}$ determined from the data following the dose of study drug on study day 9 using linear mixed effects model. The model included the fixed effects for sequence, period, regimen and a random subject effect. The confidence intervals were used to perform the 2 one-sided tests procedure for equivalence assessment. The confidence intervals were obtained by exponentiating the endpoints of the confidence intervals for the difference of mean logarithms obtained within the framework of the ANOVA model. The upper and lower limits of confidence intervals from the natural-log transformed data were back-exponentiated to obtain the 90% confidence interval for the ratio of geometric means. Equivalence was established if the exponentiated 90% confidence interval fell entirely within the interval (80.00%, 125.00%).

Repeated measures ANOVA was carried out for comparison of $C_{min}$ for day 7, 8 and 9 at 5% level of significance on both untransformed and ln-transformed data. Steady state was demonstrated if the repeated measures ANOVA test was found to be non-significant. The statistical analysis for amantadine was performed using PROC MIXED of SAS® Release 9.1.3 (SAS Institute Inc., USA).

Routine safety monitoring was conducted during and after dosing in all subjects, and at the end of the study.

Results:

A total of 26 subjects participated in the study, 22 (84.6%) male and 4 (15.4%) female. The mean age was 26 years (range 19-42) and the mean BMI was 22.9 kg/m² (range 18.1-28.8). The racial makeup was 100% Asian. All subjects received at least one dose of study drug and were included in the safety analysis. Twenty-four (92.3%) subjects completed the study and were included in the pharmacokinetic analysis. Two subjects (7.7%) were withdrawn from the PK analysis prior to completion of the study due to vomiting within 12 hours of dosing, which was a pharmacokinetic exclusion criterion.

Figure 2A:
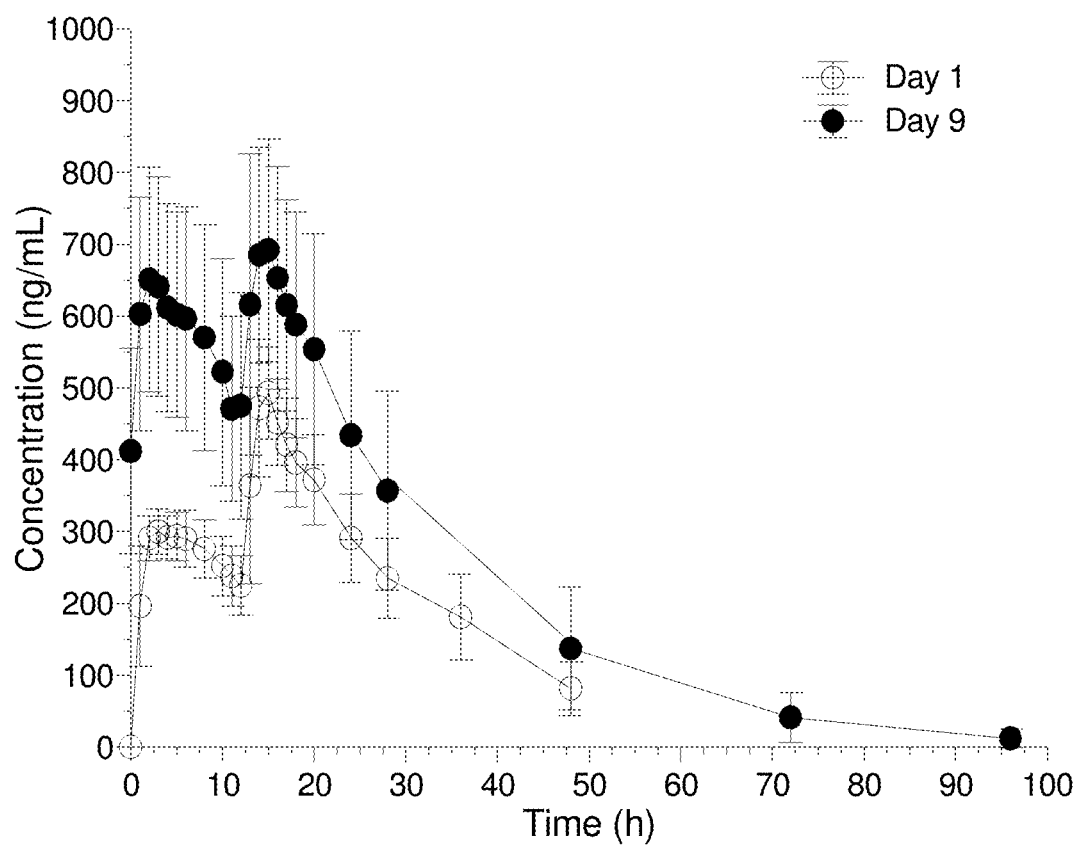
FIGS. 2A and 2B show the mean plasma concentration-time curves after administration of amantadine IR twice daily (A) and amantadine ER once daily (B) to healthy, adult, male and female subjects under fasting conditions on days 1 and 9.
Figure 2B:
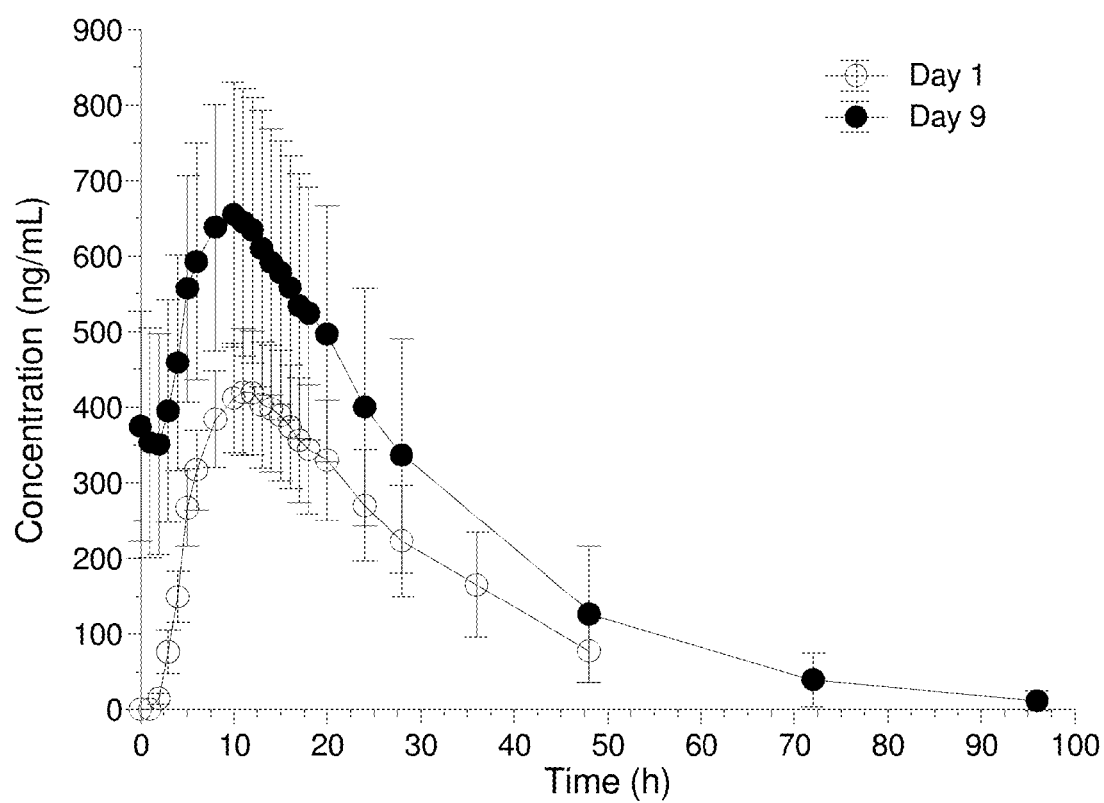
Figure 3:
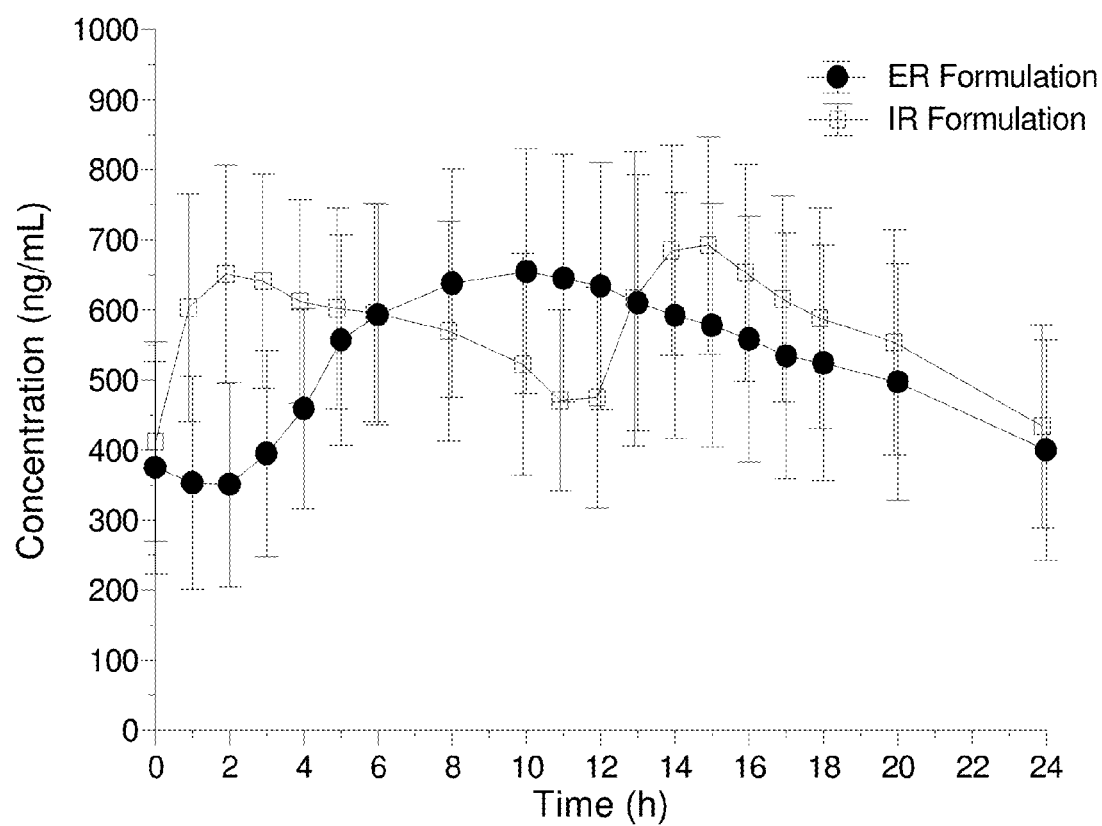
FIG. 3 shows a plot of mean plasma concentration of amantadine versus time curves after administration of amantadine IR twice daily and amantadine ER once daily to healthy, adult, male and female subjects under fasting conditions on day 9.

As expected from its half-life, once daily administration of amantadine ER and twice daily dosing of amantadine IR resulted in accumulation as measured by higher $C_{max}$ and AUC on Day 9 compared to Day 1 (Table 9 and FIG. 2). Steady state was achieved by Day 9 for both formulations as demonstrated by similar trough levels on Days 7, 8 and 9 (data not shown). At steady state (Day 9) plasma concentrations (FIG. 2, Table 9) and pharmacokinetic parameters (Table 9) were comparable for both formulations. Furthermore, the formulations are equivalent in terms of the extent and the rate of absorption of amantadine as measured by steady state $C_{max}$, $C_{min}$ and $AUC_{0-24}$ (Table 9), where equivalence is defined by the 90% CIs of the ratio of the least square means of the test versus reference for steady state $C_{max}$, $C_{min}$ and $AUC_{0-24}$ of Amantadine ER to Amantadine IR falling within 80%-125%.

TABLE 9

Mean (±SD) Pharmacokinetic Parameters of Amantadine after Single and Multiple Dose Administration of IR (100 mg BID) and ER (200 mg QD) Formulations

| Parameter (Units)[a] | IR (n = 24) | | ER (n = 24) | |
|---|---|---|---|---|
| | Day 1 | Day 9 | Day 1 | Day 9 |
| $t_{1/2}$ (h) | 13.2 ± 2.8 [9.1-18.8] | 12.6 ± 2.4 [9.4-18.1] | 13.7 ± 3.6 [9.1-22.7] | 12.8 ± 2.2 [9.2-17.4] |
| $t_{max}$ (h) | 14.42 ± 0.88 [13-16] | 12.6 ± 4.5 [1-15] | 11.4 ± 1.9 [8-18] | 10.3 ± 2.0 [8-18] |
| $C_{max}$ (ng/mL) | 530 ± 80 [407.5-752.7] | 728 ± 153 [538.4-1101.8] | 431 ± 84 [313.5-559.9] | 665 ± 179 [444.4-1140.0] |
| $AUC_{0-last}$ (ng h/mL) | 11989 ± 2224 [9243-17106] | 23040 ± 8273 [13133-46446] | 11171 ± 2773 [7326-16970] | 21362 ± 8946 [10821-47134] |
| $AUC_{0-\infty}$ (ng h/mL) | 13685 ± 3324 [10167-20989] | NA | 12900 ± 4087 [7817-22153] | NA |
| $AUC_{0-24}$ (ng h/mL) | 7695 ± 1026 [5967-10171] | 13752 ± 3586 [9085-22519] | 7173 ± 1367 [5021-9552] | 12680 ± 3879 [7896-23058] |
| $C_{min}$ (ng/mL) | — | 412.4 ± 142.6 [218.5-795.2] | — | 374.9 ± 151.7 [172.2-767.1] |

[a] All parameters are reported as the mean ± SD, [min to max range]
NA = not applicable Certain additional PK parameters that are important in determining the suitability of the ER amantadine formulation for once daily, night time administration are also reported in Table 10.

TABLE 10

Additional Steady State PK parameters of Amantadine ER

| | ER 200 mg QD | IR 100 mg BID |
|---|---|---|
| Cmax/Cmin | 1.86 | 1.68 |
| C-ave-8-16 hrs(ng/ml) | 614 | 586 |
| C-ave-8-12 hrs (ng/ml) | 643 | 510 |
| C-ave-16-24 hrs (ng/ml) | 502 | 569 |
| C-ave-0-8 hrs (ng/ml) | 465 | 586 |
| C-ave-8-16 hrs/C-ave-0-8 hrs | 1.32 | 1.00 |
| C-ave-8-12 hrs/C-ave-0-8 hrs | 1.38 | 0.87 |
| % Change in Plasma Concentration 0-3 hrs | 5% | 55% |
| % Change in Plasma Concentration 0-4 hrs | 23% | 48% |
| AUC 0-4 as % of AUC 24 | 12% | N/A |
| AUC 0-8 as % of AUC 24 | 30% | N/A |
| AUC 0-12 as % of AUC 24 | 51% | N/A |

Conclusion: the ER amantadine formulation exhibits the desired steady state PK properties that would make the same suitable for administration at night and for achieving desired efficacy and tolerability benefits. Specifically, the ER amantadine formulation administered once daily at night results in relatively slow initial rise in amantadine plasma concentration, higher average amantadine plasma concentrations 8 to 12 hours after administration relative to 0-8 hours after administration and thus if administered at night higher ratios of average day time to night time amantadine plasma concentrations relative to IR amantadine. Thus this formulation is well suited for administration at higher doses than current practice that are expected to be relatively well tolerated and potentially provide superior efficacy in the treatment of LID, fatigue and Parkinson's disease.

Example 8: Study Comparing Administration of Amantadine HCl ER Capsules Once Nightly with Twice-Daily Administration of Amantadine HCl IR Tablets in Normal Healthy Volunteers Objective: The primary objective is to compare the effects on sleep of amantadine extended release (ER) capsules (Formulation B) administered once daily at bedtime with amantadine immediate release (IR) tablets administered twice daily in normal healthy volunteers. This ER formulation exhibits a Cave, day/Cave, night=1.30.

Study Design:

This is a single-center, double-blind, triple-dummy, randomized, crossover study to compare the effects on sleep of amantadine ER capsules, QHS, amantadine IR tablets BID, and caffeine caplets (active comparator) in 30 normal healthy volunteers as assessed by overnight polysomnography (PSG) and standardized questionnaires (Stanford Sleepiness Scale (SSS); Modified Epworth Sleepiness Scale (m-ESS)/Karolinska Sleepiness Scale (KSS); Toronto Hospital Alertness Test (THAT)/ZOGIM Alertness Scale (ZOGIM-A); Visual analog scale of sleepiness/alertness (VAS)).

Study drugs are administered in 3 dosing periods. A single day's dosage of one drug is administered per dosing period. Each day of dosing is separated by a washout period of 1 week. A single day's dosage of amantadine ER (Formulation B) consists of one 220 mg capsule (or 2×110 mg capsule) administered at bed time (QHS; defined as 23:00 h for the purposes of this study). A single day's dosage of amantadine IR consists of one 100 mg capsule administered twice a day (BID; defined as 8:00 h and 16:00 h for the purposes of this study). A single day's dosage of caffeine consists of one 100 mg capsule administered three times a day (TID; defined as 8:00 h, 16:00 h, & 23:00 h for the purposes of this study).

All subjects are dosed three times a day, at 8:00 h, 16:00 h, & 23:00 h. At each hour of dosing, every subject receives either the active drug or the matching placebo for each of the 3 treatments. Whether the capsule, tablet, or caplet administered at a specific hour of dosing contains active study drug or is a placebo dummy is determined according to the dosing sequence and period to which the subject is assigned.

Consented subjects who meet eligibility criteria are randomized equally to one of 3 treatment sequences (groups), each comprising 3 single-day treatment periods separated by 1 week washout periods as described above. Additionally, there is a one-day, single-blind, placebo run-in prior to each double-blind dosing day. This is to allow subjects to acclimate to sleeping in the Clinical Research Unit (CRU) under conditions of PSG recording and to establish individual baseline (BL) PSG characteristics.

For each dosing period, subjects are admitted to a CRU equipped with a sleep laboratory the day before the first day of dosing with active study drug. They stay in the CRU overnight and through the entirety of the active drug-dosing day. They again stay overnight and then are discharged from the CRU the morning of the following day. For the first dosing period, the day of admission to the CRU (Day −1) constitutes the last day of the screening phase, and the day of discharge from the CRU constitutes the first day of the first washout period (Day 2). For the second dosing period, the day of re-admission to the CRU (Day 7) constitutes the last day of the first washout period, and the day of discharge (Day 9) will constitute the first day of the second washout period. For the third dosing period, the day of re-admission to the CRU (Day 14) constitutes the last day of the second washout period, and the day of discharge (Day 16) constitutes the first day of the follow-up phase.

On the day of admission (or re-admission) to the CRU, subjects undergo routine laboratory and vital sign testing. They are administered one each of the placebo dummies (for amantadine ER, amantadine IR, & caffeine) at 16:00 h and at 23:00 h in single-blind fashion. They are questioned for adverse events (AEs) and have vital signs checked immediately prior to each dosing. Blood is drawn for routine laboratory testing and toxicology screen prior to the 16:00 h dosing. Subjects spend the night in the sleep lab under conditions of PSG recording.

On the day of dosing with active study drug, subjects are awakened at 7:00 h and fill out a battery of sleep and alertness questionnaires They receive study drug (active or placebo) at 8:00 h, 16:00, and 23:00 h. They are questioned for AEs and have vital signs checked immediately prior to each dosing. Blood is drawn to measure plasma amantadine concentrations prior to the 23:00 h dosing.

On the day after dosing with active study drug, subjects are awakened at 7:00 h and fill out a battery of sleep and alertness questionnaires Shortly before 8:00 h, i.e., 9 hours after the last dosing time, they are questioned for AEs and have vital signs checked. Also, blood is drawn to measure plasma amantadine concentrations. Instructions for contacting the site to report any AEs are reviewed with the subjects prior to their discharge from the CRU. The schedule for returning to the PSU for the next dosing period (this applies to returning for Periods 2 & 3) or for telephone contact (this applies to the follow-up after the third dosing period) is be reviewed.

All subjects receive a follow-up telephone call 3 days following discharge from the CRU (Day 19).

AEs and concomitant medications are monitored throughout the study. Blood samples for measurement of blood plasma concentrations are drawn immediately prior to the 23:00 h dosing time on Days 1, 8, and 15, and at approximately 8:00 h on Days 2, 9, and 16.

Sleep parameters and measurements of sleepiness and alertness at each time point are listed by subject. Both composite scores and scores from the individual components of the PSG and questionnaires are tabulated and analyzed. For each parameter measured, descriptive summary statistics are calculated by sequence and treatment, including means (or medians, as appropriate), ranges, and standard deviations (SDs).

Inferential statistics are performed on selected results wherein the magnitude of the differences between the means across treatment groups relative to the variance suggests a possible differential treatment effect. Continuous variable data is analyzed by parametric statistics (repeated measures analysis of variance with appropriate supplemental post-hoc analyses and/or paired t-test). Categorical data and data not conforming to a normal distribution is analyzed by non-parametric statistics (Wilcoxon signed rank test). PSG data may also be assessed by multivariate analyses and/or spectral analyses.

Results:

A lack of increase in, or reduction of, sleep disturbances with QD administration of 220 mg of amantadine ER compared to BID administration of amantadine IR, as measured by PSG and a standardized sleep questionnaire (e.g. SSS, m-ESS, KSS, THAT, ZOGIM-A, or VAS), demonstrates the suitability of amantadine ER for once daily administration at bedtime.

Example 9: Study Comparing the Effects on Sleep and Efficacy of Amantadine HCl ER Capsules Administered Once Daily at Night Relative to Amantadine HCl IR Capsules Administered Twice Daily in Parkinson's Patients Objective:

To compare the effects on sleep and efficacy of amantadine extended release (ER) capsules.

Study Design:

This is a Multi-Center, Double-Blind, Randomized Study to Compare the Effects on Sleep and Efficacy of Amantadine Extended Release (ER) Capsules in 120 Parkinsons Patients as assessed by UPDRS (Unified Parkinson's Disease Rating Scale), UPDRS-IV (Unified Parkinson's Disease Rating Scale Part IV), AIMS (Abnormal Involuntary Movement Scale), overnight polysomnography (PSG) and standardized questionnaires (Stanford Sleepiness Scale (SSS); Modified Epworth Sleepiness Scale (m-ESS)/Karolinska Sleepiness Scale (KSS); Toronto Hospital Alertness Test (THAT)/ ZOGIM Alertness Scale (ZOGIM-A); Visual analog scale of sleepiness/alertness (VAS)).

All study drugs are administered orally. Treatment A consists of a placebo capsule administered in the morning and two 110 mg capsules of Amantadine (ER) and a placebo capsule administered at bed time. Treatment B consists of a placebo capsule administered in the morning and three 110 mg capsules of Amantadine (ER) administered at bed time. Treatment C consists of a 100 mg capsule of Amantadine IR administered in the morning and a 100 mg capsule of Amantadine IR and two placebo capsules administered at bed time. Treatment D consists of a placebo capsule administered in the morning and 3 placebo capsules administered at bed time.

Consented subjects who meet eligibility criteria are randomized equally to one of 3 treatment groups, each comprising 14-day treatment periods. Additionally, there is a one-day, single-blind, placebo run-in prior to each double-blind dosing day. This is to allow subjects to acclimate to sleeping in the Clinical Research Unit (CRU) under conditions of PSG recording and to establish individual baseline (BL) PSG characteristics.

For each dosing period, subjects are admitted to a CRU equipped with a sleep laboratory the day before the first day of dosing with active study drug. They stay in the CRU overnight and through the entirety of the active drug-dosing day. They again stay overnight and then are discharged from the CRU the morning of the following day.

Parkinson's scores are recorded in the mornings on days 1, 7 and 14 using standard scoring methods, including the UPDRS and AIM.

AEs and concomitant medications are monitored throughout the study.

Sleep parameters and measurements of sleepiness and alertness at each time point are listed by subject. Both composite scores and scores from the individual components of the PSG and questionnaires are tabulated and analyzed. For each parameter measured, descriptive summary statistics are calculated by sequence and treatment, including means (or medians, as appropriate), ranges, and standard deviations (SDs).

Inferential statistics are performed on selected results wherein the magnitude of the differences between the means across treatment groups relative to the variance suggests a possible differential treatment effect. Continuous variable data is analyzed by parametric statistics (repeated measures analysis of variance with appropriate supplemental post-hoc analyses and/or paired t-test). Categorical data and data not conforming to a normal distribution is analyzed by non-parametric statistics (Wilcoxon signed rank test). PSG data may also be assessed by multivariate analyses and/or spectral analyses.

Results:

An improvement in UPDRS, UPDRS-IV, AIM, lack of increase in, or reduction of, sleep disturbances, as measured by PSG and a standardized sleep questionnaire (e.g. SSS, m-ESS, KSS, THAT, ZOGIM-A, or VAS), demonstrates the suitability of amantadine ER for once daily administration at bedtime.

Example 10: Simulated Pharmacokinetic Characteristics of Higher Strength, Amantadine ER Formulations Administered at Nighttime Objective: The objective is to use the data generated in the clinical study described in Example 7 to predict steady state plasma concentration-time profiles of various IR and ER amantadine regimens at different dose levels to show the benefits of higher strength amantadine ER formulations administered at nighttime.

Methodology: Plasma concentration-time profiles from healthy volunteers that received multiple doses of the ER and IR formulations of amantadine per study procedures described in Example 7 (ADS-5101-MD-104) were used to develop a pharmacokinetic model describing each of the two formulations. This study was an open-label, randomized, two-treatment, two-period, two-way crossover study comparing once-daily amantadine ER capsules and twice-daily amantadine IR tablets in 26 healthy, adult male and female volunteers. Complete data from 24 individuals were used in this exercise. Blood samples for pharmacokinetic evaluation were collected after single dosing on Day 1 and at steady state on Day 9. In the first step of the analysis, WinNonlin 5.2.1 (Pharsight Corp., Mountain View, Calif.) was used to fit a one-compartment model with first-order input and first-order output, weighted 1/y (where y is the amantadine plasma concentration), to each individual's plasma concentration-time data obtained after single (Day 1) and repeated (Day 9) dose administration of amantadine IR and ER; the fitting was done separately for both formulations, but simultaneously for both days. Modeling assumptions employed include dose proportionality and constant clearance as a function of time.

The model is described by the following equation:

$$C = \frac{FD}{V(k_a - k)}[\exp(-k(t - t_{lag}))) - \exp(-k_a(t - t_{lag}))] \quad \text{Equation 1}$$

where C is the plasma concentration, F is the absolute bioavailability, D is dose, V is the volume of distribution, $k_a$ is the absorption rate constant, k is the elimination rate constant, t is time, and $t_{lag}$ is the lag time of absorption. The goodness of fit was verified by comparing the individual model predicted and observed concentration-time data from Study ADS-5101-MD-104. After Equation 1 was fitted to each individual's plasma concentration-time data, model parameter estimates of V/F, $k_a$, k, and $t_{lag}$ were obtained for each of the 24 subjects. The goodness of the prediction at steady state was confirmed by comparing the observed data and predicted steady-state concentrations of amantadine obtained after daily dosing of 200 mg as the ER and IR formulations (Day 9).

Figure 4:
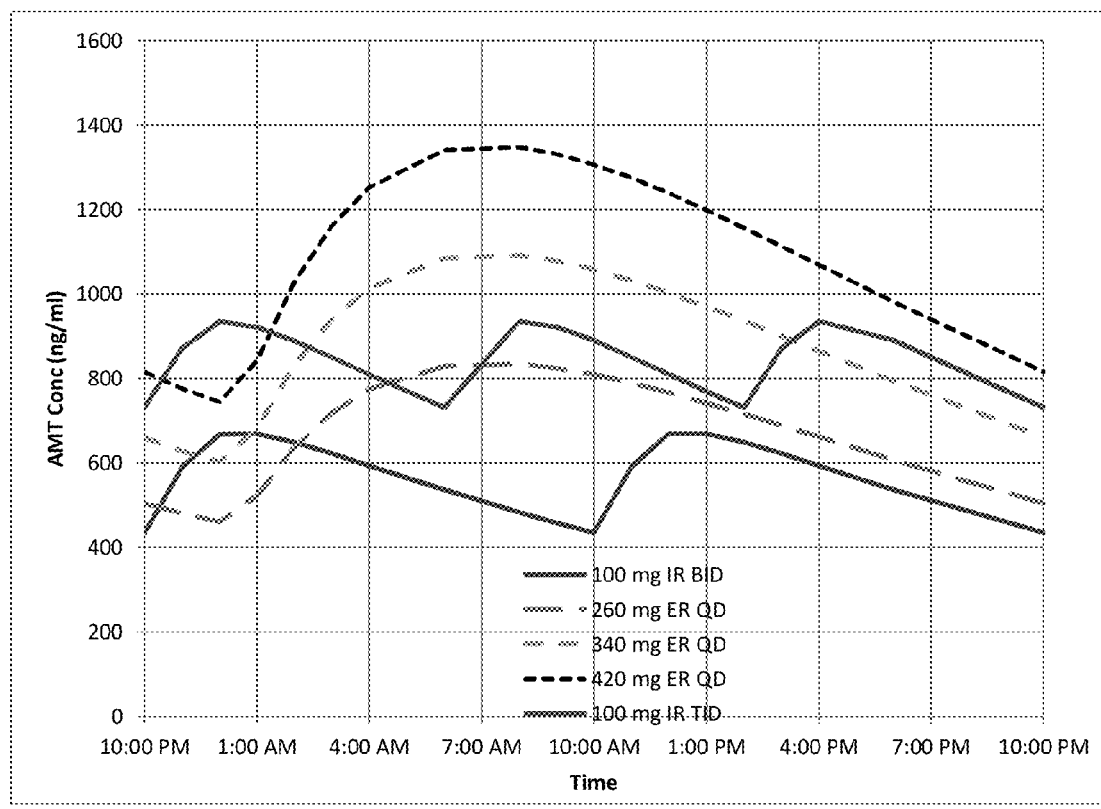
FIG. 4 shows the simulated mean plasma concentration of amantadine versus time curves following multiple dose administration of various strengths of immediate release amantadine dosed twice or thrice daily and various strengths of amantadine ER administered once daily.

In the second step of the analysis, individual model parameter estimates were used to simulate steady-state concentration-time profiles for each individual for both formulations by reinserting the individual parameter estimates into Equation 1, and summing the contribution of 7 sequential days of dosing, according to the following dosing regimens:
1. Once Daily (QD) dosing of 260, 340, and 420 mg of the ER formulation to steady state
2. Three times daily (TID) dosing of 100 mg of the IR formulation to steady state
3. Twice daily (BID) dosing of 100 mg of the IR formulation to steady state Results: FIG. 4 shows the simulated steady state plasma concentration time profiles for various ER amantadine doses along with various regimes of IR amantadine. Table 11 summarizes values of the pharmacokinetic parameters that affect the efficacy and tolerability of ER amantadine when administered at night.

TABLE 11

PK parameters associated with nighttime administration - morning peak benefit measured for ER Amantadine formulation

|  | IR 100 mg BID | IR 100 mg TID | ER 260 mg QD | ER 340 mg QD | ER 420 mg QD |
|---|---|---|---|---|---|
| Cmax (ng/ml) | 669 | 936 | 834 | 1091 | 1348 |
| Cmin (ng/ml) | 435 | 731 | 461 | 603 | 745 |
| Cmax/Cmin | 1.54 | 1.28 | 1.81 | 1.81 | 1.81 |
| C-ave-day (6 am-4 pm) (ng/ml) | 571 | 845 | 766 | 1002 | 1238 |
| C-ave-morn (6 am-10 am) (ng/ml) | 479 | 870 | 824 | 1078 | 1332 |
| C-ave-even (4 pm-10 pm) (ng/ml) | 522 | 852 | 591 | 773 | 955 |
| C-ave-night (10 pm-6 am) (ng/ml) | 596 | 843 | 616 | 805 | 995 |
| C-ave-day/C-ave-night | 0.96 | 1.00 | 1.24 | 1.24 | 1.24 |
| C-ave-morn/C-ave-night | 0.80 | 1.03 | 1.34 | 1.34 | 1.34 |
| C-ave-day relative to 100 mg BID IR | 1.00 | 1.48 | 1.34 | 1.76 | 2.17 |

As shown in Table 11 and in the figures, the ER amantadine formulations administered once daily at night result in higher ratios of average day time to night time amantadine plasma concentrations relative to IR amantadine and are predicted to be relatively well tolerated. The ER formulations also result in average day time amantadine plasma concentrations that are 1.3 to 2.2 fold that of IR amantadine administered at 100 mg twice daily and is predicted to result in significantly enhanced efficacy when administered to patients in the clinical study described in Example 11 below.

Example 11: A Randomized, Double-Blind, Placebo-Controlled Study of the Efficacy and Safety of Amantadine Extended Release Oral Capsules for the Treatment of Levodopa-Induced Dyskinesia in Parkinson's Disease Study Objectives: This study is designed to confirm dose range of Amantadine Extended Release (ER) oral capsules dosed once daily at nighttime for the treatment of levodopa-induced dyskinesia (LID) in subjects with Parkinson's Disease (PD). In addition, the study is designed to demonstrate the safety and tolerability of Amantadine ER oral capsules dosed once daily for the treatment of LID in subjects with PD. Finally, to confirm the steady-state pharmacokinetics of the Amantadine ER dosing regimens in Parkinsons patients and to correlate C-ave-day, Cave-morning, C-ave-morning/C-ave-night and C-ave-day/C-ave-night with the efficacy and tolerability of amantadine.

Study Design:

This will be a multi-center, randomized, double-blind, placebo-controlled, 4-arm parallel group study of Amantadine ER in subjects with PD and LID/Consenting subjects who meet eligibility criteria will be randomized 1:1:1:1 to receive one of the following 4 treatments, each administered as once daily, dosed at night, for 8 weeks:

Treatment A: Placebo,
Treatment B: 260 mg Amantadine ER (ADS-5102),
Treatment C: 340 mg Amantadine ER (ADS-5102)
Treatment D: 420 mg Amantadine ER (ADS-5102)

Subjects who are randomized to Treatment C or D (higher dose amantadine groups) will receive, in double-blind fashion, 260 mg Amantadine ER once daily during week 1, with an increase to either 340 mg or 420 mg once daily at the beginning of week 2. Dosing will continue through week 8.

Following completion of the baseline visit and randomization, subjects will return to the clinic after 1, 2, 4, 6, and 8 weeks of dosing, with a follow-up visit 14 days following the last dose of study drug. Study visits and assessments will be scheduled during morning hours when possible (9 am through 1 pm). A set of two 24-hour diaries will be completed during 48 hours prior to randomization and 48 hours prior to selected study visits. The diary will be used to score five different conditions in 30-minute intervals: Sleep, OFF, ON without dyskinesias, ON with nontroublesome dyskinesias, ON with troublesome dyskinesias.

Blood samples will be collected at selected study visits for determination of amantadine plasma concentrations, and evaluation of steady-state population pharmacokinetics. Subject participation during the study will be up to 12 weeks and will include a 2-week (maximum) screening period, 8-week (maximum) treatment period, and a 2-week follow-up period. Subjects who are unable to tolerate their assigned study drug assignment will permanently discontinue study drug and continue to be followed for safety through 2 weeks following the last dose of study drug.

Patient Eligibility Criteria:

Subjects are eligible to take part in the study if they meet the inclusion and do not meet the exclusion criteria. Selected key criteria are as follows:

Inclusion Criteria:
Male or female adults, residing in the community (i.e. not residing in an institution)
Between 30 and 75 years of age, inclusive
Ambulatory or ambulatory-aided (e.g. walker or cane) ability, such that the subject can come to required study visits
Knowledgeable and reliable caregiver/study partner, if appropriate, to accompany the subject to study visits
Signed a current IRB/IEC-approved informed consent form
Following training, the subject is willing and able to understand and complete the 24-hour home diary (caregiver assistance allowed)
Idiopathic Parkinson's Disease, complicated by dyskinesia (a MDS-UPDRS score will be determined during screening, but a minimum score is not required)
On a stable regimen of antiparkinson's medications, including levodopa, for at least 30 days prior to screening, and willing to continue that regimen during study participation
Presence of dyskinesia, defined as a minimum UDysRS score Exclusion Criteria:
Presence of other neurological disease that may affect cognition, including, but not limited to Alzheimer's dementia, Huntington's disease, Lewy body dementia, frontotemporal dementia, corticobasal degeneration, or motor or sensory dysfunction secondary to stroke or brain trauma.
Presence of cognitive impairment, as evidenced by a Mini-mental State Examination (MMSE) score of less than 24 during screening.
Presence of an acute major psychiatric disorder (e.g., Major Depressive Disorder) according to DSM-IV-TR or symptom (e.g., hallucinations, agitation, paranoia) that could affect the subject's ability to complete study assessments
Presence of sensory impairments (e.g., hearing, vision) that would impair the subject's ability to complete study assessments
History of alcohol or drug dependence or abuse, according to DSM-IV criteria, within 2 years prior to screening
History of seizures (excluding febrile seizures of childhood)
History of stroke or TIA within 2 years prior to screening
History of myocardial infarction, NYHA Congestive Heart Failure Class 3 or 4, or atrial fibrillation within 2 years prior to screening
History of cancer within 5 years prior to screening, with the following exceptions: adequately treated non-melanomatous skin cancers, localized bladder cancer, non-metastatic prostate cancer or in situ cervical cancer (these exceptions must be discussed with and approved by the Medical Monitor before study entry)
Any of the following lab abnormalities; Hemoglobin <10 g/dL, WBC <3.0×10$^9$/L, Neutrophils <1.5×10$^9$/L, Lymphocytes <0.5×10$^9$/L, Platelets <100×10$^9$/L, Hemoglobin A1C >9%, or Aspartate aminotransferase (AST) and/or alanine aminotransferase (ALT) >2 times the upper limit of normal Estimated GFR <50 mL/min/1.73 m² by Modification of Diet in Renal Disease (MDRD) or Cockcroft-Gault equation Any clinically significant ECG abnormalities Inability to swallow oral capsules, or a history of gastro-intestinal malabsorption that would preclude the use of oral medication Study Endpoints:

The primary efficacy endpoint will be the change from baseline to week 8 in the Unified Dyskinesia Rating Scale (UDysRS) score. Key secondary endpoints will include:

ON time without troublesome dyskinesia (ON without dyskinesia plus ON with nontroublesome dyskinesia), based on a standardized PD home diary Unified Parkinson's Disease Rating Scale (MDS-UP-DRS), overall score Fatigue as measured by the Fatigue Severity Scale (FSS). This scale includes 9 questions that are completed by the patient using a rating scale from 1 (strongly disagree) to 7 (strongly agree). This fatigue scale is recommended by MDS for both screening and severity rating (2010)

Safety, including adverse events, safety-related study drug discontinuations, vital signs, and laboratory tests.

The following mixture of traditional and new scales have been selected for this phase 2 study:

Unified Dyskinesia Rating Scale (UDysRS) will be used for primary outcome measure. This scale has four parts, and a total possible score of 104:
  I: Historical Disability (patient perceptions) of On-Dyskinesia impact
  II: Historical Disability (patient perceptions) of Off-Dystonia impact
  III: Objective Impairment (dyskinesia severity, anatomic distribution, and type, based on 4 observed activities)
  IV: Objective Disability based on Part III activities ON time without troublesome dyskinesia, based on a standardized Parkinson's Disease home diary (suggest Test Diary II), [33] will be a secondary outcome measure. This scale has been used in number of studies with mixed success [34]. However, most KOLs feel that subject-reported dairy data must be collected, and needs to support the primary outcome measure.

Unified Parkinson's Disease Rating Scale (UPDRS), part IV, items 32 (duration of dyskinesias: 0=none, 4=76-100% of the waking day) and 33 (disability of dyskinesias: 0=not disabling, 4=completely disabling) will be a secondary outcome measure. This scale is a traditional scale used in PD for many years and these items have been utilized in most LID studies.

Cognitive Scales: Global caregiver impression, depression and other scales will be employed to measure the mental status benefits of ER amantadine.

Statistical Methods

Efficacy Analyses: The efficacy analysis population will include all randomized and dosed subjects who provide at least one post-baseline efficacy assessment. For the efficacy endpoint of UDysRS score, the change from baseline to week 8 will be analyzed using an analysis of covariance (ANCOVA) model with treatment group as a factor and the UDysRS baseline value as a covariate. The primary analysis will compare the 260 mg ADS-5102 group to the placebo group using a two-sided test at the 5% level of significance. If the primary comparison is statistically significant (p<0.05), then the 340 mg and 420 mg ADS-5102 groups will be compared to placebo, also using a two-sided test at the 5% level of significance.

The secondary endpoints will be analyzed using the same types of ANCOVA models as described for the primary endpoint. All secondary comparisons between treatment groups will be performed using two-sided tests at the 5% level of significance. A last observation carried forward (LOCF) approach will be utilized for missing data. The primary efficacy analysis will be repeated for the per-protocol population, a subset of the efficacy analysis population who provide week 8 efficacy assessments.

Safety Analyses:

The safety analysis population will include all randomized subjects who receive at least one dose of study drug. All safety endpoints will be analyzed from the time of first dose through the completion of follow-up (or 2 weeks following the last dose of study drug). A safety analysis will also be done on the safety reported during the first 2 weeks of study drug treatment, in order to assess tolerability of initial dosing with ADS-5102 amantadine ER.

Results: following improvements are expected from this study are shown in the table below. Additional endpoints are described that Significant (20-60%) reduction in dyskinesia score measured by acceptable primary endpoint (e.g., UDysRS)

Increase in ON time without troubling dyskinesia by 20-60%

Improvement in UPDRS from 5% to 20%.

Improvement in Parkinson's fatigue (FSS) from 5% to 60%.

Improvement in mood by PGI from 5% to 20%.

| Instruments for Dyskinesia | % Clinical Effect (Placebo-Active/Placebo) | Range of Scores |
|---|---|---|
| Unified Dyskinesia Rating Scale (UDysRS) | 5-60% | 0-104 (4 parts, 26 items total, each 0, normal-4, severe) |
| Unified Parkinson's Disease Rating Scale (UPDRS, MDS revision) | 5-20% | |
| Part IV | 5-60% | 0-24 (6 items, each 0, normal-4, severe) |
| Part IV, dyskinesia items only | 5-60% | 0-8 (2 dyskinesia items, 4.1 and 4.2, each 0, normal-4, severe) |
| Parkinson's Disease Home Diary (Hauser et al) | 5-40% | 0-100% (on time without dyskinesia or with nontroublesome dyskinesia) |

Example 12: Simulated Pharmacokinetic Characteristics of Amantadine ER Formulations with a Delayed Release Coat Suitable for Night Time Administration Objective: The objective is to evaluate the pharmacokinetic profile of two alternative ER formulations of amantadine suitable for nighttime administration—Formulation 1, which is the formulation tested in Example 7, and Formulation 2, which is the formulation tested in Example 7, but with a delayed release over coat on top of the extended release coat.

Plasma concentration-time profiles from healthy volunteers, who received multiple doses of the ER and IR formulations of amantadine per study procedures described in Example 7 (ADS-5101-MD-104), were used to develop a pharmacokinetic model describing each of the two formulations. This study was an open-label, randomized, two-treatment, two-period, two-way crossover study comparing once-daily amantadine ER capsules and twice-daily amantadine IR tablets in 26 healthy, adult male and female volunteers. Complete data from 24 individuals were used in this exercise. Blood samples for pharmacokinetic evaluation were collected after single dosing on Day 1 and at steady state on Day 9. In the first step of the analysis, WinNonlin 5.2.1 (Pharsight Corp., Mountain View, Calif.) was used to fit a one-compartment model with first-order input and first-order output, weighted 1/y (where y is the amantadine plasma concentration), to each individual's plasma concentration-time data obtained after single (Day 1) and repeated (Day 9) dose administration of amantadine IR and ER; the fitting was done separately for both formulations, but simultaneously for both days. Modeling assumptions employed include dose proportionality and constant clearance as a function of time.

The model is described by the following equation $$C = \frac{FD}{V(k_a - k)}[\exp(-k(t - t_{lag}))) - \exp(-k_a(t - t_{lag}))]\quad \text{Equation 1}$$

where C is the plasma concentration, F is the absolute bioavailability, D is dose, V is the volume of distribution, $k_a$ is the absorption rate constant, k is the elimination rate constant, t is time, and $t_{lag}$ is the lag time of absorption. The goodness of fit was verified by comparing the individual model predicted and observed concentration-time data from Study ADS-5101-MD-104. After Equation 1 was fitted to each individual's plasma concentration-time data, model parameter estimates of V/F, $k_a$, k, and $t_{lag}$ were obtained for each of the 24 subjects. The goodness of the prediction at steady state was confirmed by comparing the observed data and predicted steady-state concentrations of amantadine obtained after daily dosing of 200 mg as the ER and IR formulations (Day 9).

Figure 7:
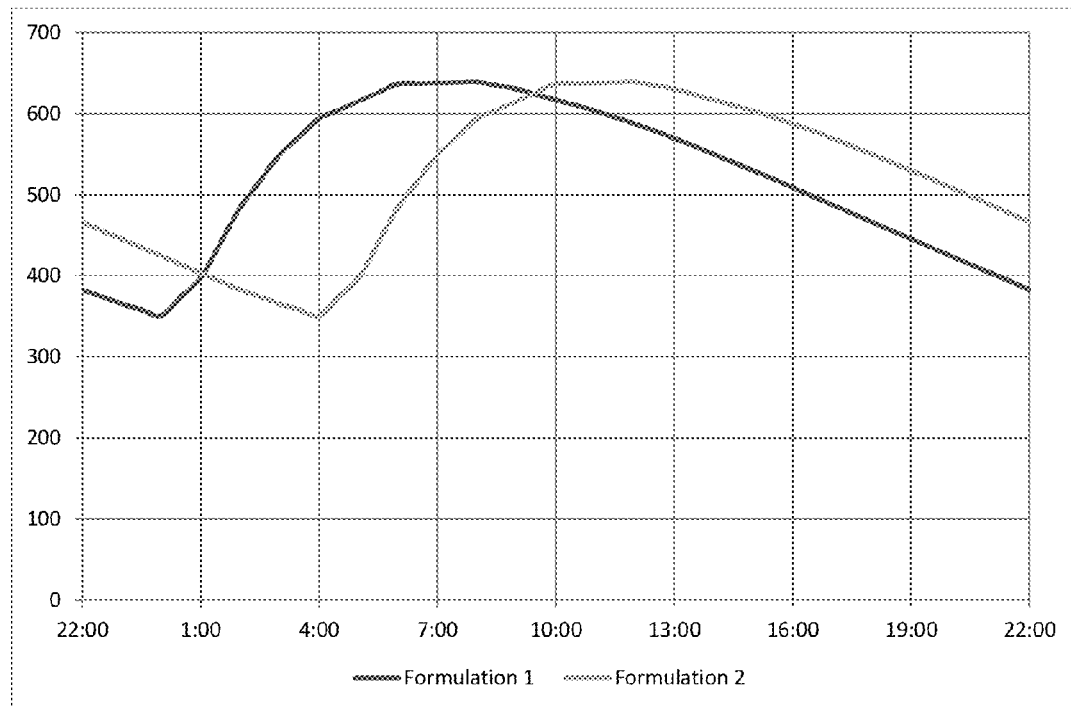
FIG. 7 shows simulated steady state plasma concentration time profiles for the ER amantadine formulations as described in Example 12. The ER amantadine formulation 2, administered once daily at night, results at steady state in about 4 hour delay in achieving peak plasma concentration relative to formulation 1.

In the second step of the analysis, individual model parameter estimates were used to simulate steady-state concentration-time profiles for each individual for both formulations by reinserting the individual parameter estimates into Equation 1, and summing the contribution of 7 sequential days of dosing, according to the following dosing regimens:
1. Once Daily (QD) dosing of 200 mg of the ER Formulation 1 to steady state
2. Once Daily (QD) dosing of 200 mg of the ER Formulation 2 to steady state Results: FIG. 7 shows the simulated steady state plasma concentration time profiles for the two ER amantadine formulations. (Amantadine blood plasma concentrations are shown on the y, time of day on the x-axis.) As shown in FIG. 7, the ER amantadine formulation 2 administered once daily at night results in about a 4 hour delay in achieving peak plasma concentration at steady state relative to formulation 1. Thus, a formulation comprising a delayed release coat on top of the extended release coat has a very favorable pharmacokinetic profile in that it maximizes the daytime plasma exposure to amantadine whilst minimizing night plasma exposure at steady state.

While preferred embodiments of the present invention have been shown and described herein, such embodiments are provided by way of example only. Numerous variations, changes, and substitutions will now occur to those skilled in the art without departing from the invention. It should be understood that various alternatives to the embodiments of the invention described herein may be employed in practicing the invention. All references cited herein are incorporated herein by reference in their entirety.

We claim:

1. A method of administering a dose of a pharmaceutical composition of a drug, wherein the drug is selected from the group consisting of amantadine and pharmaceutically acceptable salts thereof, to a human patient in need thereof, comprising administering said dose of said pharmaceutical composition to said human patient orally, once daily 0 to 4 hours before bedtime, wherein said dose of said pharmaceutical composition comprises: (i) 220 mg to 455 mg of the drug; and (ii) one or more excipients, wherein at least one of said one or more excipients modifies the release of said drug to provide an extended release dosage form,
   wherein, a unit dosage form of said pharmaceutical composition has an in vitro dissolution profile characterized by release of said drug from said pharmaceutical composition that is not more than 25% in two hours and at least 80% at 12 hours using a USP Apparatus II (Paddles) at 50 rpm with 500 ml water at 37° C. as the dissolution medium, and
   wherein when said pharmaceutical composition is dosed in a single dose, fasted, human pharmacokinetic study in healthy subjects, the Tmax for amantadine is 8 to 20 hours.

2. The method of claim 1, wherein said Tmax is 9 to 18 hours.

3. The method of claim 1, wherein said Tmax is 11 to 18 hours.

4. The method of claim 1, wherein said in vitro dissolution profile is characterized by release of the drug from said pharmaceutical composition that is not more than 10% in one hour.

5. The method of claim 1, wherein said in vitro dissolution profile is characterized by release of the drug from said pharmaceutical composition that is 40% to 80% in 6 hours.

6. The method of claim 4, wherein said in vitro dissolution profile is characterized by release of the drug from said pharmaceutical composition that is 40% to 80% in 6 hours.

7. The method of claim 1, wherein said in vitro dissolution profile is characterized by release of the drug from said pharmaceutical composition that is 25% to 55% in 6 hours.

8. The method of claim 4, wherein said in vitro dissolution profile is characterized by release of the drug from said pharmaceutical composition that is 25% to 55% in 6 hours.

9. The method of claim 1, wherein said in vitro dissolution profile is characterized by release of the drug from said pharmaceutical composition that is 30% to 50% in 4 hours.

10. The method of claim 4, wherein said in vitro dissolution profile is characterized by release of the drug from said pharmaceutical composition that is 30% to 50% in 4 hours.

11. The method of claim 5, wherein said in vitro dissolution profile is characterized by release of the drug from said pharmaceutical composition that is 30% to 50% in 4 hours.

12. The method of claim 1, wherein said pharmaceutical composition comprises one, two, three or four unit dosage forms.

13. The method of claim 1, wherein said pharmaceutical composition comprises one, two, or three capsules containing coated pellets.

14. The method of claim 1, wherein said pharmaceutical composition comprises one, two, or three capsules.

15. The method of claim 1, wherein said pharmaceutical composition is selected from the group consisting of one unit dosage form comprising 340 mg of said drug and two unit dosage forms each comprising 170 mg of said drug.

16. The method of claim 15, wherein said drug is a pharmaceutically acceptable salt of amantadine.

17. The method of claim 15, wherein said drug is amantadine hydrochloride.

18. The method of claim 1, wherein said drug is a pharmaceutically acceptable salt of amantadine.

19. The method of claim 1, wherein said drug is amantadine hydrochloride.

\* \* \* \* \*